United States Patent
Montaño-Suarez et al.

(10) Patent No.: US 11,529,397 B2
(45) Date of Patent: Dec. 20, 2022

(54) METHOD OF TREATING MUCOPOLYSACCHARIDOSIS TYPE IVA

(71) Applicants: Adriana M. Montaño-Suarez, St. Louis, MO (US); Angela Catalina Sosa-Molano, Bogotá (CO); Alan Knutsen, Webster Groves, MO (US); Clifford Bellone, St. Louis, MO (US); Shunji Tomatsu, Wilmington, DE (US); Luis Barrera, Bogotá (CO)

(72) Inventors: Adriana M. Montaño-Suarez, St. Louis, MO (US); Angela Catalina Sosa-Molano, Bogotá (CO); Alan Knutsen, Webster Groves, MO (US); Clifford Bellone, St. Louis, MO (US); Shunji Tomatsu, Wilmington, DE (US); Luis Barrera, Bogotá (CO)

(73) Assignee: Saint Louis University, St. Louis, MO (US)

( * ) Notice: Subject to any disclaimer, the term of this patent is extended or adjusted under 35 U.S.C. 154(b) by 920 days.

(21) Appl. No.: 15/876,892

(22) Filed: Jan. 22, 2018

(65) Prior Publication Data
US 2019/0224283 A1    Jul. 25, 2019

(51) Int. Cl.
*A61K 39/00* (2006.01)
*A61K 38/46* (2006.01)
*A61K 9/00* (2006.01)

(52) U.S. Cl.
CPC .......... *A61K 38/465* (2013.01); *A61K 9/0019* (2013.01); *A61K 9/0053* (2013.01); *C12Y 301/06004* (2013.01)

(58) Field of Classification Search
None
See application file for complete search history.

(56) References Cited

U.S. PATENT DOCUMENTS

| | | |
|---|---|---|
| 6,929,796 B1 | 8/2005 | Conti-Fine |
| 2007/0105211 A1 | 5/2007 | Ota et al. |
| 2011/0177107 A1 | 7/2011 | Howard |

FOREIGN PATENT DOCUMENTS

WO    2012012718 A2    1/2012

OTHER PUBLICATIONS

Bell et al., In Trans T Cell Tolerance Diminishes Autoantibody Responses and Exacerbates Experimental Allergic Encephalomyelitis. Immunol. 2008, vol. 180, No. 3, pp. 1508-1516.
Dong et al., Ped. Transplant., 1999, vol. 161, pp. 181-189.
Dvorak-Ewell et al., Enzyme replacement in a human model of mucopolysaccharidosis IVA in vitro and its biodistribution in the cartilage of wild type mice. PloS One, 2010, vol. 5, No. 8, pp. e12194.
Faria et al., Clin. Dev. Immunol., 2006, vol. 13, No. 2-4, pp. 143-157.
Goodnow et al., The Lancet, 2001, vol. 357, pp. 2115-2121.
Kraus et al., Curr. Opin. Gastroenterol. 2005, vol. 21, pp. 692-696.
Marketletter, Marketletter Pubs., 069/13/1999.
Ohashi et al., Oral administratio nof recominant human acid a-glucosidase reduces specific antibody formation against enzyme in mouse. Mol. Genet. Metab, 2011, vol. 103, No. 1, pp. 98-100.
Peters et al., The design and implementation of the immune epitope database and analysis resource. Immunogenetics, 2005, vol. 57., No. 5, pp. 326-336.
Pozzilli et al., Diabetol. 2000, vol. 43, pp. 1000-1004.
Rivera-Colon et al., The structure of human GALNS reveals the molecular basis for mucopolysaccharidosis IVA. J. Mol. Biol., Aug. 2012, vol. 423, No. 5, pp. 736-751.
Schwartz R.H., Immunologic Tolerance in Fundamental Immunology, 6th ed., Paul, W. editor, 2008, Ch. 29, p. 698.
Skyler et al., Diabetes Care. 2005, vol. 28, pp. 1068-1076.
Sosa et al., Identification of Immunodominant Epitopes in N-Acetylgalactosamine 6-Sulfate Sulfatase (GALNS) for Designing an Effective Peptide-Based Immunotherapy. Molecular Genetics and Metabolism, vol. 105, No. 2, p. S58.
Tomatsu et al., Enhancement of drug delivery: enzyme-replacement therapy for murine Morquio A syndrome. Mol. Ther. 2010, vol. 18, No. 6, pp. 1094-1002.
Wang et al., Mechanism of oral tolerance induction to therapeutic proteins. Adv. Drug Deliv. Rev., 2013, vol. 65, No. 6, pp. 759-773.
Weiner et al., Oral Tolerance, Immunol Rev., 2011, vol. 241, No. 1, pp. 241-259.

*Primary Examiner* — G. R. Ewoldt
(74) *Attorney, Agent, or Firm* — Stinson LLP

(57) ABSTRACT

Disclosed are methods and compositions for determining immunodominant peptides of target enzymes used in enzyme replacement therapy for lysosomal storage disorders. More specifically disclosed are immunodominant peptides for N-acetylgalactosamine-6-sulfatase (GALNS). Also disclosed are methods of inducing oral tolerance towards a target enzyme through oral administration of immunodominant peptides prior to commencing enzyme replacement therapy. More specifically disclosed is a method of inducing oral tolerance for GALNS, by orally administering specific immunodominant peptides for GALNS; in subjects suffering from mucopolysaccharidosis type IVA prior to commencing enzyme replacement therapy using GALNS.

13 Claims, 36 Drawing Sheets

Figure 1:
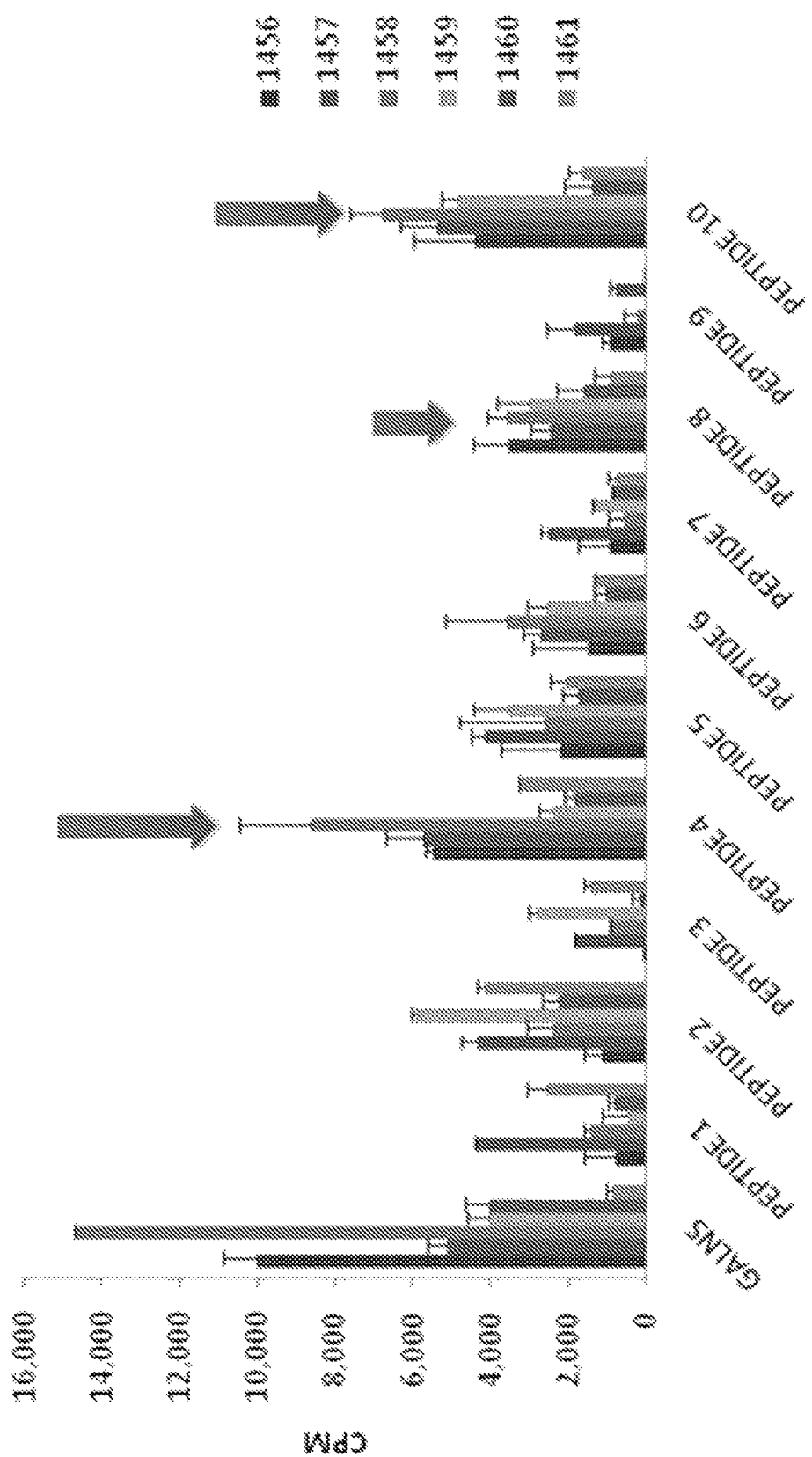

Specification includes a Sequence Listing.

SEQUENCE LISTING

```
<160> NUMBER OF SEQ ID NOS: 12

<210> SEQ ID NO 1
<211> LENGTH: 522
<212> TYPE: PRT
<213> ORGANISM: Homo sapiens

<400> SEQUENCE: 1

Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
            20                  25                  30

Ile Leu Leu Leu Leu Met Asp Asp Met Gly Trp Gly Asp Leu Gly Val
        35                  40                  45

Tyr Gly Glu Pro Ser Arg Glu Thr Pro Asn Leu Asp Arg Met Ala Ala
    50                  55                  60

Glu Gly Leu Leu Phe Pro Asn Phe Tyr Ser Ala Asn Pro Leu Cys Ser
65                  70                  75                  80

Pro Ser Arg Ala Ala Leu Leu Thr Gly Arg Leu Pro Ile Arg Asn Gly
                85                  90                  95

Phe Tyr Thr Thr Asn Ala His Ala Arg Asn Ala Tyr Thr Pro Gln Glu
            100                 105                 110

Ile Val Gly Gly Ile Pro Asp Ser Glu Gln Leu Leu Pro Glu Leu Leu
        115                 120                 125

Lys Lys Ala Gly Tyr Val Ser Lys Ile Val Gly Lys Trp His Leu Gly
    130                 135                 140

His Arg Pro Gln Phe His Pro Leu Lys His Gly Phe Asp Glu Trp Phe
145                 150                 155                 160

Gly Ser Pro Asn Cys His Phe Gly Pro Tyr Asp Asn Lys Ala Arg Pro
                165                 170                 175

Asn Ile Pro Val Tyr Arg Asp Trp Glu Met Val Gly Arg Tyr Tyr Glu
            180                 185                 190

Glu Phe Pro Ile Asn Leu Lys Thr Gly Glu Ala Asn Leu Thr Gln Ile
        195                 200                 205

Tyr Leu Gln Glu Ala Leu Asp Phe Ile Lys Arg Gln Ala Arg His His
    210                 215                 220
```

```
Pro Phe Phe Leu Tyr Trp Ala Val Asp Ala Thr His Ala Pro Val Tyr
225                 230                 235                 240

Ala Ser Lys Pro Phe Leu Gly Thr Ser Gln Arg Gly Arg Tyr Gly Asp
            245                 250                 255

Ala Val Arg Glu Ile Asp Asp Ser Ile Gly Lys Ile Leu Glu Leu Leu
        260                 265                 270

Gln Asp Leu His Val Ala Asp Asn Thr Phe Val Phe Thr Ser Asp
    275                 280                 285

Asn Gly Ala Ala Leu Ile Ser Ala Pro Glu Gln Gly Gly Ser Asn Gly
290                 295                 300

Pro Phe Leu Cys Gly Lys Gln Thr Thr Phe Glu Gly Gly Met Arg Glu
305                 310                 315                 320

Pro Ala Leu Ala Trp Trp Pro Gly His Val Thr Ala Gly Gln Val Ser
                325                 330                 335

His Gln Leu Gly Ser Ile Met Asp Leu Phe Thr Thr Ser Leu Ala Leu
            340                 345                 350

Ala Gly Leu Thr Pro Pro Ser Asp Arg Ala Ile Asp Gly Leu Asn Leu
        355                 360                 365

Leu Pro Thr Leu Leu Gln Gly Arg Leu Met Asp Arg Pro Ile Phe Tyr
370                 375                 380

Tyr Arg Gly Asp Thr Leu Met Ala Ala Thr Leu Gly Gln His Lys Ala
385                 390                 395                 400

His Phe Trp Thr Trp Thr Asn Ser Trp Glu Asn Phe Arg Gln Gly Ile
                405                 410                 415

Asp Phe Cys Pro Gly Gln Asn Val Ser Gly Val Thr Thr His Asn Leu
            420                 425                 430

Glu Asp His Thr Lys Leu Pro Leu Ile Phe His Leu Gly Arg Asp Pro
        435                 440                 445

Gly Glu Arg Phe Pro Leu Ser Phe Ala Ser Ala Glu Tyr Gln Glu Ala
    450                 455                 460

Leu Ser Arg Ile Thr Ser Val Val Gln Gln His Gln Glu Ala Leu Val
465                 470                 475                 480

Pro Ala Gln Pro Gln Leu Asn Val Cys Asn Trp Ala Val Met Asn Trp
                485                 490                 495

Ala Pro Pro Gly Cys Glu Lys Leu Gly Lys Cys Leu Thr Pro Pro Glu
            500                 505                 510

Ser Ile Pro Lys Lys Cys Leu Trp Ser His
            515                 520

<210> SEQ ID NO 2
<211> LENGTH: 496
<212> TYPE: PRT
<213> ORGANISM: Homo sapiens

<400> SEQUENCE: 2

Ala Pro Gln Pro Pro Asn Ile Leu Leu Leu Leu Met Asp Asp Met Gly
1               5                   10                  15

Trp Gly Asp Leu Gly Val Tyr Gly Glu Pro Ser Arg Glu Thr Pro Asn
            20                  25                  30

Leu Asp Arg Met Ala Ala Glu Gly Leu Leu Phe Pro Asn Phe Tyr Ser
        35                  40                  45

Ala Asn Pro Leu Cys Ser Pro Ser Arg Ala Ala Leu Leu Thr Gly Arg
    50                  55                  60

Leu Pro Ile Arg Asn Gly Phe Tyr Thr Thr Asn Ala His Ala Arg Asn
```

```
                65                  70                  75                  80
Ala Tyr Thr Pro Gln Glu Ile Val Gly Gly Ile Pro Asp Ser Glu Gln
                    85                  90                  95
Leu Leu Pro Glu Leu Lys Lys Ala Gly Tyr Val Ser Lys Ile Val
            100                 105                 110
Gly Lys Trp His Leu Gly His Arg Pro Gln Phe His Pro Leu Lys His
                115                 120                 125
Gly Phe Asp Glu Trp Phe Gly Ser Pro Asn Cys His Phe Gly Pro Tyr
            130                 135                 140
Asp Asn Lys Ala Arg Pro Asn Ile Pro Val Tyr Arg Asp Trp Glu Met
145                 150                 155                 160
Val Gly Arg Tyr Tyr Glu Glu Phe Pro Ile Asn Leu Lys Thr Gly Glu
                165                 170                 175
Ala Asn Leu Thr Gln Ile Tyr Leu Gln Glu Ala Leu Asp Phe Ile Lys
            180                 185                 190
Arg Gln Ala Arg His His Pro Phe Phe Leu Tyr Trp Ala Val Asp Ala
                195                 200                 205
Thr His Ala Pro Val Tyr Ala Ser Lys Pro Phe Leu Gly Thr Ser Gln
    210                 215                 220
Arg Gly Arg Tyr Gly Asp Ala Val Arg Glu Ile Asp Asp Ser Ile Gly
225                 230                 235                 240
Lys Ile Leu Glu Leu Leu Gln Asp Leu His Val Ala Asp Asn Thr Phe
                245                 250                 255
Val Phe Phe Thr Ser Asp Asn Gly Ala Ala Leu Ile Ser Ala Pro Glu
                260                 265                 270
Gln Gly Gly Ser Asn Gly Pro Phe Leu Cys Gly Lys Gln Thr Thr Phe
            275                 280                 285
Glu Gly Gly Met Arg Glu Pro Ala Leu Ala Trp Trp Pro Gly His Val
    290                 295                 300
Thr Ala Gly Gln Val Ser His Gln Leu Gly Ser Ile Met Asp Leu Phe
305                 310                 315                 320
Thr Thr Ser Leu Ala Leu Ala Gly Leu Thr Pro Ser Asp Arg Ala
            325                 330                 335
Ile Asp Gly Leu Asn Leu Leu Pro Thr Leu Leu Gln Gly Arg Leu Met
            340                 345                 350
Asp Arg Pro Ile Phe Tyr Tyr Arg Gly Asp Thr Leu Met Ala Ala Thr
    355                 360                 365
Leu Gly Gln His Lys Ala His Phe Trp Thr Trp Thr Asn Ser Trp Glu
    370                 375                 380
Asn Phe Arg Gln Gly Ile Asp Phe Cys Pro Gly Gln Asn Val Ser Gly
385                 390                 395                 400
Val Thr Thr His Asn Leu Glu Asp His Thr Lys Leu Pro Leu Ile Phe
                405                 410                 415
His Leu Gly Arg Asp Pro Gly Glu Arg Phe Pro Leu Ser Phe Ala Ser
            420                 425                 430
Ala Glu Tyr Gln Glu Ala Leu Ser Arg Ile Thr Ser Val Val Gln Gln
        435                 440                 445
His Gln Glu Ala Leu Val Pro Ala Gln Pro Leu Asn Val Cys Asn
        450                 455                 460
Trp Ala Val Met Asn Trp Ala Pro Gly Cys Glu Lys Leu Gly Lys
465                 470                 475                 480
Cys Leu Thr Pro Pro Glu Ser Ile Pro Lys Lys Cys Leu Trp Ser His
            485                 490                 495
```

<210> SEQ ID NO 3
<211> LENGTH: 20
<212> TYPE: PRT
<213> ORGANISM: Homo sapiens

<400> SEQUENCE: 3

Lys Leu Gly Lys Thr Leu Thr Pro Pro Glu Ser Ile Pro Lys Lys Thr
1               5                   10                  15

Leu Trp Ser His
            20

<210> SEQ ID NO 4
<211> LENGTH: 20
<212> TYPE: PRT
<213> ORGANISM: Homo sapiens

<400> SEQUENCE: 4

Gly Asp Leu Gly Val Tyr Gly Glu Pro Ser Arg Glu Thr Pro Asn Leu
1               5                   10                  15

Asp Arg Met Ala
            20

<210> SEQ ID NO 5
<211> LENGTH: 20
<212> TYPE: PRT
<213> ORGANISM: Homo sapiens

<400> SEQUENCE: 5

Asn Ala His Ala Arg Asn Ala Tyr Thr Pro Gln Glu Ile Val Gly Gly
1               5                   10                  15

Ile Pro Asp Ser
            20

<210> SEQ ID NO 6
<211> LENGTH: 20
<212> TYPE: PRT
<213> ORGANISM: Homo sapiens

<400> SEQUENCE: 6

Pro Asn Cys His Phe Gly Pro Tyr Asp Asn Lys Ala Arg Pro Asn Ile
1               5                   10                  15

Pro Val Tyr Arg
            20

<210> SEQ ID NO 7
<211> LENGTH: 20
<212> TYPE: PRT
<213> ORGANISM: Homo sapiens

<400> SEQUENCE: 7

Ala Ser Lys Pro Phe Leu Gly Thr Ser Gln Arg Gly Arg Tyr Gly Asp
1               5                   10                  15

Ala Val Arg Glu
            20

<210> SEQ ID NO 8
<211> LENGTH: 20
<212> TYPE: PRT
<213> ORGANISM: Homo sapiens

<400> SEQUENCE: 8

-continued

```
Ala Ala Leu Ile Ser Ala Pro Glu Gln Gly Gly Ser Asn Gly Pro Phe
1               5                   10                  15

Leu Thr Gly Lys
            20

<210> SEQ ID NO 9
<211> LENGTH: 20
<212> TYPE: PRT
<213> ORGANISM: Homo sapiens

<400> SEQUENCE: 9

Thr Thr Ser Leu Ala Leu Ala Gly Leu Thr Pro Pro Ser Asp Arg Ala
1               5                   10                  15

Ile Asp Gly Leu
            20

<210> SEQ ID NO 10
<211> LENGTH: 20
<212> TYPE: PRT
<213> ORGANISM: Homo sapiens

<400> SEQUENCE: 10

Phe Phe Leu Tyr Trp Ala Val Asp Ala Thr His Ala Pro Val Tyr Ala
1               5                   10                  15

Ser Lys Pro Phe
            20

<210> SEQ ID NO 11
<211> LENGTH: 20
<212> TYPE: PRT
<213> ORGANISM: Homo sapiens

<400> SEQUENCE: 11

Thr Gln Ile Tyr Leu Gln Glu Ala Leu Asp Phe Ile Lys Arg Gln Ala
1               5                   10                  15

Arg His His Pro
            20

<210> SEQ ID NO 12
<211> LENGTH: 20
<212> TYPE: PRT
<213> ORGANISM: Homo sapiens

<400> SEQUENCE: 12

Gln Gln His Gln Glu Ala Leu Val Pro Ala Gln Pro Gln Leu Asn Val
1               5                   10                  15

Thr Asn Trp Ala
            20
```

METHOD OF TREATING MUCOPOLYSACCHARIDOSIS TYPE IVA

GOVERNMENT SUPPORT CLAUSE

The invention was made with government support under award no. R03HD064749 from the Eunice Kennedy Shriver from the National Institute of Child Health & Human Development. The U.S. Government has certain rights in this invention.

CROSS REFERENCE TO RELATED APPLICATIONS

This application claims priority to U.S. patent application Ser. No. 13/760,907, filed on Feb. 6, 2013 (now abandoned), which claims priority to U.S. Provisional Patent Application Ser. No. 61/596,212, filed Feb. 7, 2012, and U.S. Provisional Patent Application Ser. No. 61/675,770 filed Jul. 25, 2012, each of which is incorporated by reference herein in its entirety.

FIELD

The invention relates to methods and compositions for inducing oral tolerance to enzymes used for enzyme replacement therapy in the treatment of subjects with lysosomal storages disorders. More specifically, the invention relates the identification of immunodominant peptides of N-acetyl-galactosamine-6-sulfatase and methods of use for inducing oral tolerance in subjects suffering from Mucopolysaccharidosis type IVA.

BACKGROUND

Mucopolysaccharidosis type IVA (MPS IVA) or Morquio A syndrome (MIM ID #253000) is an autosomal recessive disorder due to the deficiency of N-acetyl galactosamine-6-sulfate sulfatase (GALNS: E.C.3.1.6.4) that results in the lysosomal accumulation of keratan sulfate and chondroitin 6-sulfate. (Tomatsu et al. (2003) Hum Mol. Genet. 15; 12 (24):3349-58). In MPS IVA patients the accumulation leads to a chronic and progressive deterioration of affected cells, tissues and organs, with clinical manifestations that include bone abnormalities, dysostosis multiple, joint pathology with reduced mobility, organomegaly, coarse hair, respiratory pathology, cardiovascular disease and renal impairment (Tomatsu et al. (2003) Hum Mol Genet. 15; 12(24):3349-58; Futerman et al. (2004) Nat Rev Mol Cell Biol.; 5(7):554-65). The patient phenotypes vary from the classical form to milder forms. Phenotype-genotype correlation suggests that the severe phenotype depends mainly on the localization of the mutation in the protein (Sukegawa et al. (2000) Hum Mol Genet. 22; 9(9):1283-90)). As in other lysosomal storage disorders (LSDs), enzyme replacement therapy (ERT) is one of the treatments of choice. ERT is already available for some LSDs: Fabry's disease; Pompe's disease, MPS I, MPS II and MPS VI (Rohrbach et al. (2007) Drugs; 67(18):2697-716). GALNS deficiency has never been naturally reported in other species different to humans. The absence of an animal model has restricted the development of potential therapies such as ERT (Tomatsu et al. (2008) Hum Mol Genet. 15; 17(6):815-24). Three Morquio A mouse models have been developed (Tomatsu et al. (2003) Hum Mol Genet. 15; 12 (24):3349-58; Tomatsu et al. (2005) Hum Mol Genet. 15; 14(22):0321-35; Tomatsu (2007) Mol Genet Metab. 91(3):251-8) and preclinical studies of ERT in MPS IVA mice have been accomplished, providing critical information for the design of ERT in Morquio A patients (Tomatsu et al. (2008) Hum Mol Genet. 15; 17(6):815-24).

Immune response to the injected enzyme has been recognized as the main limitation during ERT in most of the patients and animal models (Ponder (2008) J Clin Invest. August; 118(8):2686-9; Brooks et al. (2003) Trends Mol Med. 9(10):450-3). Antibodies to the infused enzyme can cause hypersensitivity reactions, resistance to the treatment and glomerulonephritis due to the depositions of immune-complexes in kidney (Matzner (2008) J Mol Med. 86(4): 433-42). To diminish the immune response in these patients, strategies for immunosuppression have been tested. Although non-specific immune suppressive protocols have demonstrated good results in obtaining tolerance to the infused protein, the well-established side-effects in those patients can be an issue in their quality of life (Brooks et al. (2003) Trends Mol Med. 9 (10):450-3; Kakkis et al. (2004) Proc Natl Acad Sci USA. 20; 101(3):829-34; Brady et al. (1997) Pediatrics 100(6):E11; Bluestone et al. (2010) Nat Rev Immunol. 2010; 10(11):797-803). The new challenge is to replace chronic treatments of immunosuppression and their associated toxicities with new therapies that induce specific immune tolerance in a safe manner. Id. The Inventors have identified the most immunodominant regions in GALNS protein. These regions may be used to develop a peptide-based immunotherapy to induce specific tolerance to GALNS used in ERT. A peptide based immunotherapy may also be more cost effective. The identification of immunodominant peptides will allow the establishment of a peptide-based immunotherapy for Morquio A syndrome which may be applied to other LSDs in which the immune response hinders the development of ERT.

Thus, immune response to ERT in LSDs are widely reported and present one of the major complications of treatments (Brooks, Kakavanos et al. 2003; Matzner, Matthes et al. 2008). This is due to different factors such as the nature of the infused protein, genetic background of the patient, route of enzyme administration, frequency, and dose of treatment, structural differences between the infused and the defective protein and environmental factors (Brooks 1999; Brooks, Kakavanos et al. 2003). To induce immune tolerance, several immunosuppressive protocols have been tried experimentally (Kakkis, Lester et al. 2004; Dickson, Peinovich et al. 2008; Joseph, Munroe et al. 2008) and are under development. However to date their effectiveness is not clear.

Alternatively, for suppressing the immune response to ERT without adverse effects, the inventors have devised a protocol for administering immunodominant peptides to induce oral tolerance. Oral tolerance is defined as the specific suppression of cellular and humoral immune responses to an antigen prior its administration by the oral route in order to obtain peripheral tolerance. It is a natural mechanism in which exogenous antigens gain access to the body by oral route as internal components. As exemplified herein, the inventors discovered that oral tolerance may be induced in a subject by the oral administration of a target enzyme, or immunodominant peptides of a target enzyme, prior to commencing enzyme replacement therapy. Induction of oral tolerance has been tested in human autoimmune diseases including multiple sclerosis (MS), uveitis, rheumatoid arthritis (RA), diabetes, and allergies. After the oral tolerance is induced, the cellular response is observed by the increased regulatory T cell population (Th3, Tr1, and CD4+ CD25+T Foxp3+cells) while production of cytokines related to oral tolerance such as TGF-β and IL-10 are up-regulated.

The Inventors have filled a long felt need by identifying peptide sequences capable of inducing immune tolerance to GALNS in GALNS deficient subjects when administered through an oral protocol. It is expected that the method used in identifying these peptides and establishing oral tolerance in MPS IVA subjects may be extended to enhance other ERT treatments especially those used in treating other LSDs.

SUMMARY

Isolated immunodominant peptides of N-acetylgalactosamine-6-sulfatase, and fragments thereof.

A method of inducing oral tolerance to N-acetyl galactosamine-6-sulfate sulfatase (GALNS) in a subject suffering from mucopolysaccharidosis type IVA comprising, administering by oral ingestion, one or more isolated immunodominant peptides of GALNS.

A method of inducing oral tolerance to peptides of N-acetylgalactosamine-6-sulfatase (GALNS) in a subject suffering from mucopolysaccharidosis type IVA comprising, administering by oral ingestion, GALNS, or one or more fragments of GALNS wherein the fragment comprises one or more immunodominant peptides.

A method of determining immunodominant peptides of target enzymes administered to subjects during enzyme replacement therapy.

A method for treating mucopolysaccharidosis type IVA in a subject suffering from mucopolysaccharidosis type IVA, the method comprising: administering to the subject an effective amount of a polypeptide selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and combinations thereof.

Reference to Color Figures

The application file contains at least one figure executed in color. Copies of this patent application publication with color photographs will be provided by the Office upon request and payment of the necessary fee.

DESCRIPTION OF THE FIGURES

FIG. 1 shows splenocyte proliferation after GALNS (150 μg/ml) or peptide (100 μg/ml) in vitro stimulation of MKC mice treated by ERT (in red) or PBS (in blue). CPM (Counts per minute). Blue arrows show peptides 4, 8 and 10.

FIG. 2 shows IFN-γ secretion after splenocytes in vitro stimulation with GALNS (150 μg/ml) or peptide (100 μg/ml) in MKC mice treated by ERT-250 U/g or 1000 U/g (in green) or PBS (in blue). Blue arrows show peptides 4, 8 and 10.

FIG. 3 shows IL-5 secretion after splenocytes in vitro stimulation with GALNS (150 μg/ml) or peptide (100 μg/ml) in MKC mice treated by ERT-250 U/g or 1000 U/g (in orange) or PBS (in blue). Blue arrows show peptides 4, 8 and 10.

FIG. 4 shows the relationship between the number of weeks of infusion (x-axis) and splenocyte proliferation (y-axis) after in vitro GALNS or peptide (4, 8, and 10) stimulation.

FIG. 5. Evaluation of immunodominant peptides. Morquio A mice (MKC, C2, or MTol) or WT mice were treated by ERT. One week after the last infusion, splenocytes were stimulated with individual peptides or GALNS for cellular response determination (proliferation and cytokines secretion).

FIG. 6. Evaluation of oral tolerance induction. MKC mice were fed with peptide I10 or GALNS at three different concentrations. One week after the last oral dose, mice received 16 weekly i.v. infusions of GALNS or PBS. Ten days after the last infusion, splenocytes were stimulated with GALNS for cellular response determination (proliferation and cytokines secretion). Humoral response was evaluated in plasma samples.

FIG. 7. Oral administration protocol for the induction of oral tolerance followed by enzyme replacement therapy (ERT).

FIG. 8. Differences in proliferation after splenocytes in vitro stimulation with GALNS (150 μg/ml) or peptides (100 μg/ml). MKC mice were treated with A. 16 i.v. weekly infusions or B. 22 i.v. weekly infusions of human GALNS (filled bars) or PBS (open bars). Each bar represents the average of two different mice. The background levels from unstimulated cells were subtracted. *$p<0.05$; **$p<0.01$ (statistically significant difference between treated and untreated mice). †$p<0.05$ (statistically significant difference between 16 i.v. and 22 i.v. infusion treated mice).

FIG. 9. Relationship between number of infusions and levels of splenocyte proliferation. MKC mice were treated with 16, 22 or 24 i.v. weekly infusions with human GALNS. Splenocytes were stimulated in vitro with human GALNS (150 μg/ml), or peptide 4, 8 or 10 (100 μg/ml). Each point represents the average of two MKC mice treated by ERT.

FIG. 10. Cytokine secretion after splenocytes in vitro stimulation with GALNS (150 ug/ml) or peptide (100 μg/ml). Secretion levels of A. IFN-γ. B. IL-4. C. IL-5. D. IL-13. MKC mice were treated with 16 i.v. infusions with human GALNS (filled bars) or PBS (open bars). Each bar represents the average of three different mice. The background levels from unstimulated cells were subtracted. *$p<0.05$; $p<0.01$; *$p<0.001$.

FIG. 11. Humoral response against human GALNS used for ERT in Morquio A mouse models and WT mice. Tolerant mouse model (MTol). Knock-out mouse model (MKC). Knock-in mouse model (C2). Wild type mice (WT). Mice were treated with 16 i.v. infusions with human GALNS (filled bars) or PBS (open bars). **$p=0.003$.

FIG. 12. Comparison of splenocytes proliferation levels after in vitro stimulation among the Morquio A mouse models and WT mice. Knock-out mouse model (MKC), Knock-in mouse model (C2), Wild type mice (WT) and Tolerant mouse model (MTol) were treated with 16 weekly i.v. infusions of human GALNS (filled bars) or PBS (open bars). One week after last infusion, splenocytes were stimulated with A. Peptides C4 (100 μg/ml). B. Peptides E8 (100 μg/ml). C. Peptides I10 (100 μg/ml). D. GALNS (150 μg/ml). The background levels from unstimulated cells were subtracted. Each error bar denotes triplicates. *$p<0.05$; **$p<0.01$ (statistically significant difference between treated and untreated mice, same strain). § $p<0.05$ (statistically significant difference between treated mice, different strain).

FIG. 13. Comparison of IFN-γ secretion levels after in vitro stimulation among the MPS IVA mouse models and WT mice. Knock-out mouse model (MKC), Knock-in mouse model (C2), Wild type mice (WT) and Tolerant mouse model (MTol) were treated with 16 weekly i.v. infusions of human GALNS (filled bars) or PBS (open bars). One week after last infusion, splenocytes were stimulated with A. Peptide C4 (100 μg/ml), B. Peptide E8 (100 μg/ml), C. Peptide I10 (100 μg/ml) or D. GALNS (150 μg/ml). The background levels from unstimulated cells were subtracted. *$p<0.05$; $p<0.01$; *$p<0.001$ (statistically significant difference between treated and untreated mice, same strain). § $p<0.05$; §§ $p<0.01$ (statistically significant difference between treated mice, different strain).

FIG. 14. Comparison of IL-4 secretion levels after in vitro stimulation among the MPS IVA mice models and WT mice. Knock-out model (MKC), Missense model (C2), Wild type mice (WT) and Tolerant model (MTol) mice were treated with 16 weekly i.v. infusions of human GALNS (black to gray bars) or PBS (open bars). One week after last infusion, splenocytes were stimulated with A. Peptide C4 (100 µg/ml), B. Peptide E8 (100 µg/ml), C. Peptide I10 (100 µg/ml) or D. GALNS (150 µg/ml). The background levels from unstimulated cells were subtracted. *$p<0.05$; $p<0.01$; *$p<0.001$ (statistically significant difference between treated and untreated mice, same strain).

Figure 15:
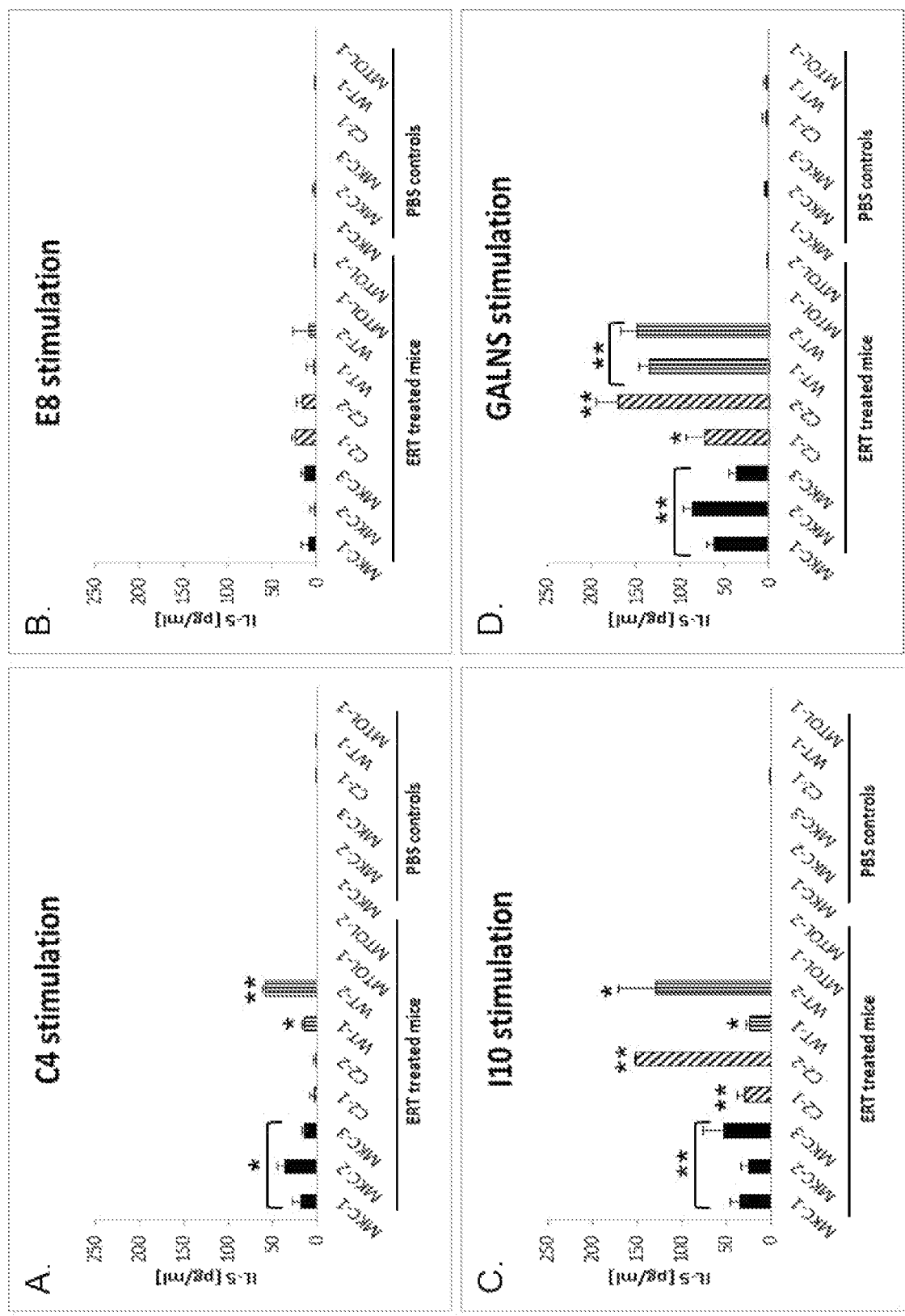

FIG. 15. Comparison of IL-5 secretion levels after in vitro stimulation among the MPS IVA mouse models and WT mice. Knock-out mouse model (MKC), Knock-in mouse model (C2), Wild type mice (WT) and Tolerant mouse model (MTol) were treated with 16 weekly i.v. infusions of human GALNS (filled bars) or PBS (open bars). One week after last infusion, splenocytes were stimulated with A. Peptide C4 (100 µg/ml), B. Peptide E8 (100 µg/ml), C. Peptide I10 (100 µg/ml) or D. GALNS (150 µg/ml). The background levels from unstimulated cells were subtracted. *$p<0.05$; **$p<0.01$ (statistically significant difference between treated and untreated mice, same strain).

Figure 16:
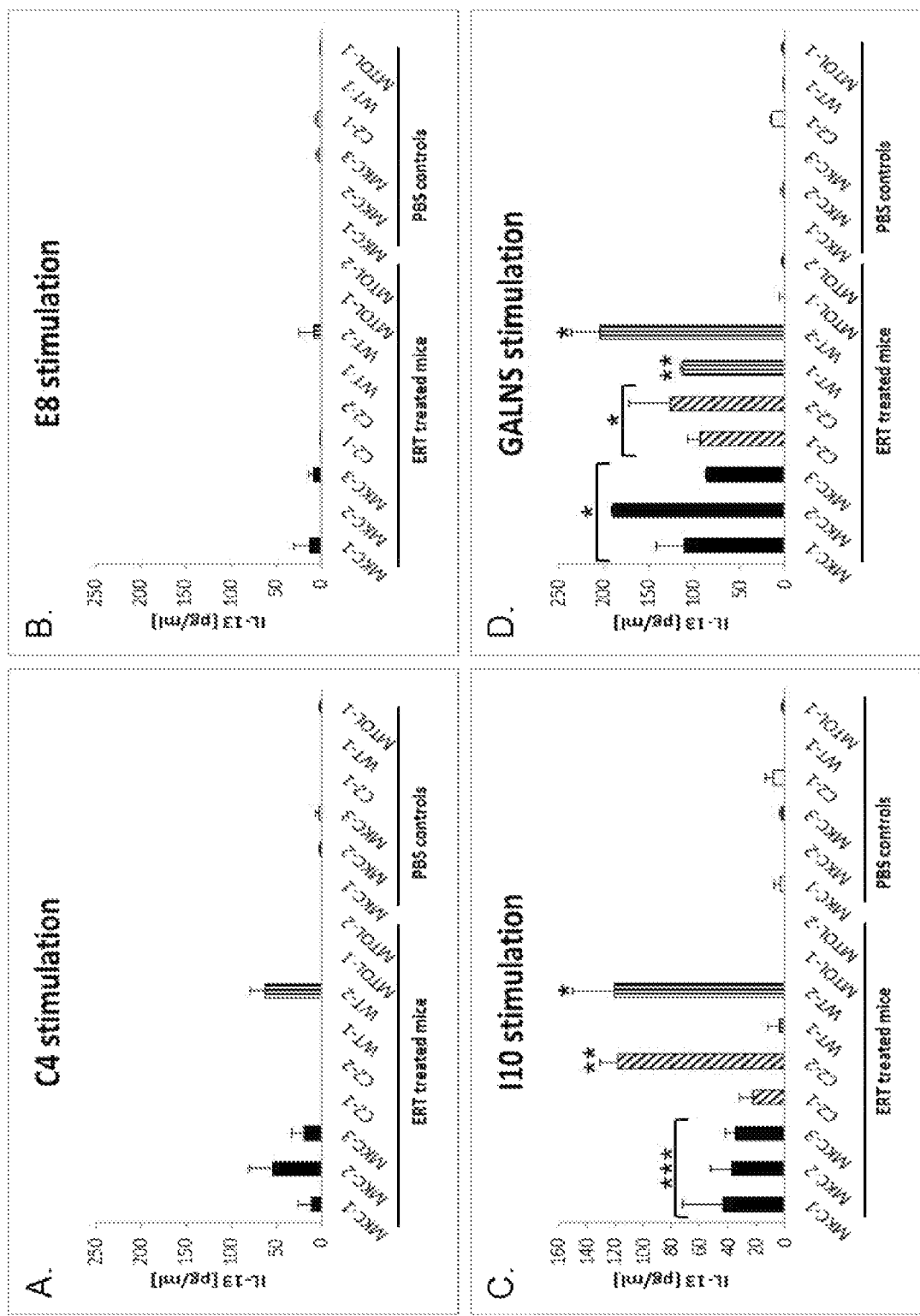

FIG. 16. Comparison of IL-13 secretion levels after in vitro stimulation among the MPS IVA mouse models and WT mice. Knock-out mouse model (MKC), Knock-in mouse model (C2), Wild type mice (WT) and Tolerant mouse model (MTol) were treated with 16 weekly i.v. infusions of human GALNS (filled bars) or PBS (open bars). One week after last infusion, splenocytes were stimulated with A. Peptide C4 (100 µg/ml), B. Peptide E8 (100 µg/ml), C. Peptide I10 (100 µg/ml) or D. GALNS (150 µg/ml). The background levels from unstimulated cells were subtracted. *$p<0.05$; **$p<0.01$ (statistically significant difference between treated and untreated mice, same strain).

Figure 17:
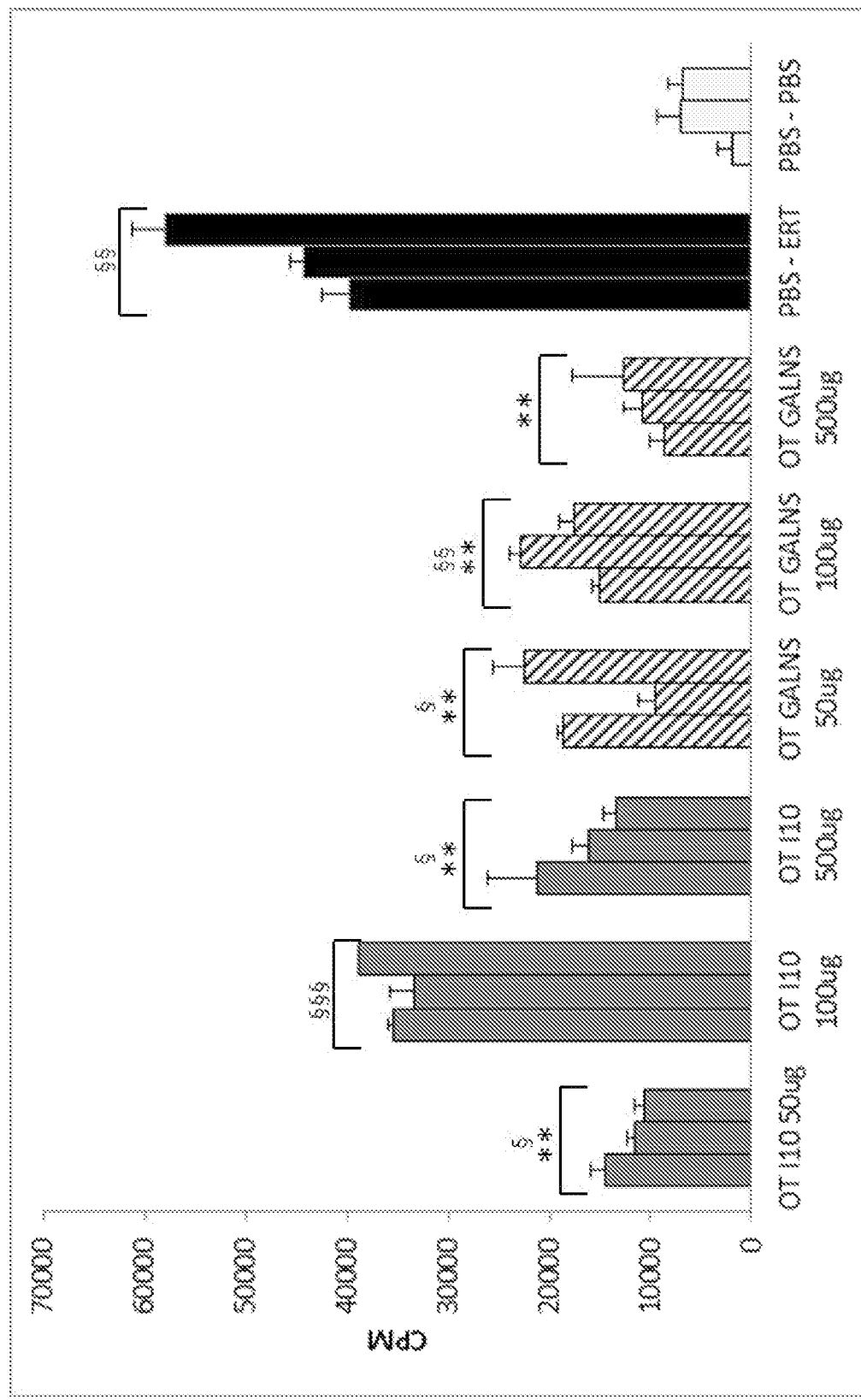

FIG. 17. Effect of tolerance induction on splenocytes proliferation after in vitro stimulation with GALNS. Oral tolerance was induced by feeding MKC mice with 50, 100 or 500 µg of peptide I10 (gray bars) or GALNS enzyme (striped bars). Control groups were fed with PBS (black and open bars). One week after the last oral dose, mice received 16 weekly i.v. infusions of human GALNS (filled bars) or PBS (open bars). The background levels from unstimulated cells were subtracted. Each error bar denotes triplicates. *$p<0.05$; **$p<0.01$ (statistically significant difference between tolerized and non-tolerized (PBS-ERT) mice). § $p<0.05$; §§ $p<0.01$; § § § $p<0.001$ (statistically significant difference between ERT treated mice and untreated (PBS-PBS) mice).

Figure 18:
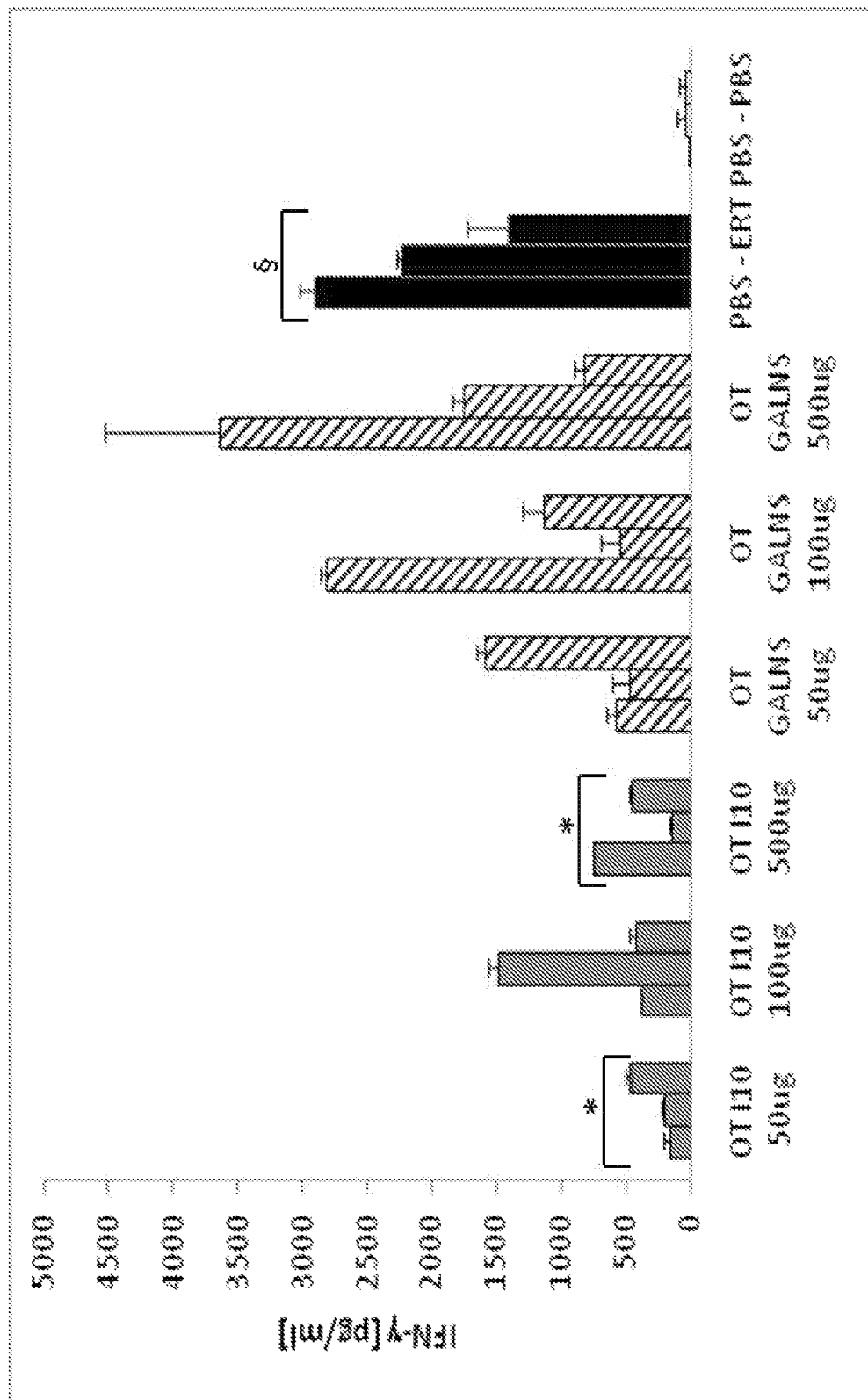

FIG. 18. Effect of tolerance induction on IFN-γ secretion after in vitro stimulation with GALNS. Oral tolerance was induced by feeding MKC mice with 50, 100 or 500 µg of peptide I10 (gray bars) or GALNS enzyme (striped bars). Control groups were fed with PBS (black and open bars). One week after the last oral dose, mice received 16 weekly i.v. infusions of human GALNS (filled bars) or PBS (open bars). The background levels from unstimulated cells were subtracted. Each error bar denotes duplicates. *$p<0.05$ (statistically significant difference between tolerized and non-tolerized (PBS-ERT) mice). § $p<0.05$ (statistically significant difference between ERT treated mice and untreated (PBS-PBS) mice).

Figure 19:
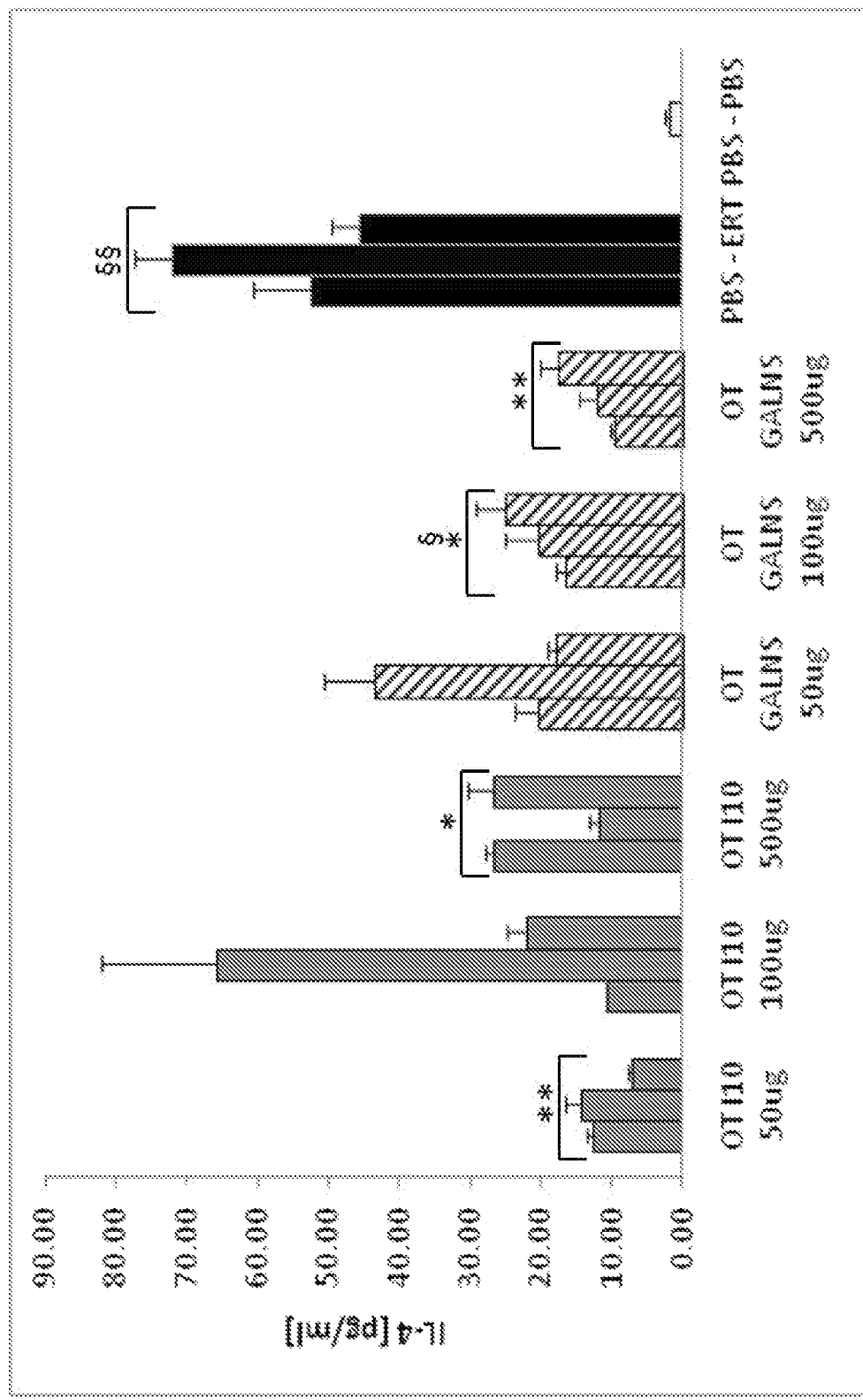

FIG. 19. Effect of tolerance induction on IL-4 secretion after in vitro stimulation with GALNS. Oral tolerance was induced by feeding MKC mice with 50, 100 or 500 g of peptide I10 (gray bars) or GALNS enzyme (striped bars). Control groups were fed with PBS (black and open bars). One week after the last oral dose, mice received 16 weekly i.v. infusions of human GALNS (filled bars) or PBS (open bars). The background levels from unstimulated cells were subtracted. Each error bar denotes duplicates. *$p<0.05$; **$p<0.01$ (statistically significant difference between tolerized and non-tolerized (PBS-ERT) mice). § $p<0.05$; §§ $p<0.01$ (statistically significant difference between ERT treated mice and untreated (PBS-PBS) mice).

Figure 20:
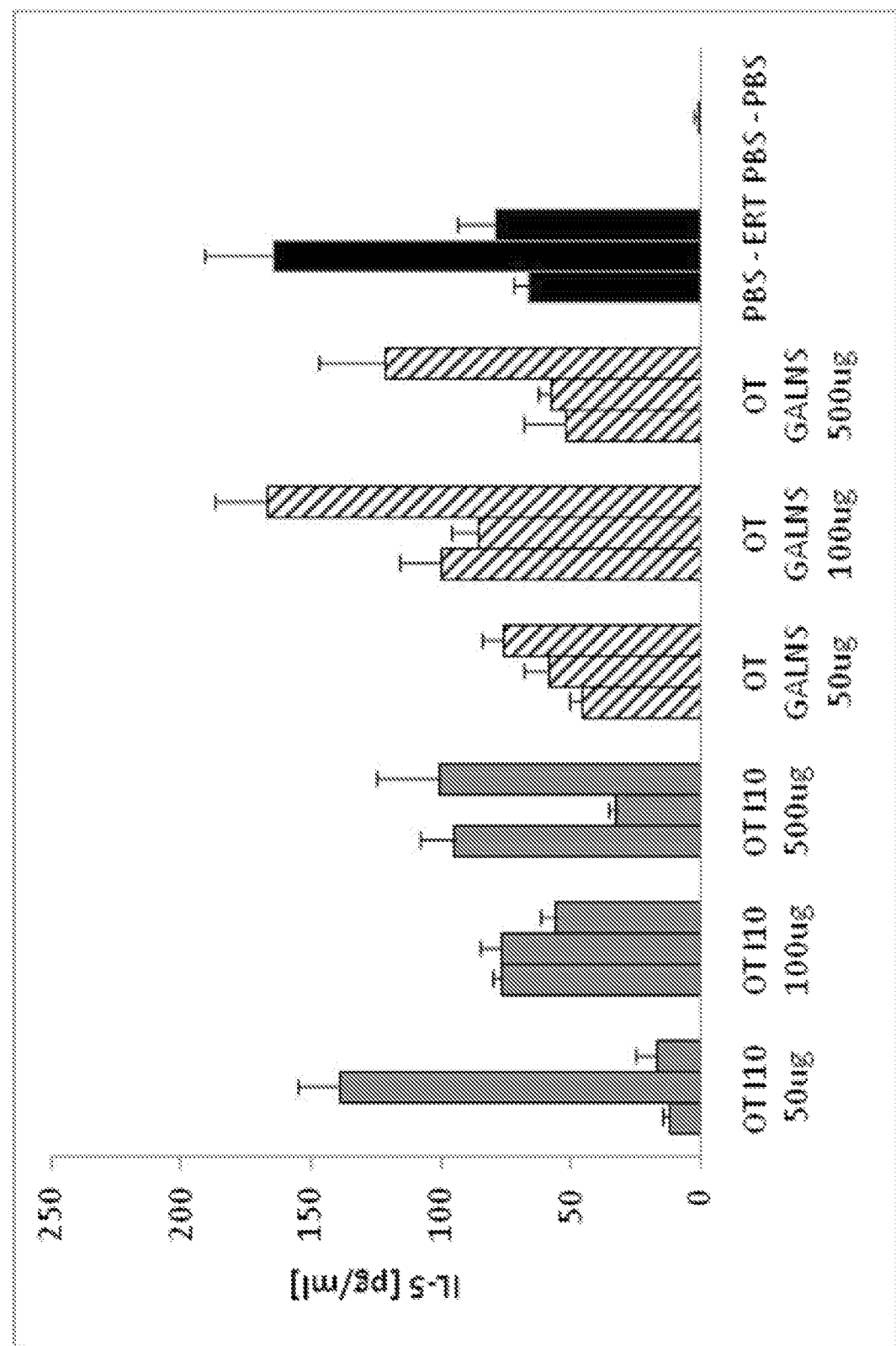

FIG. 20. Effect of tolerance induction on IL-5 secretion after in vitro stimulation with GALNS. Oral tolerance was induced by feeding MKC mice with 50, 100 or 500 µg of peptide I10 (gray bars) or GALNS enzyme (striped bars). Control groups were fed with PBS (black and open bars). One week after the last oral dose, mice received 16 weekly i.v. infusions of human GALNS (filled bars) or PBS (open bars). The background levels from unstimulated cells were subtracted. Each error bar denotes duplicates.

Figure 21:
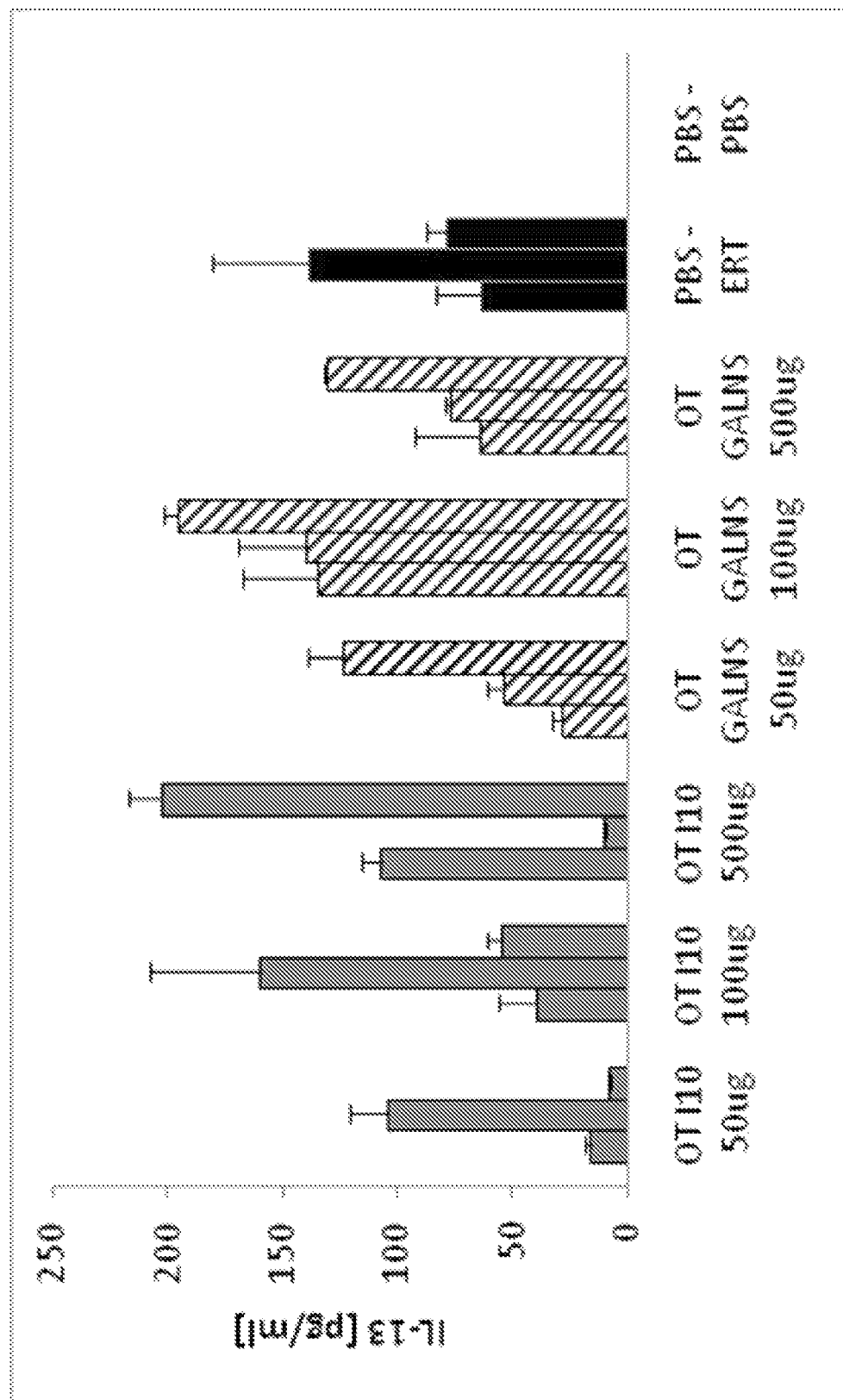

FIG. 21. Effect of tolerance induction on IL-13 secretion after in vitro stimulation with GALNS. Oral tolerance was induced by feeding MKC mice with 50, 100 or 500 µg of peptide I10 (gray bars) or GALNS enzyme (striped bars). Control groups were fed with PBS (black and open bars). One week after the last oral dose, mice received 16 weekly i.v. infusions of human GALNS (filled bars) or PBS (open bars). The background levels from unstimulated cells were subtracted. Each error bar denotes duplicates.

Figure 22:
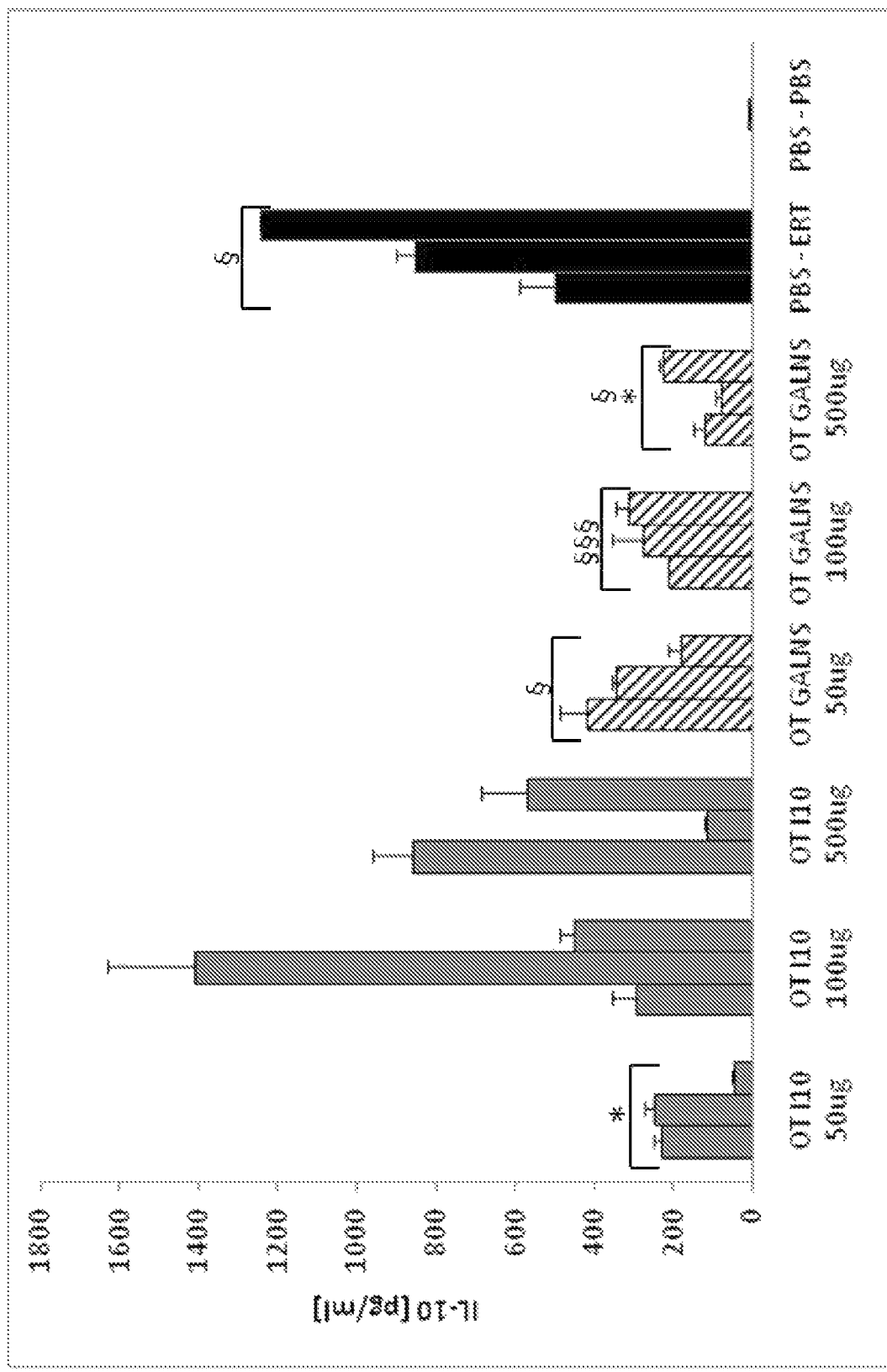

FIG. 22. Effect of tolerance induction on IL-10 secretion after in vitro stimulation with GALNS. Oral tolerance was induced by feeding MKC mice with 50, 100 or 500 µg of peptide I10 (gray bars) or GALNS enzyme (striped bars). Control groups were fed with PBS (black and open bars). One week after the last oral dose, mice received 16 weekly i.v. infusions of human GALNS (filled bars) or PBS (open bars). The background levels from unstimulated cells were subtracted. Each error bar denotes duplicates. *$p<0.05$ (statistically significant difference between tolerized and non-tolerized (PBS-ERT) mice). § $p<0.05$; § § § $p<0.001$ (statistically significant difference between ERT treated mice and untreated (PBS-PBS) mice).

Figure 23:
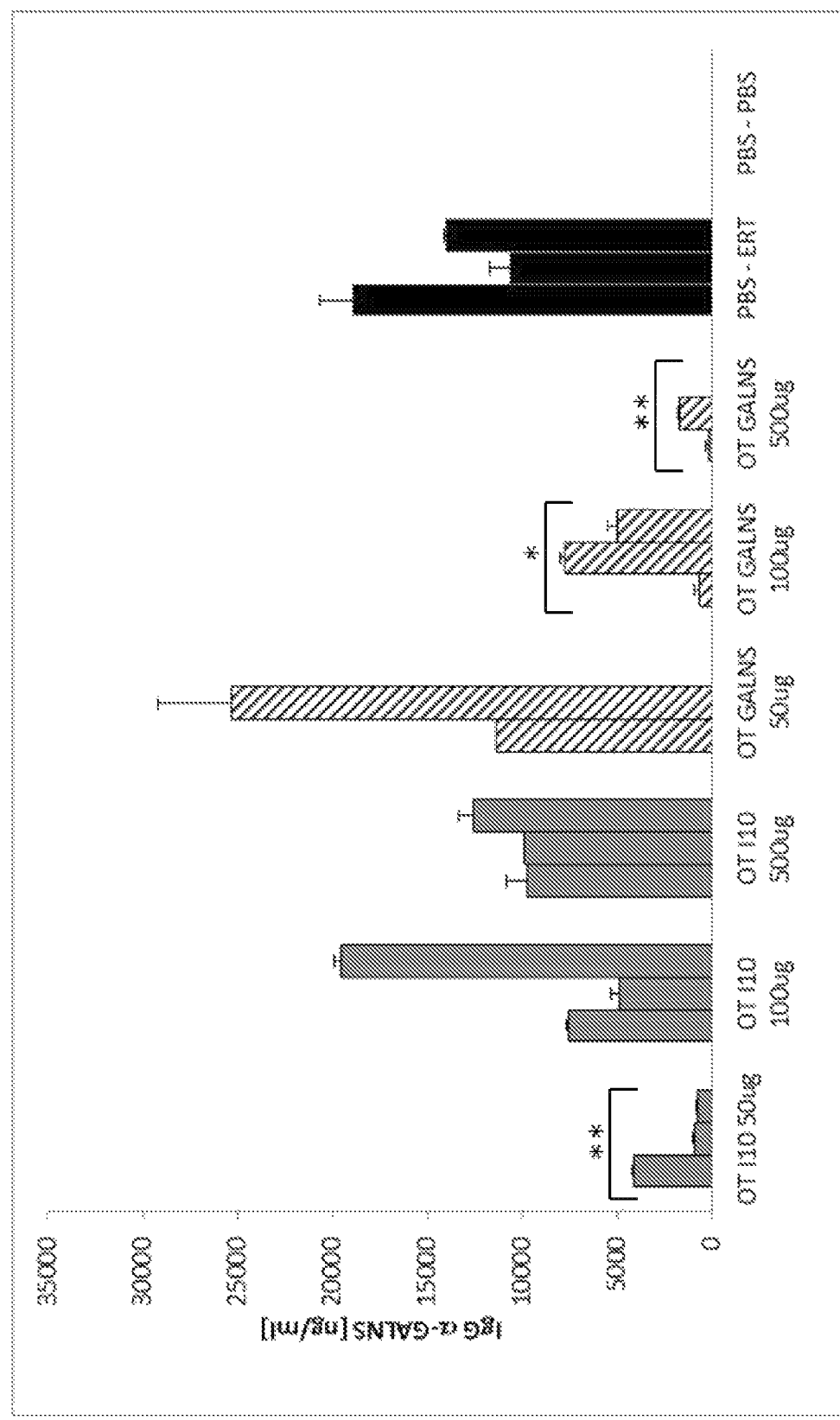

FIG. 23. GALNS specific IgG levels in mice treated by ERT (16 i.v. infusions). Oral tolerance was induced by feeding MKC mice with 50, 100 or 500 µg of peptide I10 (gray bars) or GALNS enzyme (striped bars). Control groups were fed with PBS (black and open bars). One week after the last oral dose, mice received 16 weekly i.v. infusions of human GALNS (filled bars) or PBS (open bars). IgG plasma levels were determined in the samples obtained one week after the last infusion. Each error bar denotes duplicates. *$p<0.05$; **$p<0.01$ (statistically significant difference between tolerized and non-tolerized (PBS-ERT) mice).

Figure 24:
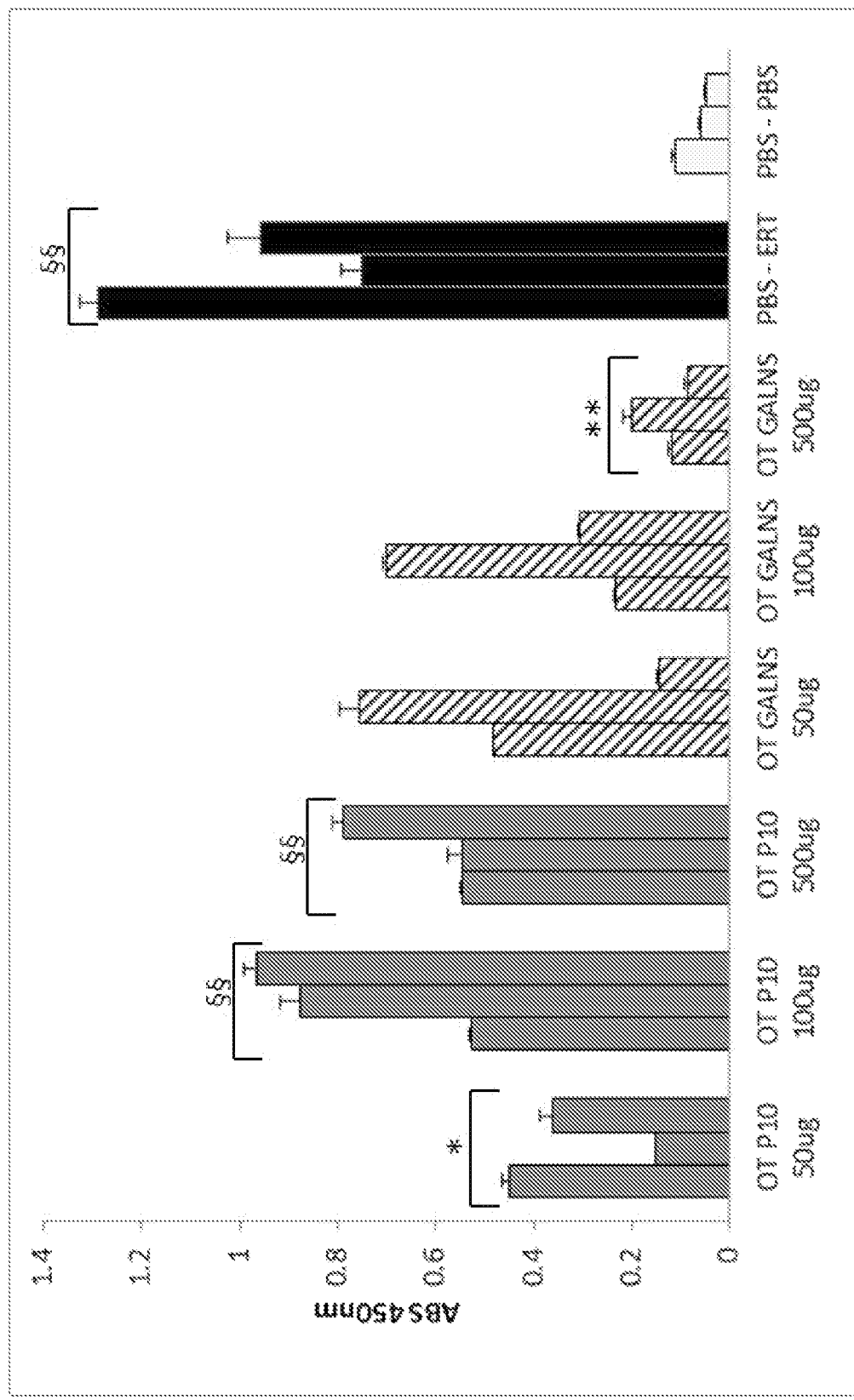

FIG. 24. GALNS specific IgE levels in mice treated by ERT (16 i.v. infusions). Oral tolerance was induced by feeding MKC mice with 50, 100 or 500 µg of peptide I10 (gray bars) or GALNS enzyme (striped bars). Control groups were fed with PBS (black and open bars). One week after the last oral dose, mice received 16 weekly i.v. infusions of human GALNS (filled bars) or PBS (open bars). IgE plasma levels were determined in the samples obtained one week after the last infusion. Each error bar denotes duplicates. *$p<0.05$; **$p<0.01$ (statistically significant difference between tolerized and non-tolerized (PBS-ERT) mice). § $p<0.05$; § § $p<0.01$; § § § $p<0.001$ (statistically significant difference between ERT treated mice and untreated (PBS-PBS) control).

Figure 25:
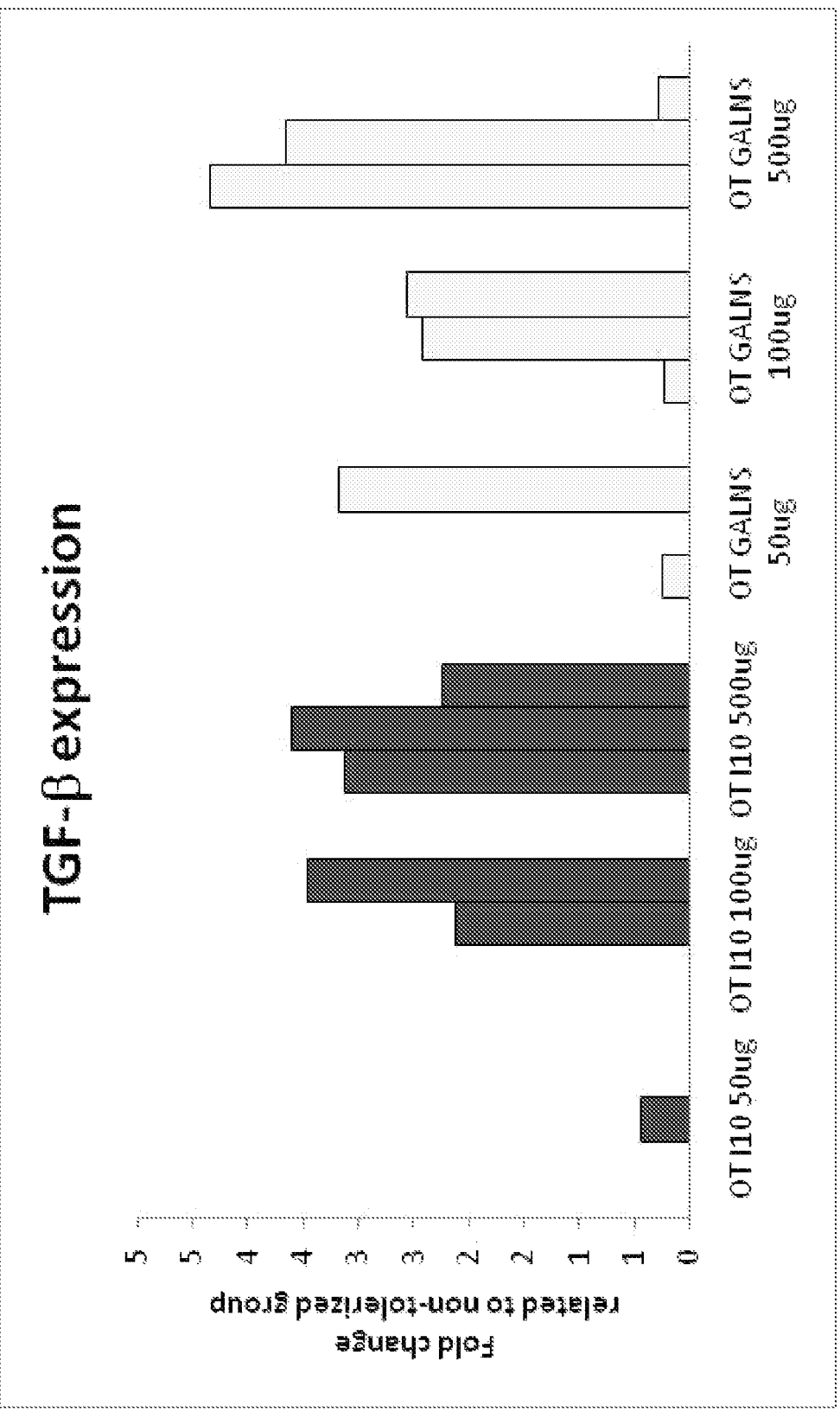

FIG. 25. Up-regulation of TGF-β expression after induction of tolerance in mice PP. Oral tolerance was induced by feeding MKC mice with 50, 100 or 500 μg of peptide I10 (filled bars) or GALNS enzyme (open bars). Control groups were fed with PBS. One week after the last oral dose, mice received 16 weekly i.v. infusions of human GALNS. mRNA of PP was extracted and the TGF-β expression was evaluated by real-time PCR. The fold change in expression was related to the values of non-tolerized group. GAPDH was using as a housekeeping gene for the data normalization.

Figure 26:
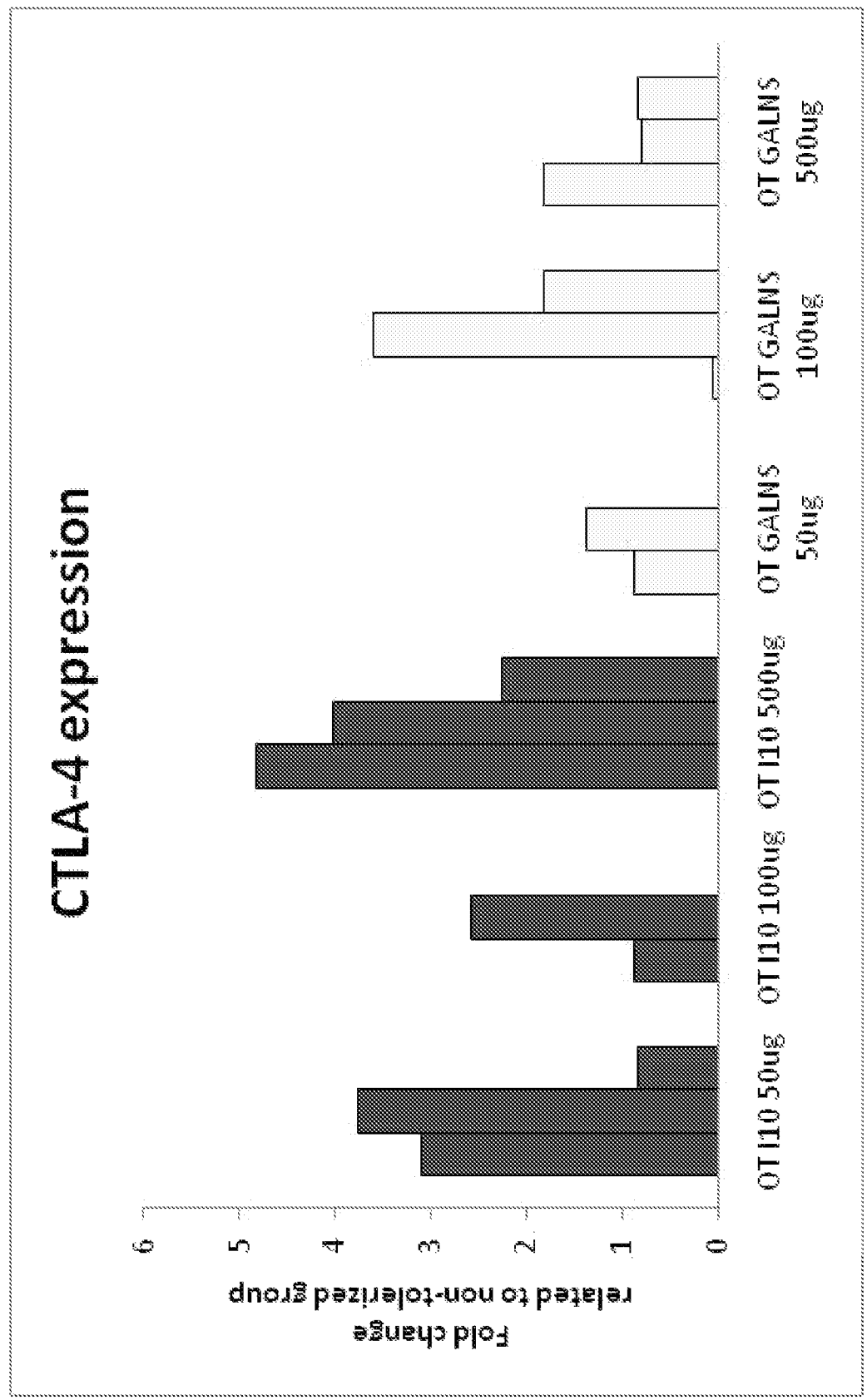

FIG. 26. Up-regulation of CTLA-4 expression after induction of tolerance in mice PP. Oral tolerance was induced by feeding MKC mice with 50, 100 or 500 μg of peptide I10 (filled bars) or GALNS enzyme (open bars). Control groups were fed with PBS. One week after the last oral dose, mice received 16 weekly i.v. infusions of human GALNS. mRNA of PP was extracted and the CTLA-4 expression was evaluated by real-time PCR. The fold change in expression was related to the values of non-tolerized group. GAPDH was using as a housekeeping gene for the data normalization.

Figure 27:
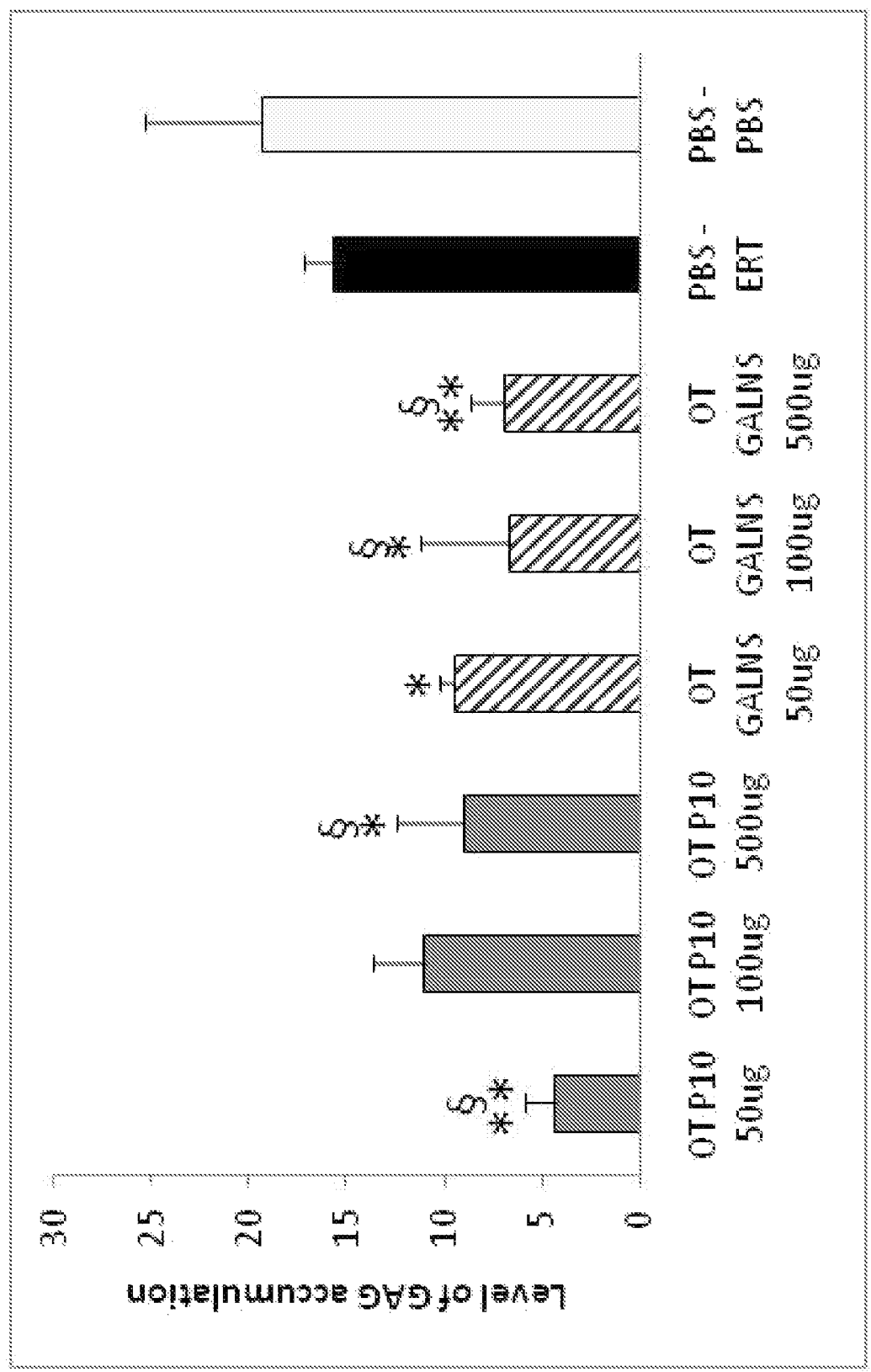

FIG. 27. Determination of GAGs accumulation after oral tolerance induction to GALNS. Oral tolerance was induced by feeding MKC mice with 50, 100 or 500 μg of peptide I10 (gray bars) or GALNS enzyme (striped bars). Control groups were fed with PBS (black and open bars). One week after the last oral dose, mice received 16 weekly i.v. infusions of human GALNS (filled bars) or PBS (open bars). GAGs accumulation was evaluated in liver samples. Each error bar denotes the values of accumulation in three mice per group. *$p<0.05$; **$p<0.01$ (statistically significant difference between tolerized and non-tolerized (PBS-ERT) mice). § $p<0.05$ (statistically significant difference between ERT treated mice and untreated (PBS-PBS) control).

Figure 28:
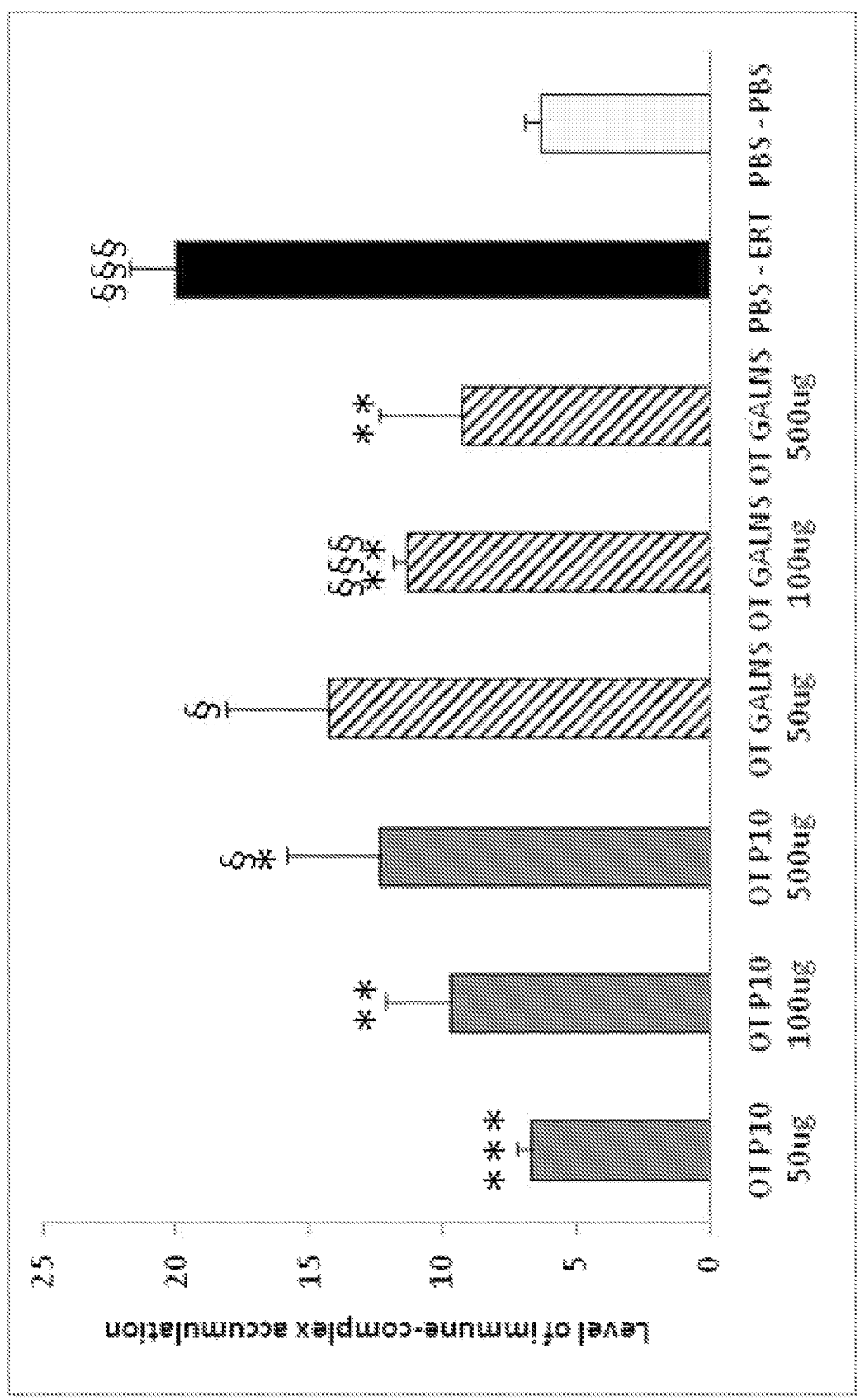

FIG. 28. Determination of Immune-complex deposits in kidney after oral tolerance induction to GALNS. Oral tolerance was induced by feeding MKC mice with 50, 100 or 500 μg of peptide I10 (gray bars) or GALNS enzyme (striped bars). Control groups were fed with PBS (black and open bars). One week after the last oral dose, mice received 16 weekly i.v. infusions of human GALNS (filled bars) or PBS (open bars). Immune-complex deposits were evaluated in kidney samples. Each error bar denotes the values of accumulation in three mice per group. *$p<0.05$; $p<0.01$; *$p<0.001$ (statistically significant difference between tolerized and non-tolerized (PBS-ERT) mice). § $p<0.05$; § § § $p<0.001$ (statistically significant difference between ERT treated mice and untreated (PBS-PBS) control).

Figure 29:
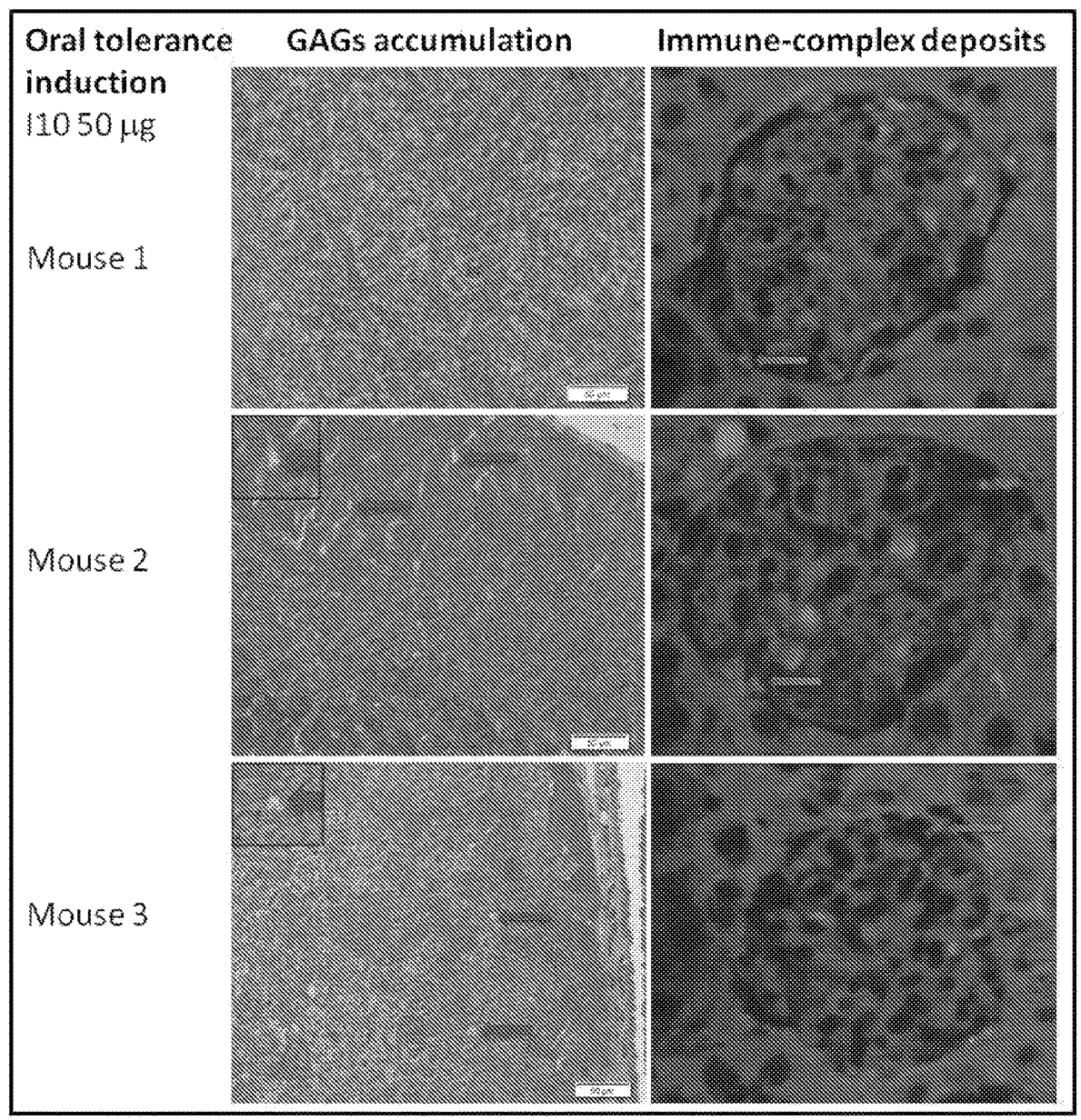

FIG. 29. Correlation between GAGs accumulation in liver and Immune-complex deposits in kidney after oral tolerance induction to GALNS. Oral tolerance was induced by feeding MKC mice with peptide I10 50 μg. One week after the last oral dose, mice received 16 weekly i.v. infusions of human GALNS. GAGs accumulation was evaluated in liver samples by light microscopy (40×) and immune-complex deposits were evaluated in kidney samples by fluorescence (100×).

Figure 30:
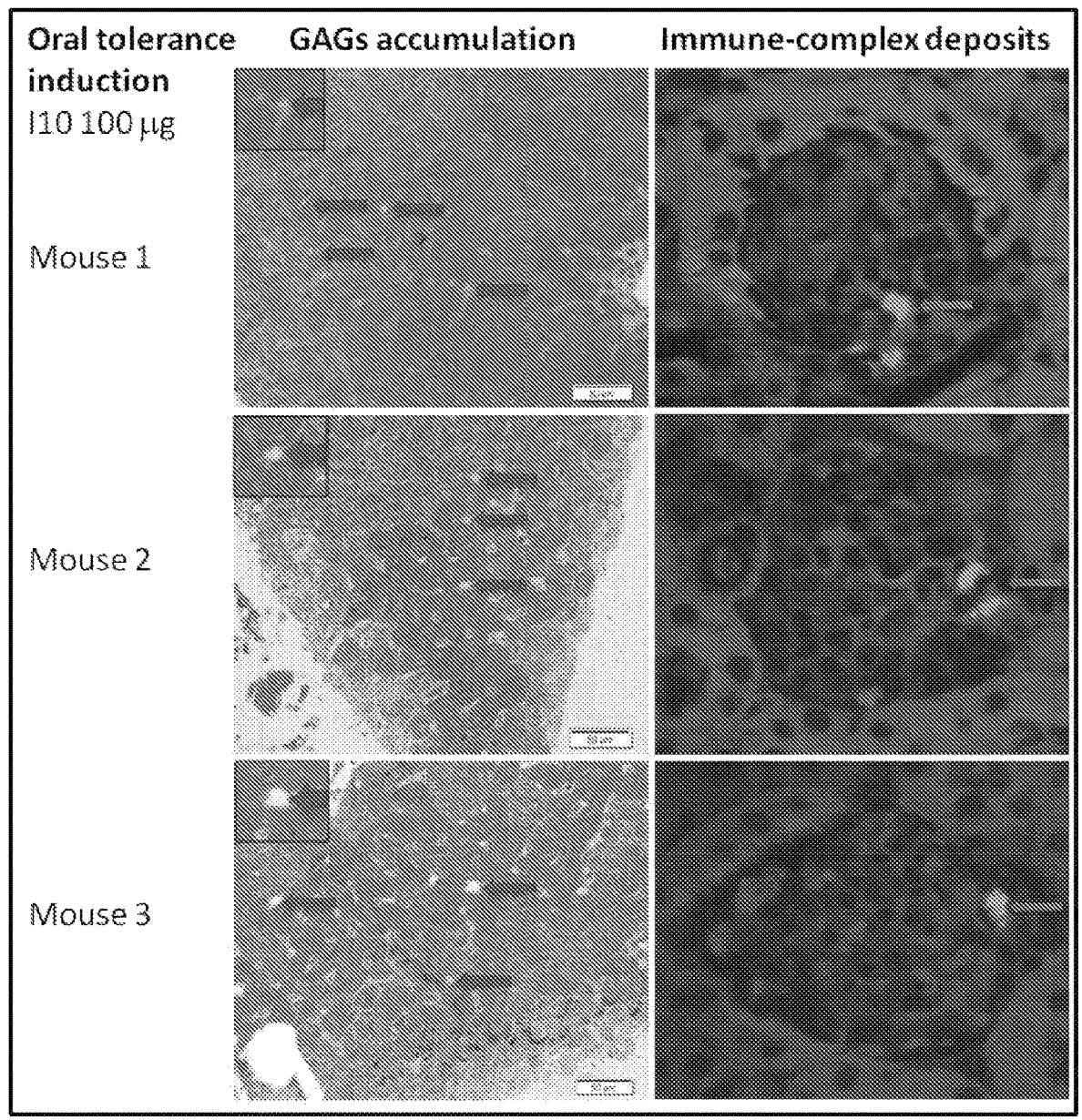

FIG. 30. Correlation between GAGs accumulation in liver and Immune-complex deposits in kidney after oral tolerance induction to GALNS. Oral tolerance was induced by feeding MKC mice with peptide I10 100 μg. One week after the last oral dose, mice received 16 weekly i.v. infusions of human GALNS. GAGs accumulation was evaluated in liver samples by light microscopy (40×) and immune-complex deposits were evaluated in kidney samples by fluorescence (100×).

Figure 31:
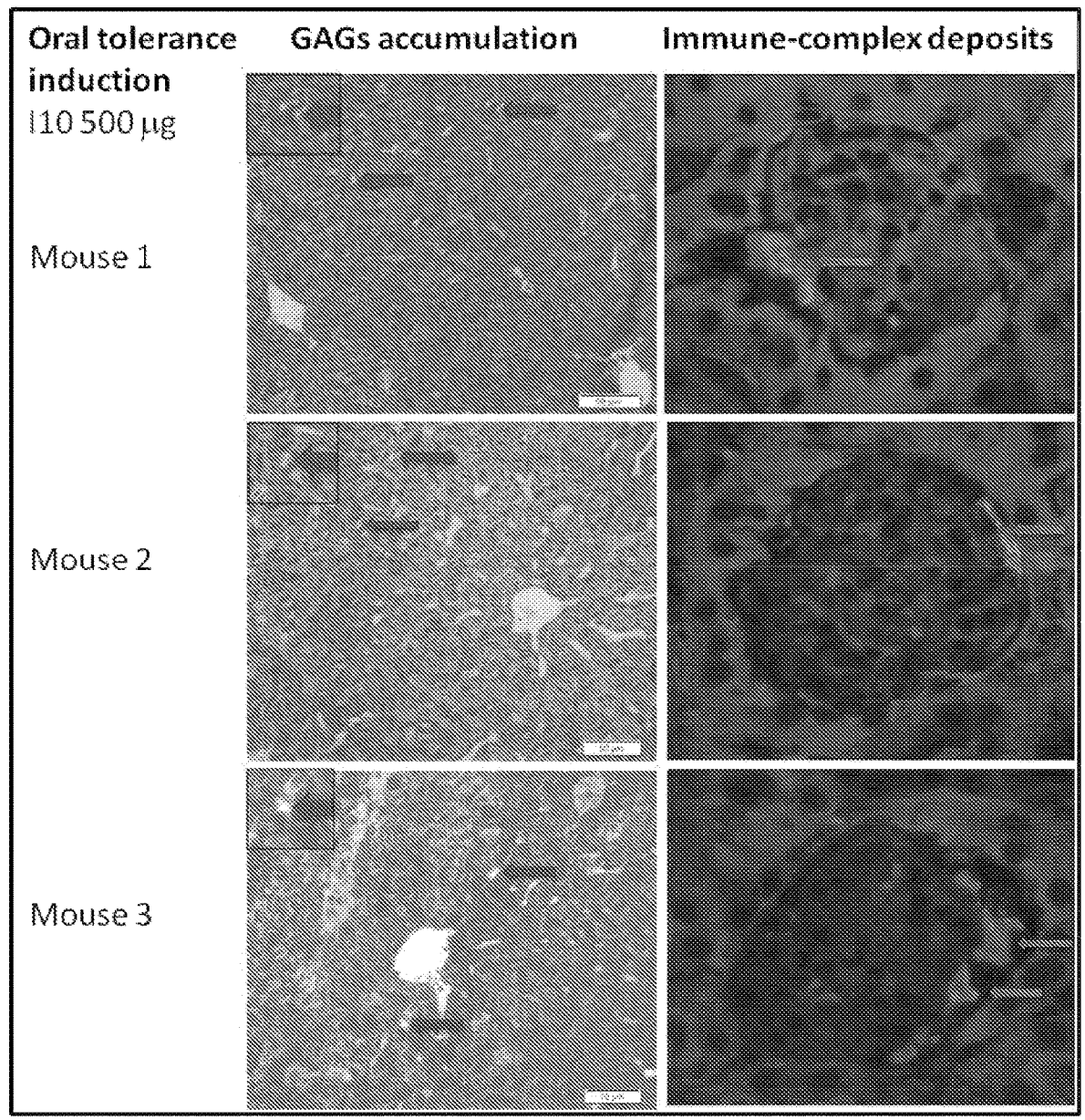

FIG. 31. Correlation between GAGs accumulation in liver and Immune-complex deposits in kidney after oral tolerance induction to GALNS. Oral tolerance was induced by feeding MKC mice with peptide I10 500 μg. One week after the last oral dose, mice received 16 weekly i.v. infusions of human GALNS. GAGs accumulation was evaluated in liver samples by light microscopy (40×) and immune-complex deposits were evaluated in kidney samples by fluorescence (100×).

Figure 32:
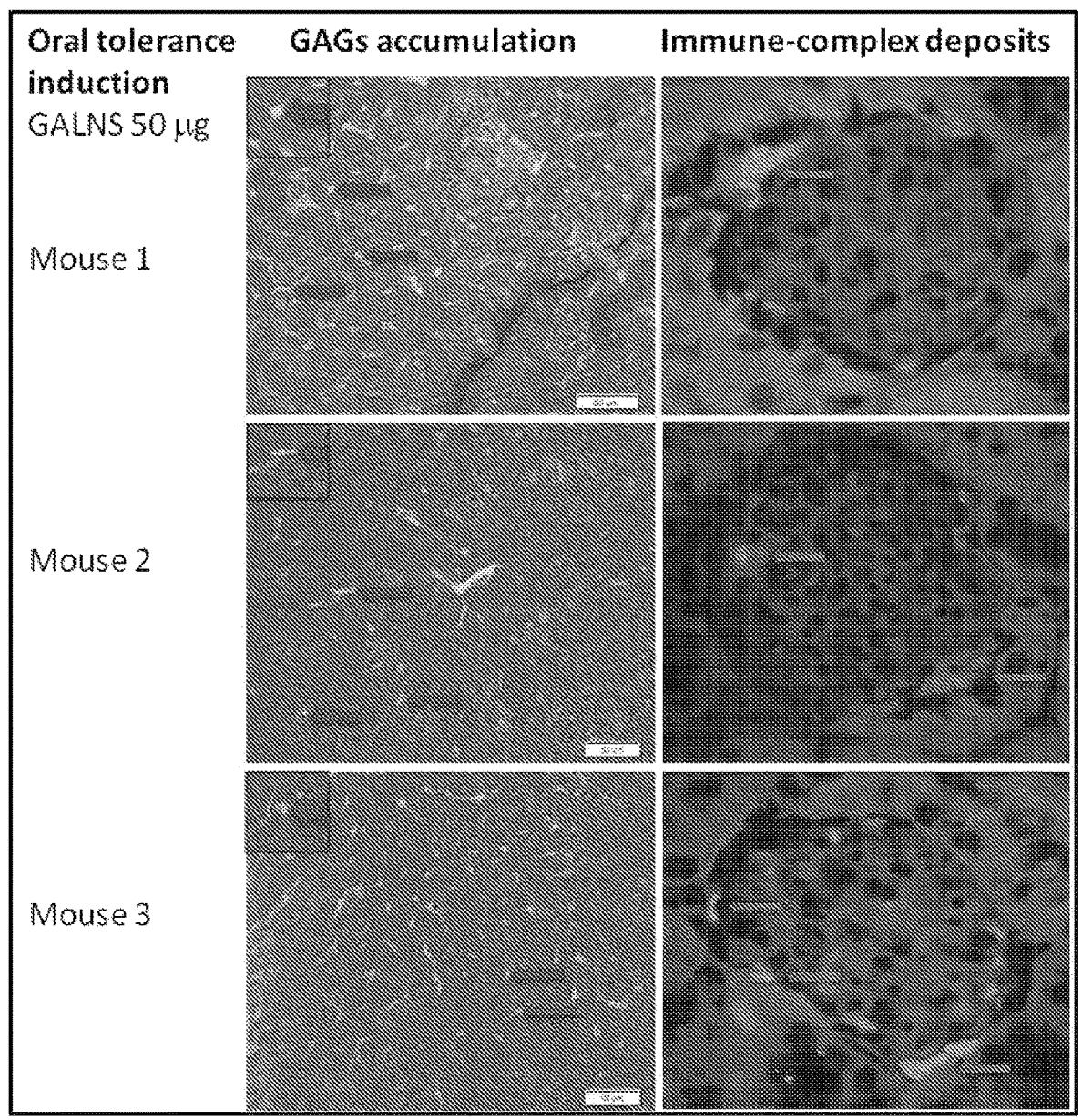

FIG. 32. Correlation between GAGs accumulation in liver and Immune-complex deposits in kidney after oral tolerance induction to GALNS. Oral tolerance was induced by feeding MKC mice with GALNS 50 μg. One week after the last oral dose, mice received 16 weekly i.v. infusions of human GALNS. GAGs accumulation was evaluated in liver samples by light microscopy (40×) and immune-complex deposits were evaluated in kidney samples by fluorescence (100×).

Figure 33:
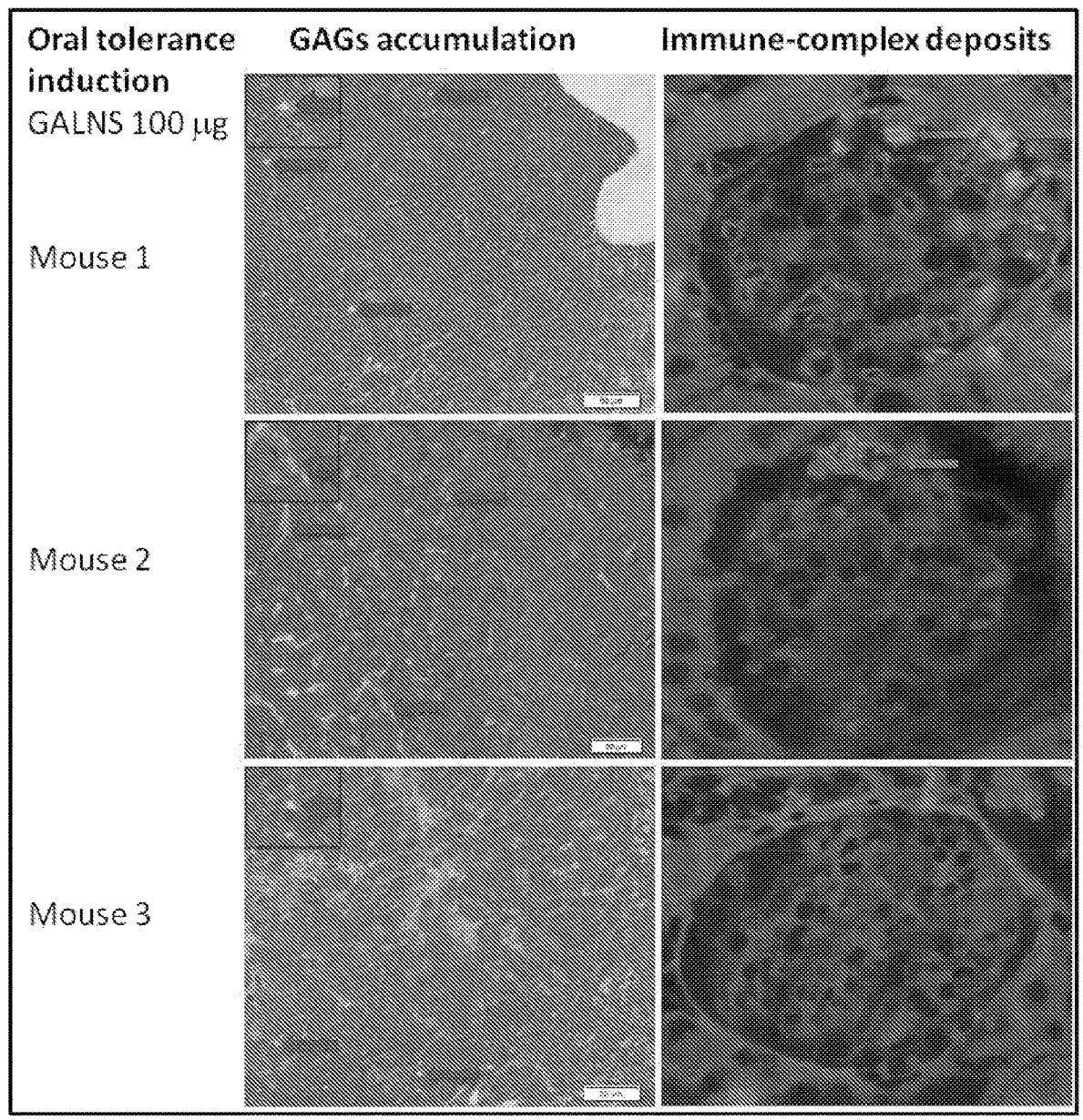

FIG. 33. Correlation between GAGs accumulation in liver and Immune-complex deposits in kidney after oral tolerance induction to GALNS. Oral tolerance was induced by feeding MKC mice with GALNS 100 μg. One week after the last oral dose, mice received 16 weekly i.v. infusions of human GALNS. GAGs accumulation was evaluated in liver samples by light microscopy (40×) and immune-complex deposits were evaluated in kidney samples by fluorescence (100×).

Figure 34:
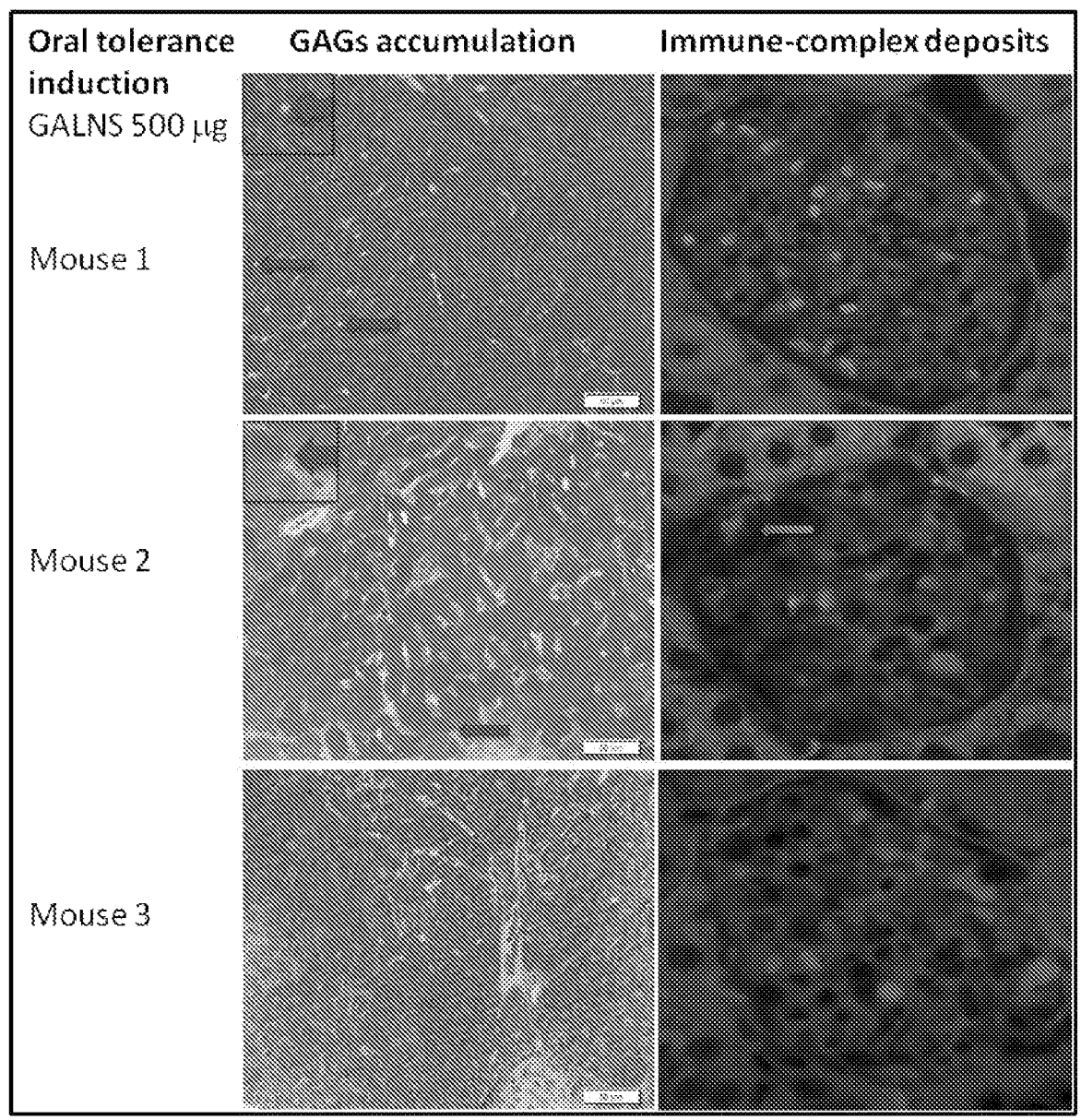

FIG. 34. Correlation between GAGs accumulation in liver and Immune-complex deposits in kidney after oral tolerance induction to GALNS. Oral tolerance was induced by feeding MKC mice with GALNS 500 μg. One week after the last oral dose, mice received 16 weekly i.v. infusions of human GALNS. GAGs accumulation was evaluated in liver samples by light microscopy (40×) and immune-complex deposits were evaluated in kidney samples by fluorescence (100×).

Figure 35:
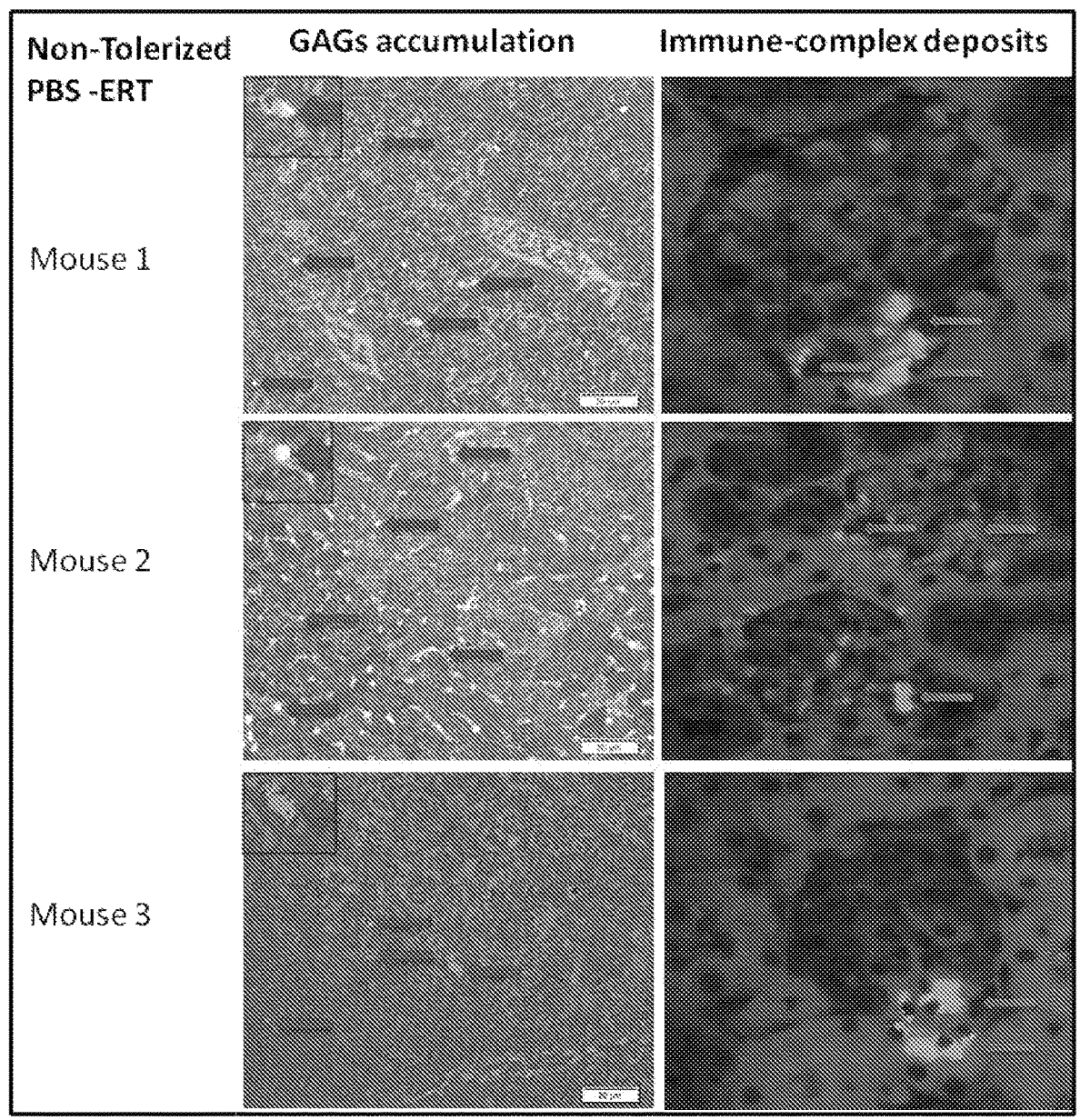

FIG. 35. Correlation between GAGs accumulation in liver and Immune-complex deposits in kidney after oral tolerance induction to GALNS. Oral tolerance was induced by feeding MKC mice with PBS. One week after the last oral dose, mice received 16 weekly i.v. infusions of human GALNS. GAGs accumulation was evaluated in liver samples by light microscopy (40×) and immune-complex deposits were evaluated in kidney samples by fluorescence (100×).

Figure 36:
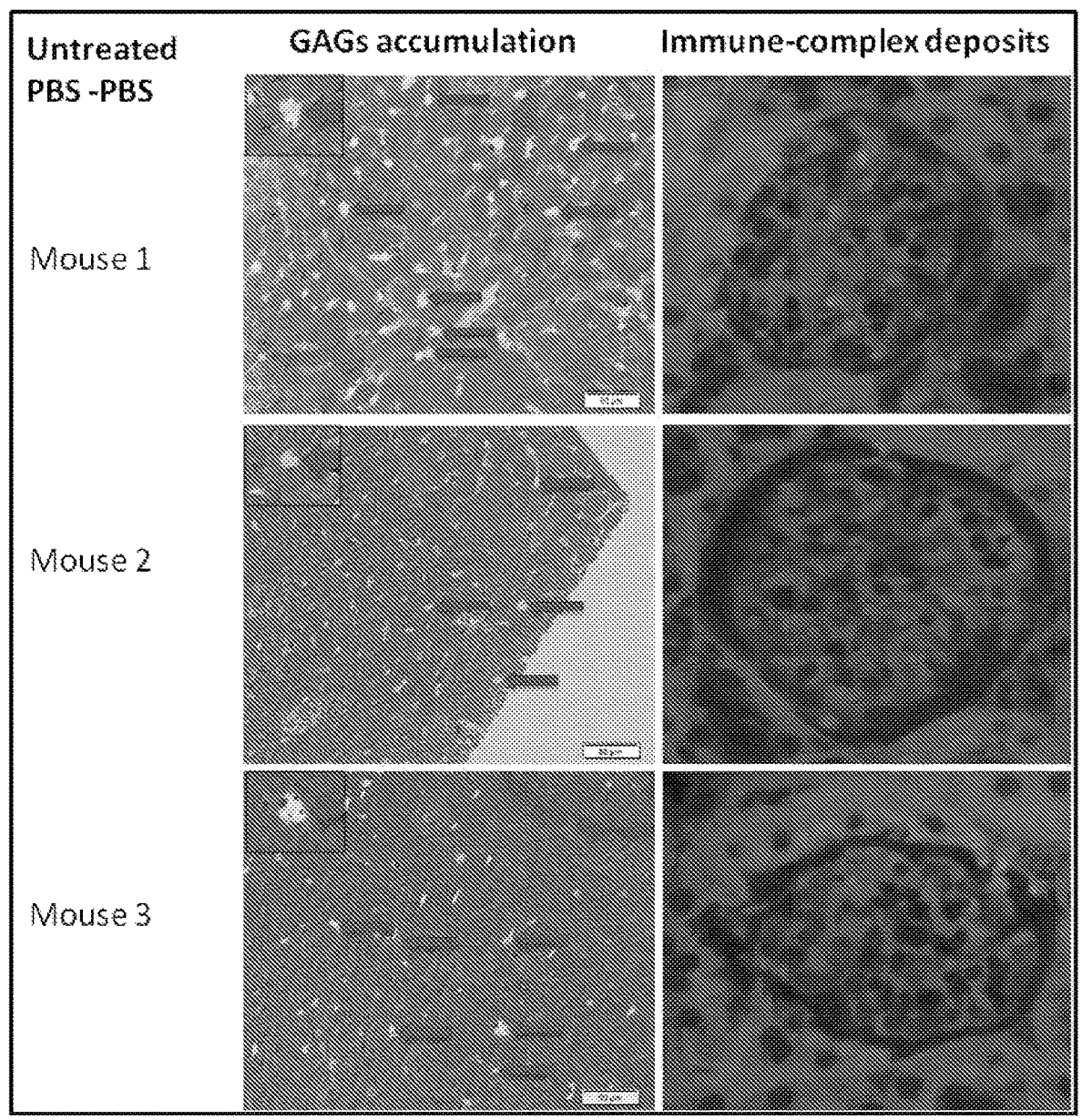

FIG. 36. Correlation between GAGs accumulation in liver and Immune-complex deposits in kidney after oral tolerance induction to GALNS. Oral tolerance was induced by feeding MKC mice with PBS. One week after the last oral dose, mice received 16 weekly i.v. infusions of PBS. GAGs accumulation was evaluated in liver samples by light microscopy (40×) and immune-complex deposits were evaluated in kidney samples by fluorescence (100×).

DETAILED DESCRIPTION OF THE INVENTION

Figure 5:
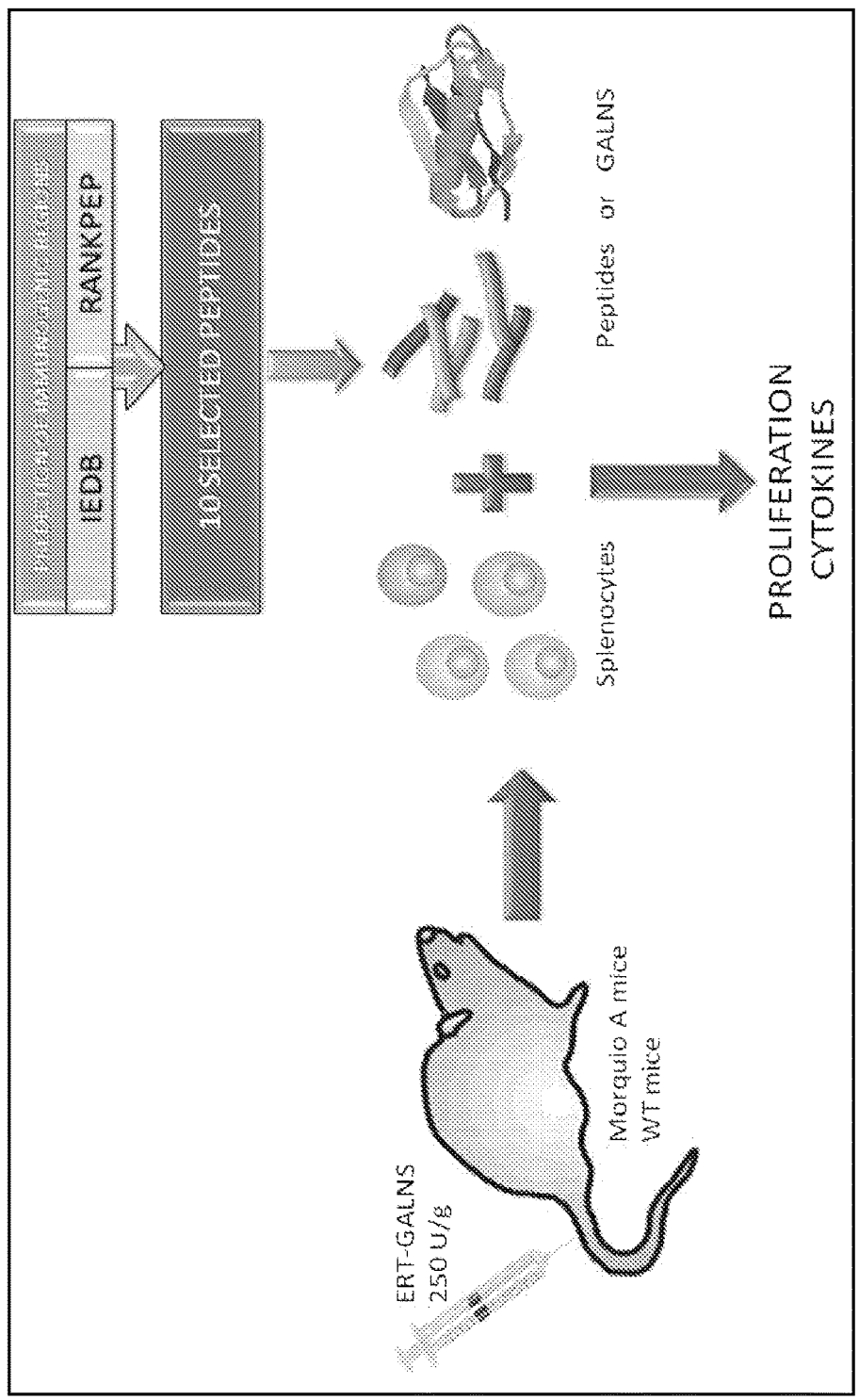

The Inventors disclose a method that includes using bioinformatic tools in combination with in vivo and in vitro immune reactivity assays to identify immunodominant peptides in enzymes administered for enzyme replacement therapy (ERT) (see FIG. 5 for overview). The Inventors have used this method to identify immunodominant peptides for the enzyme to N-acetylgalactosamine-6-sulfatase (GALNS), administered during ERT for treatment of MPS IVA. The inventors further disclose a method of inducing oral tolerance to GALNS in sensitive subjects using the identified immunodominant peptides in combination with an oral administration protocol (see FIG. 6 for overview and FIG. 7 for an example of an oral administration protocol in conjunction with enzyme replacement therapy). The inventors believe that this method may be applied to other enzymes used in ERT, practically those used to treat lysosomal storage disorders (LSDs).

I. Identification of Immunodominant Peptides.

Figure 6:
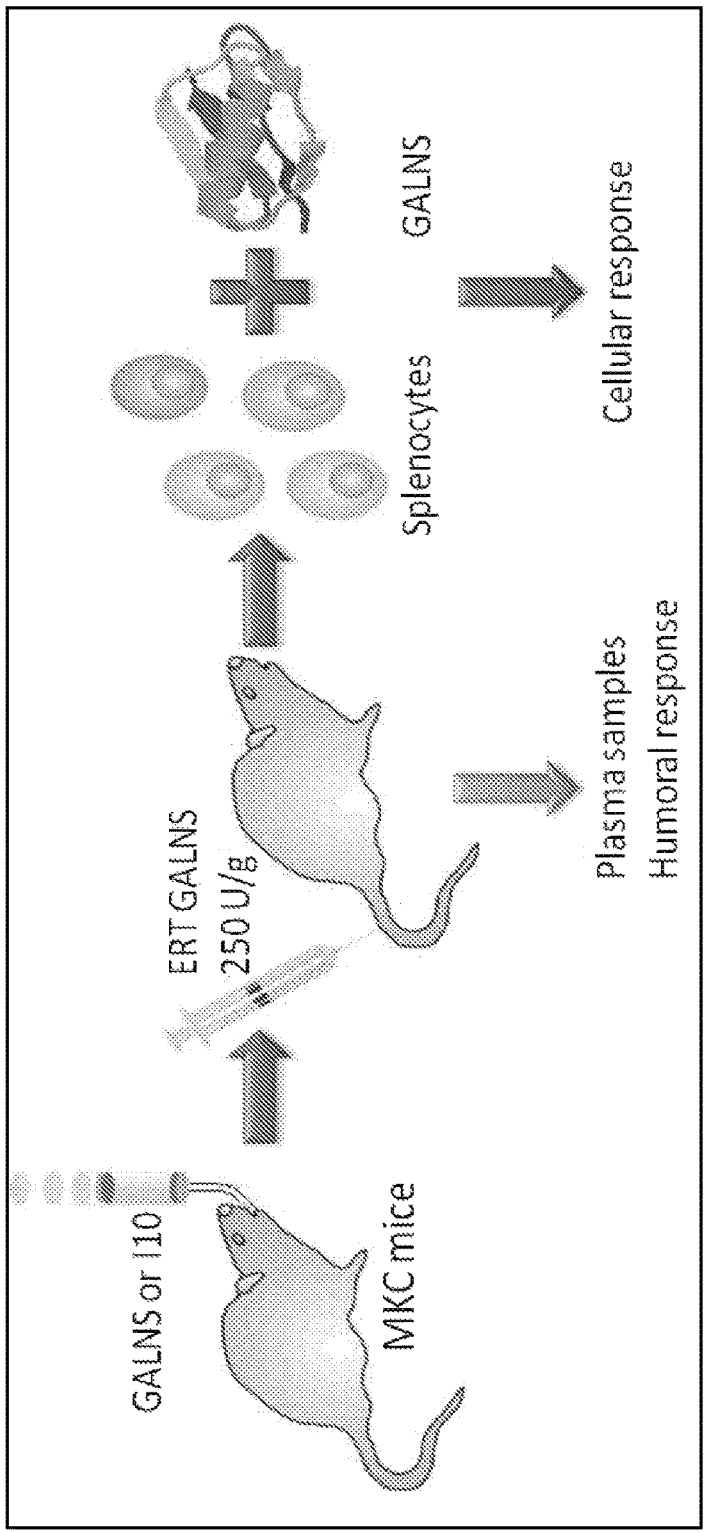

The inventors have identified immunodominant peptides of a target enzyme, using bioinformatics tools in combination with target enzyme deficient animals, and in vitro and in vivo humoral and cellular assays for immune response indicators. The following method steps were applied using GALNS as a target enzyme but it is believed that the method is applicable to other enzymes used in ERT, particular for other LSDs. Bioinformatic tools are first used to predict immunodominant peptides in the target enzyme. Peptides are then synthesized and evaluated in target enzyme deficient animals, for example mice, genetically engineered to be deficient in the target enzyme. These target enzyme deficient animals may be immunized or treated with the target enzyme according to an enzyme replacement protocol. These animals will then be immunoreactive towards the target enzyme or immunodominant peptide when challenged. Predicted immunodominant peptides may be evaluated and compared by challenging the immunogenic animal with a particular peptide and measuring indicators of immune responses. Indicators of immune responses include antibody production, splenocyte proliferation, and/or cytokine production which, may be measured and compared using in vivo and in vitro assays. The evaluation of immunodominant peptides by immune response indicators describe herein may be performed in any order and/or repeated in one or more different immune reactive animals as desired, to best distinguish or differentiate the predicted immunodominant peptides relative to one another or to the target enzyme (FIG. 5). Once preferred immunodominant peptides are identified they may be used or tested for the ability to induce oral tolerance in a subject, and thereby enhance the outcome of enzyme treatment therapy (FIG. 6).

1) Elimination of Signal Peptide.

If the enzyme for which identification of immunodominant peptides is desired contains a signal peptide it may first be necessary to eliminate the signal peptide from the peptide sequence to ensure that epitopes are not identified within the signal peptide region. This may be done using a bioinformatic tool, by way of example: ExPASy Proteomics Server (expasy.org) (Gasteiger et. al. (2003) Nucleic Acids Res. 31:3784-3788).

2) Identification of Predicted Immunodominant Peptides.

For an initial identification of potential immunodominant peptides, bioinformatic tools that may be used including, by way of example, RANKPEP (bio.dfci.harvard.edu/RANKPEP/) (Reche et al. (2002) Human Immunology, 63: 701-709; Reche et al. (2004) Immunogenetics, 56:405-419; Reche and Reinherz (2007) Methods Mol Biol., 409:185-200) and/or Immune Epitope Data Base (www.immuneepitope.org) (Vita et. al., (2010) Nucleic Acids Res. 2010; 38:D854-62). Potential immunodominant peptide sequences that are identified with either or both of these or similar bioinformatic tools may then be selected for further evaluation. GALNS immunogenicity and prediction of B-cell epitopes were evaluated by the Immune Epitope Data Base analysis resource. The algorithm is based on the predictions of surface accessibility and flexibility of the molecule, and the presence of β-turns and linear epitopes (Zhang et al. (20008) (IEDB-AR). Nucleic Acids Res., 2008: p. W513-8). MHC-II epitopes (H2-IAb) were predicted by IEDB and RANKPEP. Ten peptides were selected by the best scores of IC50 nM (concentration of peptide that inhibits binding of a standard peptide by 50%) and binding potential, respectively (Kim, et al. (2011) 374(1-2): p. 62-9).

3) Production of Peptides.

Predicted immunodominant peptides may be isolated or chemically synthesized. Many services are currently available for the synthesis of peptides including commercial services, by way of example, the Biomatik Corporation in Wilmington, Del. Alternatively peptides may be produced through genetic engineering, or fragmentation and isolation of intact GALNS molecules.

4) Immunization of Target Enzyme Deficient Animals.

Once predicted immunodominant peptides have been identified and isolated or synthesized, they may be further analyzed in target enzyme deficient animals. Preferred examples of target enzyme deficient animals include mice that have been genetically engineered not to express the target enzyme or epitope of interest. Target enzyme deficient mice may be immunized against the target enzyme and thus made immune reactive against the target enzyme and the associated immunodominant peptides or epitopes. Mice that do not express the particular target enzyme or epitope, for which immunodominant peptides are desired, are preferred as they are expected to be immune reactive when exposed to the target enzyme or epitope similar to patients undergoing ERT. It is not necessary that the animals completely lack expression of the target enzyme but may express enzymes with diminished activity. While not wishing to be bound by theory, enzymes with diminished activity may be defective due to deletions or variations of critical peptide sequences. These animals will mount an immune response to this critical region when presented with the corresponding wild type epitope. Examples of mice deficient in GALNS include: GALNS Knock-out mice (Galns−/−, MKC) (Tomatsu, et al. (2003) Hum Mol Genet. 12(24): p. 3349-58); missense mutation mice (Galnstm (C76S)slu, C2), (Tomatsu et al. (2007) 91(3): p. 251-8); and tolerant mice (Galnstm (hC79S.mC76S)slu MTOL) (Tomatsu et al. (2005) Hum Mol Genet. 14(22): p. 3321-35). These animals are derived from C57BL6 mice therefore wild-type C57BL6 mice may serve as appropriate controls. Mouse models for other LSDs disorders include a Heparan sulfamidase knock-out mouse for MPS IIIA, (Fu et al., (2007) Gene Ther 14:1065-1077) and a β-D-glucuronidase knockout mouse for MPS VII, (Birkenmeier et al., (1989) J Clin Invest. 83(4):1258-66).

For the purposes of identifying or differentiating immunodominant peptides, one or more of these enzyme deficient animals may be utilized. By way of example, enzyme deficient mice MKC, C2, and/or MTol as described above, may be immunized using a classical immunization protocol, or by subjecting the animals to ERT, using the target enzyme. Both MTol and wild type mice may be suitable controls to evaluate the response of the enzyme deficient mice. Methods of immunization are well known in the art, as are protocols for ERT. By way of example, mice that are genetically deficient in the target enzyme, may receive weekly intravenous (i.v.) infusions of the target enzyme for 10, 12, 14, 16, or more weeks at an amount adjusted to provide an immune response. In the examples that follow, the Inventors administered human GALNS intravenous weekly for 16, 18, 22, and 24 weeks at 250 U/g of body weight through the tail vein. A control group may receive PBS. After about weeks from the last infusion, humoral and cellular responses to the target enzyme or predicted immunodominant peptides may be measured as describe below.

5) Evaluation of Predicted Immunodominant Peptides.

After immunization with the target enzyme or ERT, the immunized animal, or cells derived from the immunized animal may be used to evaluate predicted immunodominant peptides. By way of example, after about after about 10 weeks from the last infusion, the immunized animal may be challenged with a predicted immunodominant peptide, and the blood, serum or plasma analyzed for specific antibodies directed to the predicted immunodominant peptides. Alternatively, or in addition to, splenocytes aseptically removed from the immunized animal may be challenged with a predicted immunodominant peptide and the culture analyzed for splenocyte proliferation and/or cytokine production. Non-limiting examples of cellular responses measured in vitro included splenocyte proliferation and production of various cytokines. Non-limiting preferred examples of cytokines which may be measured alone or in combination to indicate immune response include IL-4, IL-5, IL-17, IL-13, and IFN-γ. Methods of measuring cytokine production are well known in the art including the use of cellular and immunochemical assays. Peptides which elicited splenocyte proliferation, or cytokine production, may be considered to be immunodominant peptides. Alternatively, or in addition to, mice that are genetically deficient in the target enzyme may be examined for a humoral response. After immunization or ERT with the target enzyme, these mice may be examined for the presence of specific antibodies against the target enzyme or particular peptides. Specific antibodies may be easily detected in blood, plasma, or serum using immunohistochemical techniques, including Enzyme-linked immunosorbent assay (ELISA), against the target enzyme or a specific peptide.

Using the above methods as described in the examples, the Inventors were able to differentiate the predicted immunodominant peptides identified by bioinformatics. Of the 10 peptides identified by bioinformatics techniques, 3 indicated an increased immunodominant response relative to the 7 remaining peptides, and a significant response compared to the intact enzyme. This selection was done using immunizing enzyme deficient MKC mice. Upon further screening, using immunized MKC, C2, and MTol mice, 1 peptide indicated an increased immunodominant response relative to the other 2 and was selected for use in an oral administration protocol to establish oral tolerance in MKC mice.

II. Establishing Immunotolerance Through Oral Administration

It is expected that an oral administration protocol will vary with the amount administered as well as the particular immunodominant peptides selected and the individual subject. The term subject as used herein is meant to include animal subjects as well as human subjects. It is necessary that the peptides are administered before ERT commences to improve ERT outcome. It may be beneficial to administer more than one immunodominant peptide either separately or concurrently. By way of example, immunodominant peptides maybe administrated orally, for a period of time of about 4 days to about 7 days, about 7 days to about 10 days, about 10 days to about 2 weeks, about 2 weeks, about 2 weeks to about 3 weeks, about 3 weeks to about 4 weeks, about 4 weeks to about 5 weeks, about 5 weeks to about 6 weeks, about 6 weeks to about 7 weeks, about 7 weeks to about 8 weeks, about 8 weeks to about 9 weeks, about 10 weeks to about 12 weeks, about 12 weeks to about 14 weeks, about 14 weeks to about 16 weeks, about 18 week to about 18 weeks, or longer, prior to commencing ERT (also see Caminiti et al, (2009) 30: 4, pp. 443-448(6)). Immunodominant peptides may be administered daily or weekly. A preferred period of time for oral administration may be every other day for about 10 days prior to commencing ERT. These periods of time may be referred to as effective periods of time.

Non-limiting examples of enzyme replacement therapy are described herein. However, it is recognized that enzyme replacement therapy may administered using other methodologies. By way of example, enzyme replacement therapy may be administered using methodology commonly known as gene therapy, wherein an oligonucleotide encoding the target enzyme is administered to the subject in such a manner that the target enzyme is expressed by the subject. The compositions and methods disclosed herein may be applied to induce oral tolerance in a subject regardless of whether enzyme replacement therapy is administered by intravenous injection of active enzymes, gene therapy, or other methodologies.

Amounts of immunodominant peptides to be administered would also be expected to vary with the particular immunodominant peptide selected and the individual subject. Examples of amounts expected to be effective may be about 100 µg to about 200 µg, about 200 µg to about 400 µg, about 400 µg to about 600 µg, about 600 µg to about 800 µg, about 800 µg to about 1000 µg, about 1000 µg to about 1200 µg, about 1200 µg to about 1400 µg, about 1400 µg to about 1600 µg, about 1600 µg to about 1800 µg, about 1800 µg to about 2000 µg, about 2000 µg to about 5 mg, about 5 mg to about 10 mg, about 10 mg to about 20 mg, about 20 mg to about 30 mg, about 30 mg to about 40 mg, about 50 mg to about 50 mg, and about 50 mg to about 100 mg per administration. Preferred amounts are expected to be about 500 µg per administration. These amounts may be referred to as effective amounts.

Immunodominant peptides may be administrated orally as liquids, capsules, tablets, chewable tablets, or in any convenient form. Immunodominant peptides may be administrated in oral formulations containing naturally occurring or synthetic fillers, stabilizers, preservatives, buffers, rapid release, sustained release components and alike. One or more immunodominant peptides may be administered concurrently or sequentially. Immunodominant peptides may be administered in formulations containing other therapeutic agents as well.

It is expected the oral administration protocol will be administered by a skilled practitioner, typically a medical practitioner who may monitor the subject and may adjust the dosages and/or administration times accordingly. By way of example subjects may be monitored by determining their humoral response after the oral tolerance protocol has commenced. Alternatively, or in addition to, any number of indicators of inflammation may also be monitored, including those known in the art for monitoring autoimmune or inflammatory diseases, by way of example, experimental autoimmune encephalitis, type 1 and 2 diabetes, lupus, arthritis, and atherosclerosis.

Figure 7:
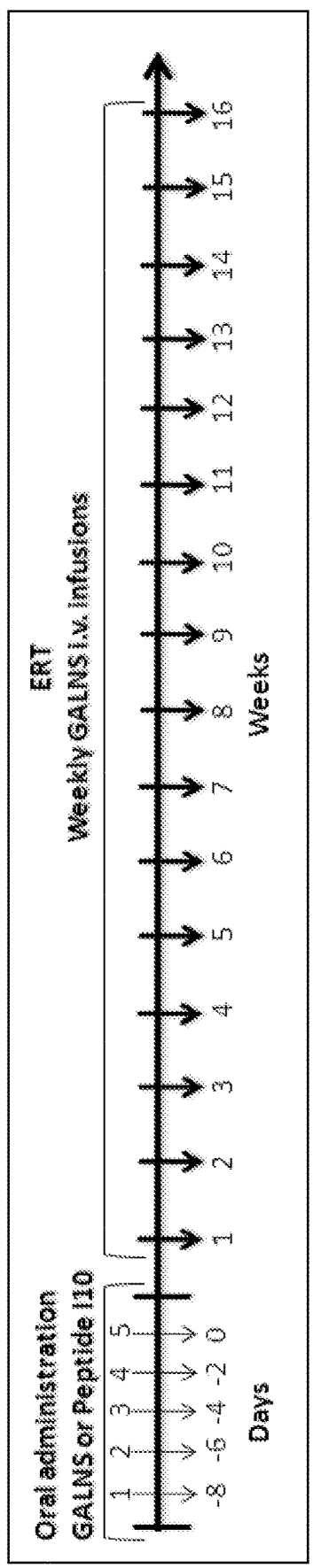

An example of an oral tolerance protocol is set forth in Table 2 and FIG. 7. In the examples that follow, the most immunodominant peptide, 10 (I10) and intact GALNS were administered in amounts according to Table 2, every other day beginning 10 days prior to ERT as illustrated in FIG. 7. The establishment of oral tolerance was tested using in vivo and in vitro assays, describe in section I, and by administering GALNS ERT, and comparing ERT outcome. The result was a decreased humoral and cellular response towards GALNS with a significant improvement in of ERT outcome compared to control mice.

In the examples that follow, the Inventors have demonstrated that an immunodominant peptide disclosed in Table 1, specifically SEQ ID NO: 12, was effective in inducing oral tolerance to GALNS in an appropriate subject. It is expected that the remaining immunodominant peptides disclosed in Table 1 would be also effective in inducing oral tolerance, particularly SEQ ID NO:6 and SEQ ID NO:10. The inventors have also demonstrated that the intact GALNS polypeptide (SEQ ID NO:2), was effective in inducing oral tolerance to GALNS when administered to an appropriate subject. Therefore, it is reasonably expected that fragments of the GALNS polypeptide, or SEQ ID NO:2, containing one or more immunodominant peptides identified in Table 1, preferably SEQ ID NO:6, SEQ ID NO:10, and/or most preferably SEQ ID NO:12, would also be effective in inducing oral tolerance in an appropriate subject.

The Inventors also recognize that it may not be necessary to administer the entire 20 amino acid sequence of the immunodominant peptides identified in Table 1 to induced oral tolerance and that smaller fragments of these peptides are also likely to be effective. By way of example, fragments of the immunodominant peptides identified in Table 1, preferably fragments of SEQ ID NO:6, SEQ ID NO:10, and most preferably SEQ ID NO:12, that are about 6, 7, 8, 9, 10, 11, 12, 13, 14, 15, 16, 17, 18, or 19 amino acids in length, may be effective in inducing oral tolerance when administered as described herein.

One embodiment of the invention are the immunodominant peptides disclosed in Table 1: SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, preferably SEQ ID NO:6, and SEQ ID NO:10, and most preferably SEQ ID NO:12.

In another embodiment of the invention are fragments of the peptides disclosed in Table 1, preferably SEQ ID NO:6, and SEQ ID NO:10, and most preferably SEQ ID NO:12.

In another embodiment are fragments of the target enzyme GALNS (SEQ ID NO:2), which contain one or more of the immunodominant peptides disclosed in Table 1, preferably SEQ ID NO:6, and SEQ ID NO:10, and most preferably SEQ ID NO:12.

In another embodiment are fragments of a polypeptide as substantially set forth in SEQ ID NO:2, which contain one or more of the immunodominant peptides disclosed in Table 1, preferably SEQ ID NO:6, and SEQ ID NO:10, and most preferably SEQ ID NO:12.

In another embodiment of the invention is a method of using either the immunodominant peptides of Table 1, fragments thereof, GALNS polypeptide, SEQ ID NO:2, or fragments of SEQ ID NO:2 containing immunodominant peptides, preferably SEQ ID NO:6, and SEQ ID NO:10, and most preferably SEQ ID NO:12, to induce oral tolerance in a subject suffering from Mucopolysaccharidosis type IVA.

In yet another embodiment of the inventions is a method of determining immunodominant peptides of a target enzyme used in enzyme replacement therapy for treatment of a lysosomal storages disorder.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLES

Methods and Materials for Examples 1-23
Production and Purification of Human GALNS The enzyme was produced in Chinese hamster ovary (CHO) cells overexpressing recombinant human GALNS. The purification was made according to the protocol previously reported (Tomatsu et al. (2007) Mol. Genet Metab.; 91(1):69-78). In brief, CHO clones expressing human GALNS were cultured in DMEM supplemented with 15% FBS, 400 µg/ml G418 (Sigma), 2 mM L-glutamine, 34.5 µg/ml of proline, 100 units of penicillin and 100 µg/ml of streptomycin at 37° C. in 5% of $CO_2$. Cells were grown, in CHO PF protein free medium (EX-Cell™ 325; JRH Bioscience), after reaching confluence supplemented with 2 mM L-glutamine, 34.5 µg/ml of proline, 10 mM Hepes, 100 units of penicillin and 100 µg/ml of streptomycin at 37° C. in 5% of $CO_2$. The media was collected every 24 h, centrifuged (6,000 rpm for 20 min at 4° C.) and stored at −20° C. until use.

The purification was made according to the protocol previously reported (Tomatsu et al. (2007) Mol Genet Metab., 91(1): p. 69-78). Briefly, human GALNS was purified from CHO cells culture media. Media was filtered through a 0.2 µm membrane and adjusted to pH 5.5 with acetic acid. Using an Amicon stirred-cell ultrafiltration unit, the filtered medium was concentrated 15-fold with an ultrafiltration membrane NMWL 30,000 (Millipore). The concentrated medium was loaded onto a CM-sepharose column previously equilibrated (25 mM sodium acetate and 1 mM β-glycerolphosphate pH 5.5) at a flow rate of 25 ml/h. The enzyme was eluted with 200 ml of a linear gradient of 0-0.1 M NaCl at a flow rate of 25 ml/h. The fractions with GALNS activity were pooled, concentrated by microfiltration in a Centricon plus-70 (Millipore) and applied to a Sephacryl S-100 HR at a flow rate of 25 ml/h. The enzyme was eluted with equilibrium buffer (25 mM sodium acetate, 1 mM β-glycerolphosphate and 0.1 M NaCl, pH 5.5). Fractions with higher GALNS activity were analyzed under denaturating conditions in a 12% SDS-PAGE gel. Selected fractions were pooled and concentrated by an Amicon centrifugal filter (Millipore Ultracel). Enzyme activity of GALNS was determined according to the fluorometric assay previously reported (van Diggelen et al. (1990) Clin Chim Acta., 187(2): p. 131-9). One unit of GALNS enzyme activity is defined as the amount of enzyme that catalyzes the conversion of 1 nmol of 4 methylumbelliferyl-β-D-galactopyranoside-6-sulfate per hour.

The immunodominant peptides may be referred to herein, by their sequence number, SEQ ID number, or their experimental reference number. Table 1 is provided for identification and cross reference of the corresponding peptide sequence. Various operations may be described as multiple discrete operations in turn, in a manner that may be helpful in understanding embodiments; however, the order of description should not be construed to imply that these operations are order dependent.

Method and Materials for Examples 1-4
Prediction of GALNS Epitopes

Human N-acetylgalactosamine-6-sulfatase (GALNS) (SEQ ID NO:1) sequence was available in the NCBI protein data base (www.ncbi.nlm.nih.gov) (Ascension No. P34059, P34059.1, GI:462148). The signal peptide prediction was made using the proteomics and sequence analysis tools of the ExPASy Proteomics Server (expasy.org) (Gasteiger et. al. (2003) Nucleic Acids Res. 31:3784-3788) to ensure that the epitopes were not located in the signal peptide region.

Elimination of the signal peptide from GALNS resulted in SEQ ID NO:2. For the prediction of the immunodominant peptides in GALNS the Inventors use a combination of two computational algorithms to predict potential epitopes: Immune Epitope Database analysis resource (IEBD) (www.immuneepitope.org) (Vita et. al. (2010) Nucleic Acids Res. 2010; 38:D854-62) and RANKPEP (bio.dfci.harvard.edu/RANKPEP/) (Reche et al. (2002) Human Immunology, 63: 701-709; Reche et al. (2004) Immunogenetics, 56:405-419; Reche and Reinherz (2007) Methods Mol Biol., 409: 185-200). Ten peptides predicted by these algorithms were selected (Table 1).

Evaluation of Immunodominant Peptide

The immunodominant GALNS peptides were evaluated by two different approaches: Animals treated 1) by a classical immunization protocol (data not shown) and 2) by ERT. Mice (MKC) genetically engineered not to express GALNS were used in these examples. For the classical protocol of immunization, a group of 8 week old mice (n=6) were immunized with 10 μg (n=2) or 20 μg (n=2) of GALNS emulsified in Complete Freund's adjuvant (CFA). 200 μl of the emulsion were administered as a subcutaneous injection. Two boosters were made at intervals of two weeks with 10 or 20 gig of GALNS emulsified in Incomplete Freund's adjuvant (IFA). Control mice (n=2) were immunized with PBS emulsified in CFA and IFA respectively (Chung et al. (2005) J. Leukoc Biol. 77(6):906-13)). For the ERT, a group of 8 week old mice (n=25) received intravenous infusions of GALNS: 250 U/g of body weight (n=10) or 1000 U/g of body weight (n=10) through the tail vein. A control group (n=5) received PBS (Tomatsu et al. (2008) Hum Mol Genet. 15; 17(6):815-24). FIG. 1 shows an illustration of an example DBS system 100 implanted in a patient 104. DBS system 100 includes an implantable neurostimulator or pulse generator 108. The pulse generator 108 includes a control unit or controller 128 and may be implanted within the patient's body, e.g., in a region 124 beneath the clavicle.

Lymphocyte Proliferation

Ten days after the last immunization or the last infusion, the mice were euthanized and the spleen was aseptically removed. The tissue was homogenized with a syringe plunger in complete RPMI 1640 medium (10% fetal bovine serum, 2 μM glutamine, 50 U penicillin/ml, 50 μg streptomycine/ml, 100 μM non-essential amino acids, 50 μM 2-mercaptoethanol). The suspension was centrifuged at 1000 rpm during minutes. The red blood cells were lysed using a hypotonic lysis buffer (Sigma® R7757). In a 96-well plate, $5\times10^5$ splenocytes/well were stimulated with the individual peptides (10, 25, 50 or 100 μg/ml), the complete GALNS (50 or 100 μg/ml) or ConA (3 μg/ml) in triplicates during 72 h at 37° C., saturated humidity and 5% $CO_2$. Cells were pulsed with 1 JpCi of [3H]thymidine for the last 18 h of incubation. [3H]thymidine incorporation was measured by R-Scintillation counter (Trilux Microbeta Counter). The Stimulation Index (SI) was calculated as the mean value of the three wells for each condition divided by the mean value of the unstimulated cells (Mirano-Bascos (2010) J Virol. 84(7):3303-11).

Cytokine Determination

The production of cytokines after peptide stimulation was evaluated as intracellular staining (by flow cytometry) and secreted cytokines (by LUMINEX). In a 48-well plate, $6\times10^6$ splenocytes/well were stimulated with 1) the individual peptides (10, 25, 50, or 100 μg/ml), 2) the complete GALNS (50 or 100 μg/ml) or 3) Concavalin A (3 μg/ml) in duplicates during 72 h at 37° C., saturated humidity and 5% $CO_2$. The cells were treated with 1 μl of a protein transport inhibitor BD GolgiPlug™ during 5 h at 37° C., saturated humidity and 5% $CO_2$. The suspension of cells was centrifuged at 1000 rpm during 10 minutes. The supernatants were collected by further analysis with LUMINEX. The Fc receptors were blocked with 1 μl of α-mouse CD16/32 (e-Bioscience) during 15 min at 4° C. After washing, the cells were stained with PE-Cy7-labeled anti-mouse CD4 and Alexa700-labeled anti-mouse CD8 antibodies during 30 min at 4° C. After two washes, cells were permeabilized with a BD fixation/permeabilization solution during 20 min at 4° C. Cells were washed two times and stained with a cocktail of antibodies for intracellular staining (PE-labeled anti-mouse IL-4, APC-labeled anti-mouse IL-5 and FITC-labeled anti-mouse IFN-γ). After two washes, cells were analyzed by flow cytometry. Secreted cytokines (IL-4, IL-5, IL-13, IL-17 and IFN-γ) in the collected supernatants were detected by using a bead immunoassay kit which allows the measurement of multiple proteins simultaneously (LUMINEX technology, using a Millipore Milliplex™ kit).

Materials and Methods Examples 5-8

Evaluation of Predicted Immunodominant Peptides

The predicted peptides from Example 1 were reevaluated in MKC mice to reaffirm the selection of peptides 4, 8, and 10. The mice received 16, 18, 22, or 24 weekly intravenous (i.v.) infusions of human GALNS: 250 U/g of body weight through the tail vein. A control group received PBS. Ten days after the last infusion, the mice were euthanized and the spleens were aseptically removed. The tissues were homogenized with a syringe plunger in complete RPMI 1640 medium (10% fetal bovine serum, 2 μM glutamine, 50 U penicillin/ml, 50 μg streptomycin/ml, 100 μM non-essential aminoacids, 50 μM 2-mercaptoethanol). The suspension was centrifuged at 1,000 rpm during 10 minutes. The red blood cells were lysed using a Lysis buffer (Sigma). The specificity of cellular response against the peptides or the complete enzyme in the in vitro stimulation was determined by splenocyte proliferation or cytokine secretion in ERT treated mice or PBS injected control mice.

Splenocytes Proliferation

In a 96-well plate, $5\times10^5$ splenocytes/well were stimulated with the individual peptides (100 μg/ml), the complete GALNS (150 μg/ml) or concanavalin A (ConA) (3 μg/ml) in triplicates during 72 h at 37° C., saturated humidity and 5% $CO_2$. Cells were pulsed with 1 μCi of radioactive thymidine for the last 18 h of incubation. 3H-Thymidine incorporation was measured by β-Scintillation counter (Trilux Microbeta Counter). Proliferation data are expressed as counts per minute (cpm) values (FIG. 5). (Mirano-Bascos et al. (2010) J Virol. 84(7): p. 3303-11).

Detection of Secreted Cytokines

Cytokines were determined in the cell culture supernatants. In a 96-well plate, $1\times10^6$ splenocytes/well were stimulated with the individual peptides (100 μg/ml), the complete GALNS (150 μg/ml), ConA (3 μg/ml) or media in triplicates during 72 h at 37° C., saturated humidity and 5% $CO_2$. Cells were centrifuged at 1,000 rpm during 10 min. Secreted cytokines (IL-4, IL-5, IL-13, and IFN-γ) in the collected supernatants were detected by a bead immunoassay kit which allow the measurement of multiple proteins simultaneously (LUMINEX xMAP Technology, using a Millipore Milliplex™ kit) according to manufacturer's instructions (FIG. 5).

Methods and Materials for Examples 8-23

Evaluation of Immunodominant Peptides 4, 8, and 10, Using Cellular Responses in Immune Reactive Mice.

Morquio A mouse models: a). Knock-out mice (Galns−/−, MKC) (Tomatsu et al. (2003) Hum Mol Genet. 12(24): p.

3349-58), b) Tolerant mice (Galnstm (hC79S.mC76S) SLU MTol) (Tomatsu et al, (2005) Hum Mol Genet. 14(22): p. 3321-35).c). Missense mutation mice (Galnstm (C76S) SLU C2) (Tomatsu et al. (2007) Mol Genet Metab., 91(3): p. 251-8), and wild-type C57BL6 mice were treated by ERT. The mice received 16 weekly i.v. infusions of human GALNS: 250 U/g of body weight through the tail vein. A control group received PBS.

Detection of Mice Plasma Levels of IgG Anti-GALNS

An indirect ELISA technique was used to detect plasma IgG antibodies against GALNS in treated and untreated mice. Ninety-six well polystyrene microplates were coated with 2 µg/ml of GALNS enzyme in coating buffer (15 mM $Na_2CO_3$, 35 mM $NaHCO_3$, 0.021 $NaN_3$ pH 9.6) and incubated overnight at 4° C. in a wet chamber. The plates were blocked with 3% casein in PBS during 1 h at room temperature in a wet chamber. After two washes, first with TTBS (10 mM Tris, 150 mM NaCl, 0.05% Tween 20, pH 7.5), and then with TBS (10 mM Tris, 150 mM NaCl, 0.05%, pH 7.5), 100 ml of mice plasma samples diluted (1:1,000) in TTBS were added to the plate and incubated 2 h at 37° C. in a wet chamber. Four washes with TTBS were performed. 100 µl of anti-mouse IgG-Peroxidase (Sigma) 1:5,000 dilution in TTBS were applied. After three washes with TTBS, followed by one wash with TBS, the experiment was developed with the substrate TMB (3,3',5,5'-Tetramethylbenzidine, Sigma). The enzymatic reaction was stopped with IN HCl solution and the absorbance was measured at 450 nm in a microplate reader Multiskan® EL800 (Bio-Tek Instruments). Plasma concentrations of IgG antibodies anti-GALNS were derived by extrapolation of the absorbance values from a calibration curve using a mAb anti-GALNS.

Evaluation of Cellular Response

The specificity of cellular response against GALNS used in ERT was evaluated in vitro by splenocyte proliferation or cytokine secretion in ERT treated mice or PBS control mice. Ten days after the last infusion, the mice were euthanized and the spleen was aseptically removed. The tissue was homogenized with a syringe plunger in complete RPMI 1640 medium (10% fetal bovine serum, 2 µM glutamine, 50 U penicillin/ml, 50 µg streptomycinlml, 100 µM non-essential amino acids, 50 µM 2-mercaptoethanol). The suspension was centrifuged at 1,000 rpm during 10 minutes. The red blood cells were lysed using a Lysis buffer (Sigma).

Splenocytes Proliferation

In a 96-well plate, $5 \times 10^5$ splenocytes/well were stimulated with the individual peptides (100 µg/ml), the complete GALNS (150 µg/ml) or ConA (3 µg/ml) in triplicates during 72 h at 37° C., saturated humidity and 5% $CO_2$. Cells were pulsed with 1 µCi of radioactive thymidine for the last 18 h of incubation. Thymidine incorporation was measured by β-Scintillation counter (Trilux Microbeta Counter) Mirano-Bascos, et al. (2010) J Virol. 84(7): p. 3303-11).

Detection of Secreted Cytokines

Cytokines were determined in the cell culture supernatants. In a 96-well plate, $1 \times 10^6$ splenocytes/well were stimulated with the individual peptides (100 µg/ml), the complete GALNS (150 µg/ml), ConA (3 µg/ml) or media in triplicates during 72 h at 37° C., saturated humidity and 5% $CO_2$. Cells were centrifuged at 1000 rpm during 10 min. Secreted cytokines (IL-4, IL-5, IL-13, and IFN-γ) in the collected supernatants were detected by a bead immunoassay kit which allow the measurement of multiple proteins simultaneously (LUMINEX xMAP Technology, using a Millipore Milliplex™ kit) according to manufacturer's instructions.

Protocol for Induction for Induction of Oral Tolerance and Evaluation.

For an overview of oral tolerance and evaluation see FIG. 6. Six week old MKC mice (GALNS-/-) were divided in 8 groups, three mice per group (Table 2). All animals were maintained in the animal facility at the Saint Louis University. Oral tolerance was induced by feeding mice with 50, 100 or 500 µg of peptide I10 or GALNS enzyme (groups 1 to 6). Control groups (7 and 8) received PBS alone. The mice were treated by oral gavage every other day over a period of 9 days. One week after the last oral administration, the mice were treated by weekly i.v. infusions of GALNS enzyme at 250 U/kg of body weight through the vein of the tail (groups 1 to 7), or PBS (group 8) during 4 months (FIG. 7).

TABLE 2

Groups of mice and amounts used oral tolerance induction.

| | ORAL ADMINISTRATION | | ERT Weekley i.v. |
|---|---|---|---|
| GROUP | Peptide I10 | GALNS | infusions |
| 1 | 50 mg | | GALNS |
| 2 | 100 mg | | GALNS |
| 3 | 500 mg | | GALNS |
| 4 | | 50 mg | GALNS |
| 5 | | 100 mg | GALNS |
| 6 | | 500 mg | GALNS |
| 7 | PBS | | GALNS |
| 8 | PBS | | PBS |

Splenocytes Proliferation

Ten days after the last infusion, the mice were euthanized and the spleens were aseptically removed. The tissue was homogenized with a syringe plunger in complete RPMI 1640 medium (10% fetal bovine serum, 2 µM glutamine, 50 U penicillin/ml, 50 µg streptomycin/ml, 100 µM non-essential amino acids, 50 µM 2-mercaptoethanol). The suspension was centrifuged at 1,000 rpm for 10 minutes. The red blood cells were lysed using a Lysis buffer (Sigma).

In a 96-well plate, $5 \times 10^5$ splenocytes/well were stimulated with GALNS enzyme (150 µg/ml), ConA (3 µg/ml) or media in triplicates during 72 h at 37° C., saturated humidity and 5% $CO_2$. Cells were pulsed with 1 µCi of radioactive thymidine for the last 18 h of incubation. Thymidine incorporation was measured by ~-Scintillation counter (Trilux Microbeta Counter) (FIG. 6).

Detection of Secreted Cytokines

In a 96-well plate, $1 \times 10^6$ splenocytes/well were stimulated with GALNS enzyme (150 µg/ml), ConA (3 µg/ml) or media in triplicates during 72 h at 37° C., saturated humidity and 5% $CO_2$. Secreted cytokines (IL-4, IL-5, IL-10, IL-13 and IFN-γ) in the collected supernatants were detected by a bead immunoassay kit which allow the measurement of multiple proteins simultaneously (LUMINEX xMAP Technology, using a Millipore Milliplex™) kit according manufacturer's instructions (FIG. 6).

Detection of IgG and IgE Antibodies Against GALNS by ELISA

An indirect ELISA technique was used to detect plasma IgG and IgE antibodies against GALNS in treated and untreated mice. Ninety-six well polystyrene microplates were coated with 2 µg/ml of GALNS enzyme in coating buffer (15 mM Na$_2$CO$_3$, 35 mM NaHCO$_3$, 0.021 NaN$_3$ pH 9.6) and incubated overnight at 4° C. in a wet chamber. The plates were blocked with 3% Casein in PBS for 1 h at room temperature in a wet chamber. After two washes, first with TTBS (10 mMTris, 150 mM NaCl, 0.05% Tween20, pH 7.5), and then with TBS (10 mM Tris, 150 mM NaCl, 0.05%, pH 7.5), 100 ml of mice plasma samples diluted 1:500, for IgE and 1:1,000 for IgG, in TTBS were added to the plate and incubated 2 h at 37° C. in a wet chamber. Four washes with TTBS were performed. 100 µl of anti-mouse IgE-HRP (Thermo Scientific) 1:1,000 in TTBS or IgG-Peroxidase (Sigma) 1:5,000 dilution in TTBS were applied. After three washes with TTBS, followed by one wash with TBS, the experiment was developed with the substrate TMB (3,3',5, 5'Tetramethylbenzidine). The enzymatic reaction was stopped with IN HCl solution and the absorbance was measured at 450 nm in a Multiskan® EL800 (Bio-Tek Instruments). Plasma concentrations of IgG antibodies anti-GALNS were derived by extrapolation of the absorbance values from a calibration curve using a mAb anti-GALNS.

Comparison of ERT Efficacy Between Tolerized and Non-Tolerized MPS IVA Knock-Out Mice.

Efficacy of ERT was tested by histopathology. Liver tissues from 24 mice used in the oral tolerance protocol were evaluated for GAGs storage. Tissues were fixed in 4% paraformaldehyde/2% glutaraldehyde and embedded in Spurr's resin. Sections of tissues were stained with Toluidine blue and evaluated by light microscopy (×40) (Tomatsu et al. (2003) Hum Mo! Genet. 12(24): p. 3349-58). Kidney biopsies were fixed in Hollande's fixative (3.7% formaline, 40% picric acid, 25% copper acetate and 1.5% acetic acid) and embedded in Spurr's resin. Sections were stained in Harris' unacidified hematoxylin and an alcohol solution of eosin for immune complex detection by fluorescence microscopy (450-490 nm excitation filter and 515 nm suppression filter) (×100) (McMahon et al. (2002) Mod Pathol. 15(9): p. 988-97). A comparison between tolerized and non-tolerized MKC mice treated by ERT was performed.

Statistical Analysis

The results are expressed as the mean±sd. for each for each mouse or group of mice. Statistical analyses were done with Statistix 9.0. Two sample T-Test was used to compare the significant difference among mice or group of mice.

Example 1

The Inventors applied the bioinformatic tools RANKPEP and Immune Epitope Data Base, to N-acetylgalactosamine-6-sulfatase (GALNS). The sequences in were used as an initial selection of potential T and B epitopes or immunodominant peptides.

TABLE 1

Predicted immunodominant peptides. The immunodominant peptides, referred to herein, by their sequence number, SEQ ID number, or their experimental reference number, may be identified and cross referenced according to the following table.

| No. | Location | Sequence | SEQ ID NO. | Exp. Ref. No. | Algorithm |
|---|---|---|---|---|---|
| 1 | 477-496 | KLGKTLTPPESIPKKTLWSH | (SEQ ID NO. 3) | J1 | IRDB |
| 2 | 18-37 | GDLGVYGEPSRETPNLDRMA | (SEQ ID NO. 4) | A2 | IEDB |
| 3 | 75-94 | NAHARNAYTPQEIVGGIPDS | (SEQ ID NO. 5) | B3 | IEDB |
| 4 | 135-154 | PNCHFGPYDNKARPNIPVYR | (SEQ ID NO. 6) | C4 | IEDB/RANKPEP |
| 5 | 215-234 | ASKPFLGTSQRGRYGDAVRE | (SEQ ID NO. 7) | F5 | IEDB/RANKPEP |
| 6 | 265-284 | AALISAPEQGGSNGPFLTGK | (SEQ ID NO. 8) | G6 | IEDB |
| 7 | 321-340 | TTSLALAGLTPPSDRAIDGL | (SEQ ID NO. 9) | H7 | IEDB |
| 8 | 200-219 | FFLYWAVDATHAPVYASKPF | (SEQ ID NO. 10) | E8 | RANKPEP |
| 9 | 180-199 | TQTYLQEALDFIKRQARHHP | (SEQ ID NO. 11) | D9 | RANKPEP |
| 10 | 447-466 | QQHQEALVPAQPQLNVTNWA | ((SEQ ID NO. 12) | 110 | IEDB |

Example 2

Evaluation of Potential Immunodominant Peptides Using by Splenocytes Proliferation Assay The Inventors harvested and cultured splenocytes from mice (MKC) treated with enzyme replacement therapy by infusion of GALNS. After treatment of cultures with the potential Immunodominant peptides, it was found that three peptides Nos. 4, S, and 10, elicited a strong response as indicated by splenocyte proliferation (FIG. 1).

Example 3

Evaluation of Potential Immunodominant Peptides by Cytokine Production Assay

Figure 2:
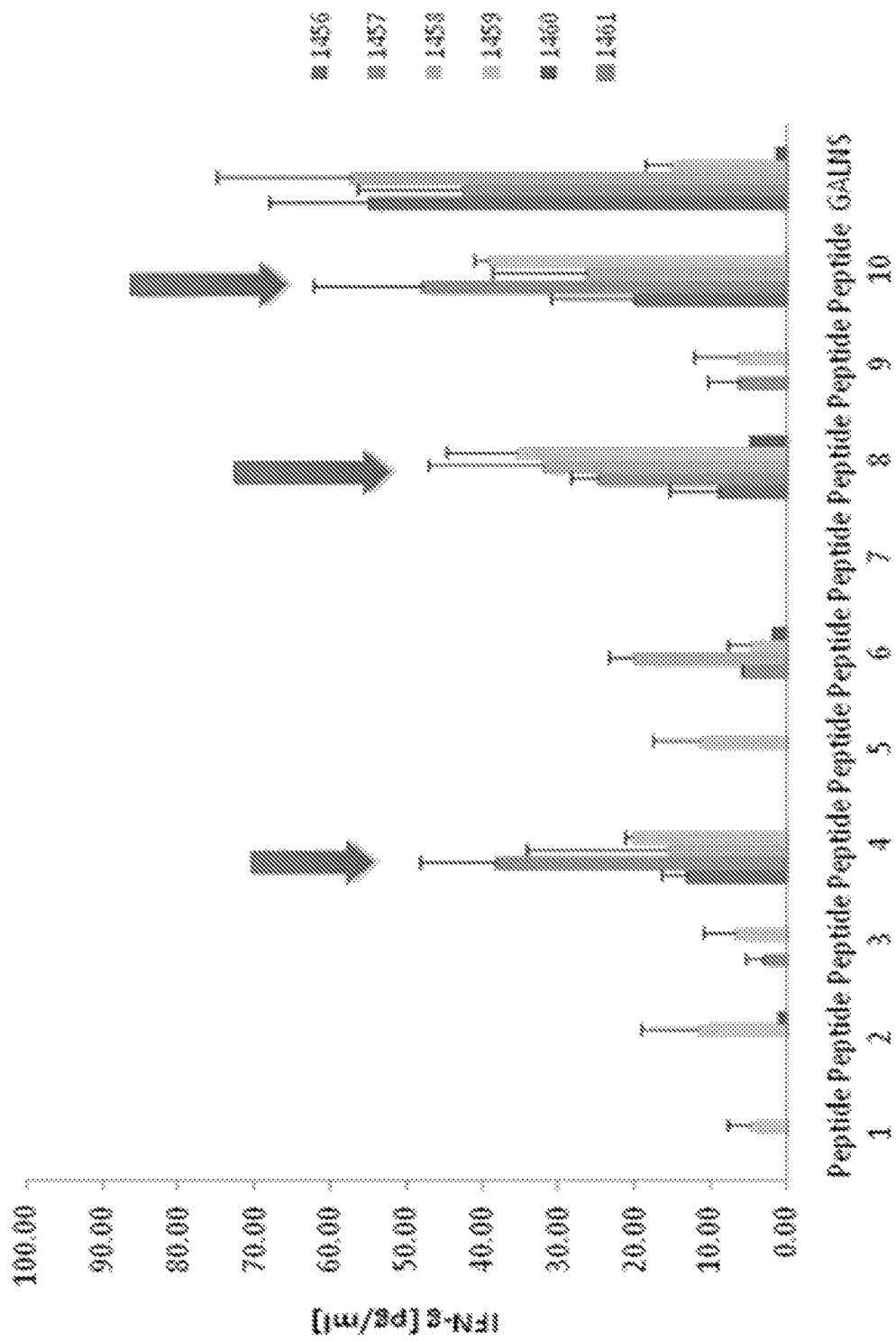
Figure 3:
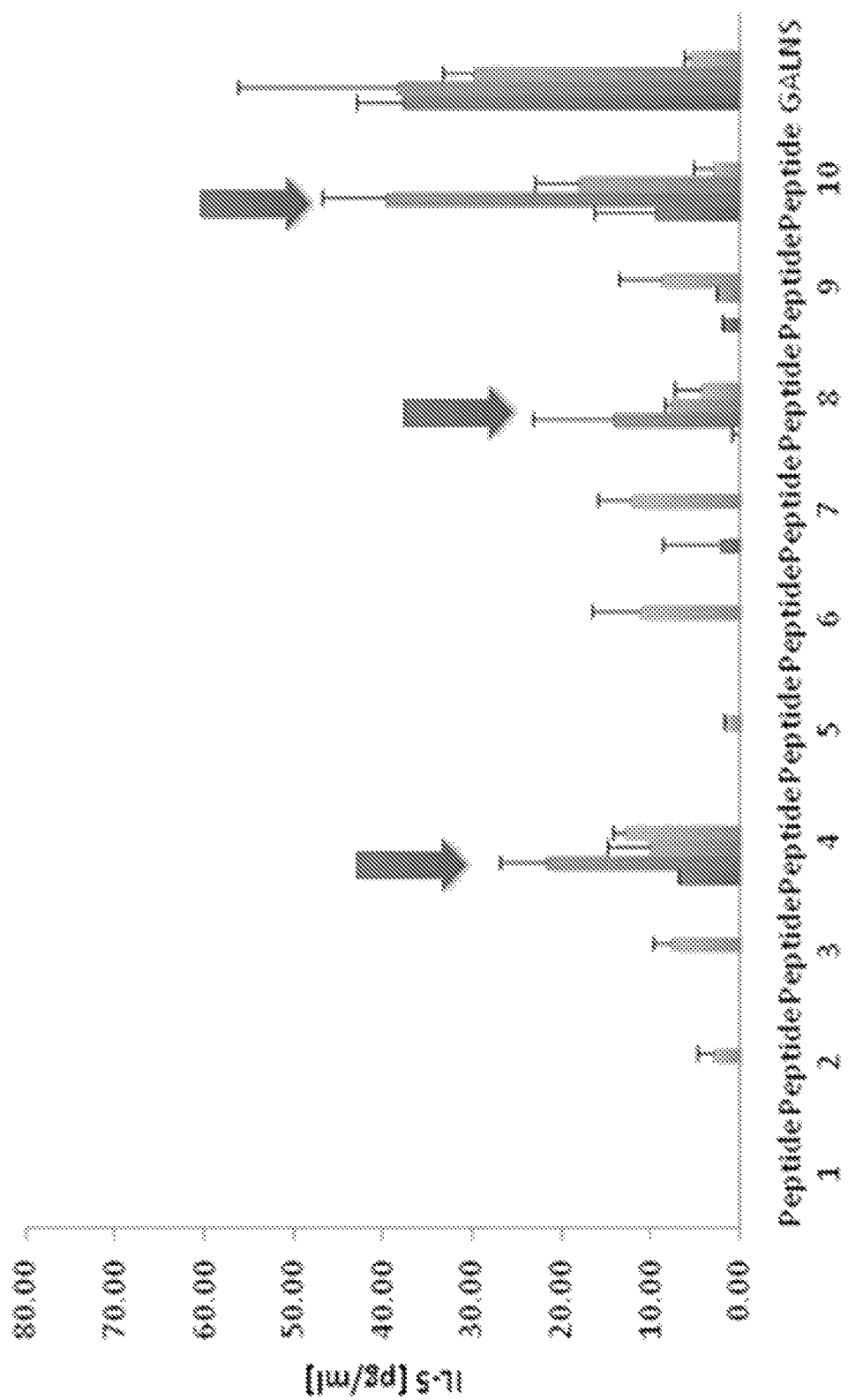

Splenocytes were harvested from MKC mice after treatment with enzyme replacement therapy using GALNS, and maintained in culture. After treatment of cultures with the potential Immunodominant peptides, analysis of the supernatant from these cultures revealed that three peptides, Nos. 4, S, and 10, elicited a strong response as indicated by the secretion of cytokines IL-5 and IFN-γ (FIGS. 2 and 3).

Example 4

Figure 4:
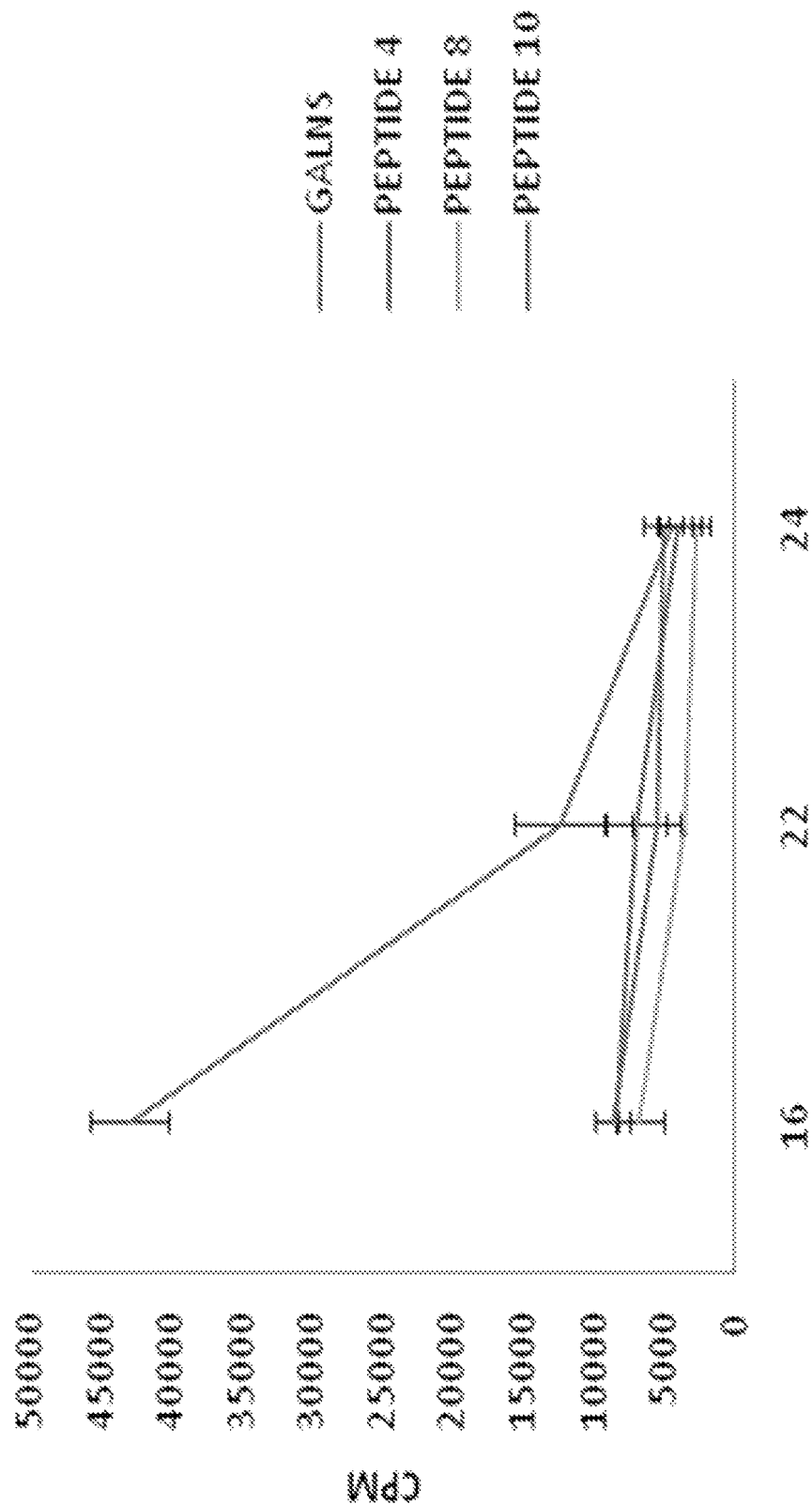

The proliferation of splenocytes stimulated by GALNS or peptides Nos. 4, S, 10, was examined relative to the age of the animal and length of treatment. The results show the highest response at 16 weeks (FIG. 4).

Evaluation of Predicted Immunodominant Peptides

In Examples 5-7, the immunodominant sequences predicted in Example 1 were retested in MKC mice. Cellular response was evaluated by splenocytes proliferation and secretion of proinflammatory cytokines (IFN-γ, IL-4, IL-5 and IL-13) after in vitro stimulation with individual peptides or GALNS in MKC mice treated by ERT.

Example 5

Screening of Peptides by Splenocytes Proliferation

The cpm values of 3H-thymidine incorporation after in vitro stimulation of splenocytes with individual peptides or GALNS in treated mice by 16 or 22 i.v. infusions of human GALNS were evaluated. The mean of proliferation of GALNS treated MKC mice (16 i.v. infusions) was statistically significant when compared to the values of PBS treated mice after in vitro stimulation with peptides C4, ES, I10 or GALNS (p=0.024; 0.022; 0.042 and 0.0243 respectively) (FIG. SA).

Figure 8:
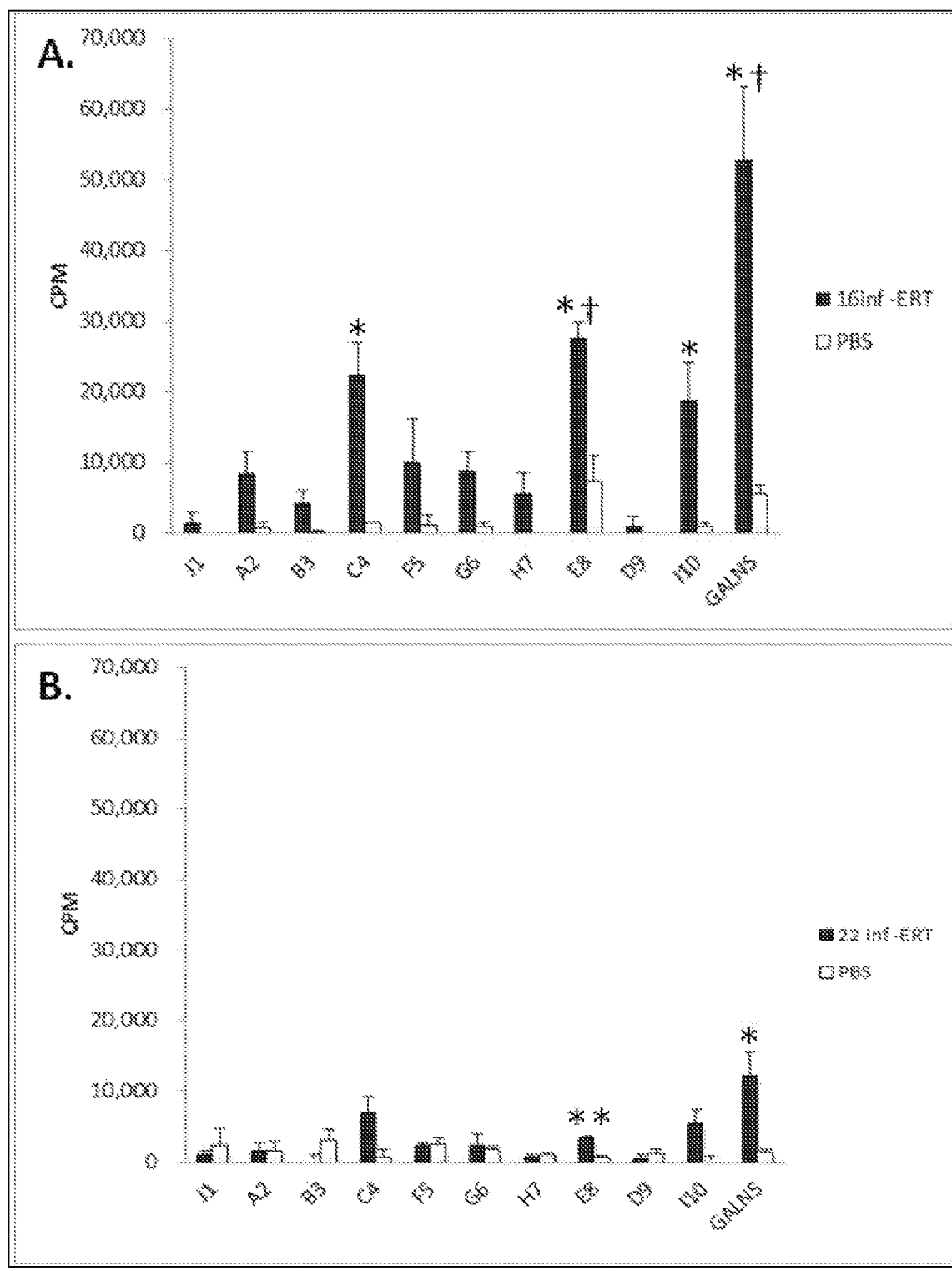

For GALNS treated MKC mice (22 i.v. infusions) only the mean values of splenocytes proliferation after in vitro stimulation with peptide ES or GALNS were statistically significant when compared with PBS treated mice or GALNS treated mice (16 i.v. infusions) (p=0.0004 and 0.0433; p=0.0041 and p=00.0353 respectively) (FIG. 8B).

Example 6

Figure 9:
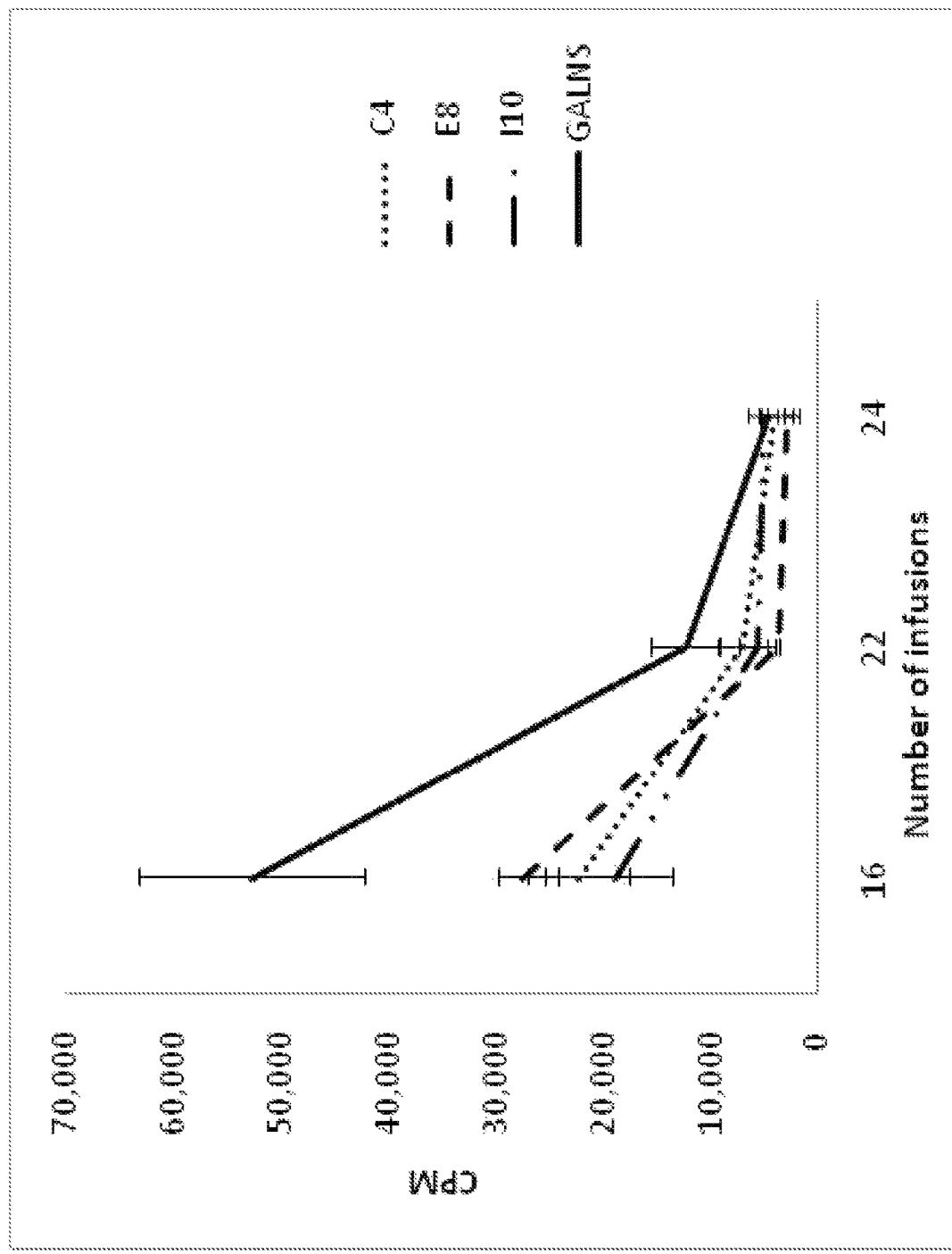

There is a relationship between the number of weekly i.v. infusions (16, 22 and 24) and the cpm values of splenocytes proliferation after in vitro stimulation with peptides C4, ES and I10 and the complete protein in the MKC mice treated by ERT (FIG. 9). With higher number of infusions, lower levels of proliferation were obtained. This result suggests onset of desensitization and/or an age-dependent effect on the immune response towards the treatment.

Example 7

Determination of Cytokines Profile

Figure 10:
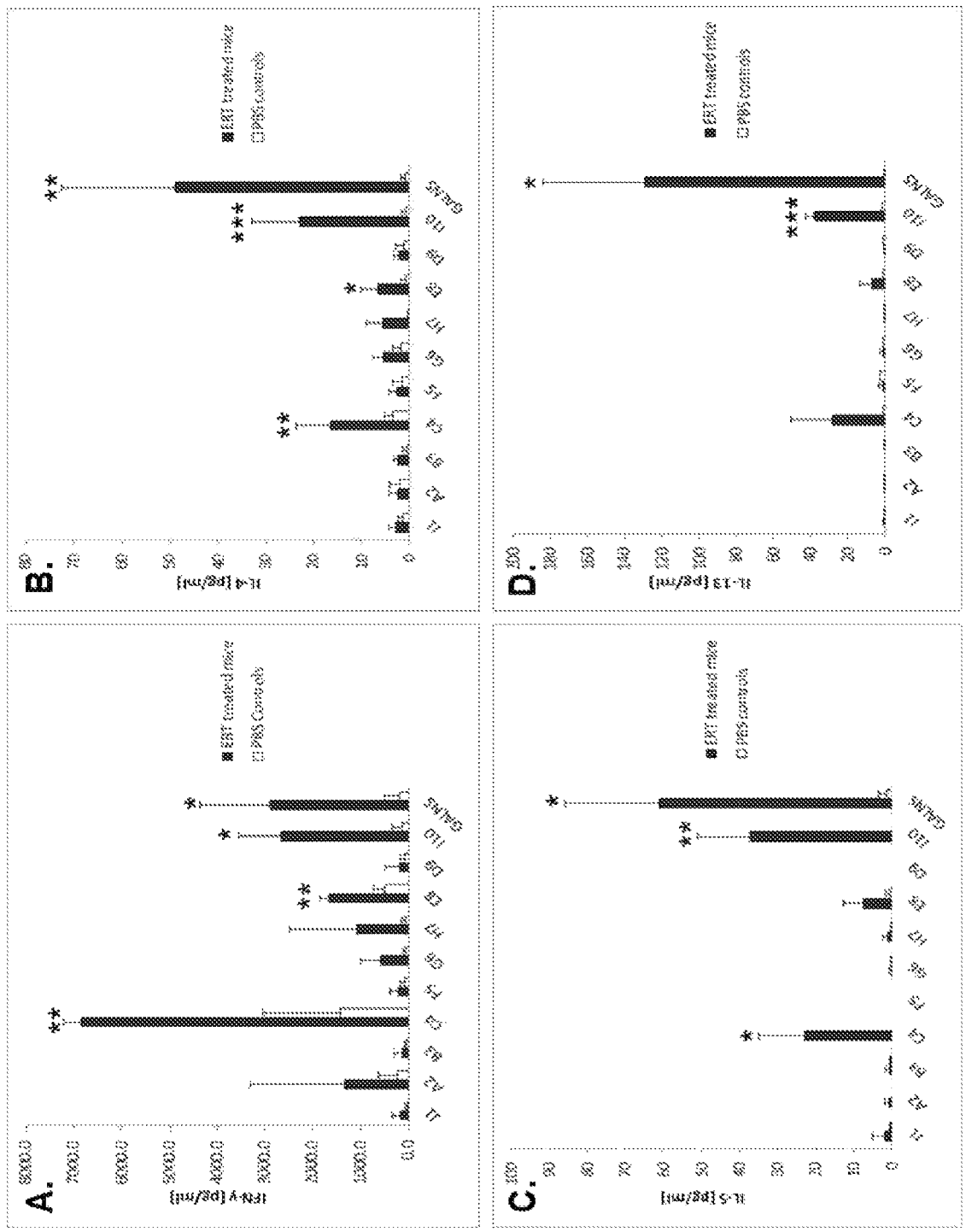

CD4+ T cells play a significant role in the development and performance of cellular and humoral responses of adaptive immune system. There are different linages of effector T helper (Th) cells, which differentiate from naive CD4+ T cells. Th1 cells are characterized by the production of IFN-γ and Th2 by the secretion of IL-4, IL-5 and IL-13 (Amsen et al. (2009) Curr. Opin. Immunol. 21(2): p. 153-60). In order to differentiate the capacity of the peptides to modulate a Th1 or Th2 response, a profile of cytokines was characterized. IFN-γ IL-4, IL-5 and IL-13 were measured as Th1 or Th2 markers. In accordance with the proliferation results, the profile of secreted cytokines showed that only peptides C4, ES and I10 and the complete protein in the in vitro stimulation of splenocytes of MKC mice treated by ERT showed statistically significant difference when compared with PBS treated mice (FIG. 10).

The levels of secreted IFN-γ in ERT treated MKC mice were statistically significant different when compared with PBS controls for peptides C4, ES and I10 and for GALNS (p=$0.00^{48}$, 0.0029, 0.0101 and 0.036 respectively) (FIG. 10A). Peptide C4 induced the highest levels of secreted IFN-γ among the group of peptides and even compared with GALNS in the in vitro stimulation. This result indicates that peptide C4 modulates a stronger Th1 response.

Secretion of IL-4 was observed in the in vitro stimulation with the three peptides (C4, ES and I10) or with GALNS in the ERT MKC mice. The differences were statistically significant when compared with PBS controls (p=0.0016, 0.038, 0.0005 and 0.0026 respectively) (FIG. 10B). Higher levels of IL-4 secretion were detected for GALNS or peptide I10 stimulation.

For IL-5 secretion, only peptides C4 and I10 and GALNS protein exhibited a statistically significant difference after the in vitro stimulation in ERT treated MKC mice compared with the PBS controls (p=0.028, 0.0094 and 0.0029) (FIG. 10C). Higher levels of secretion were detected for GALNS and peptide I10 stimulation. Stimulation with peptide ES did not induce a significant IL-5 response.

Statistically significant difference in IL-13 secretion was observed exclusively for peptide I10 and GALNS after the in vitro stimulation in the ERT treated MKC mice when compared with the PBS controls (p=0.0002 and 0.0152). The levels obtained after C4 or ES stimulations were not statistically significant (FIG. 10D).

Determination of Humoral and Cellular Response of Morquio a Mice Models and Wild Type Mice Treated by ERT

Example 8

Figure 11:
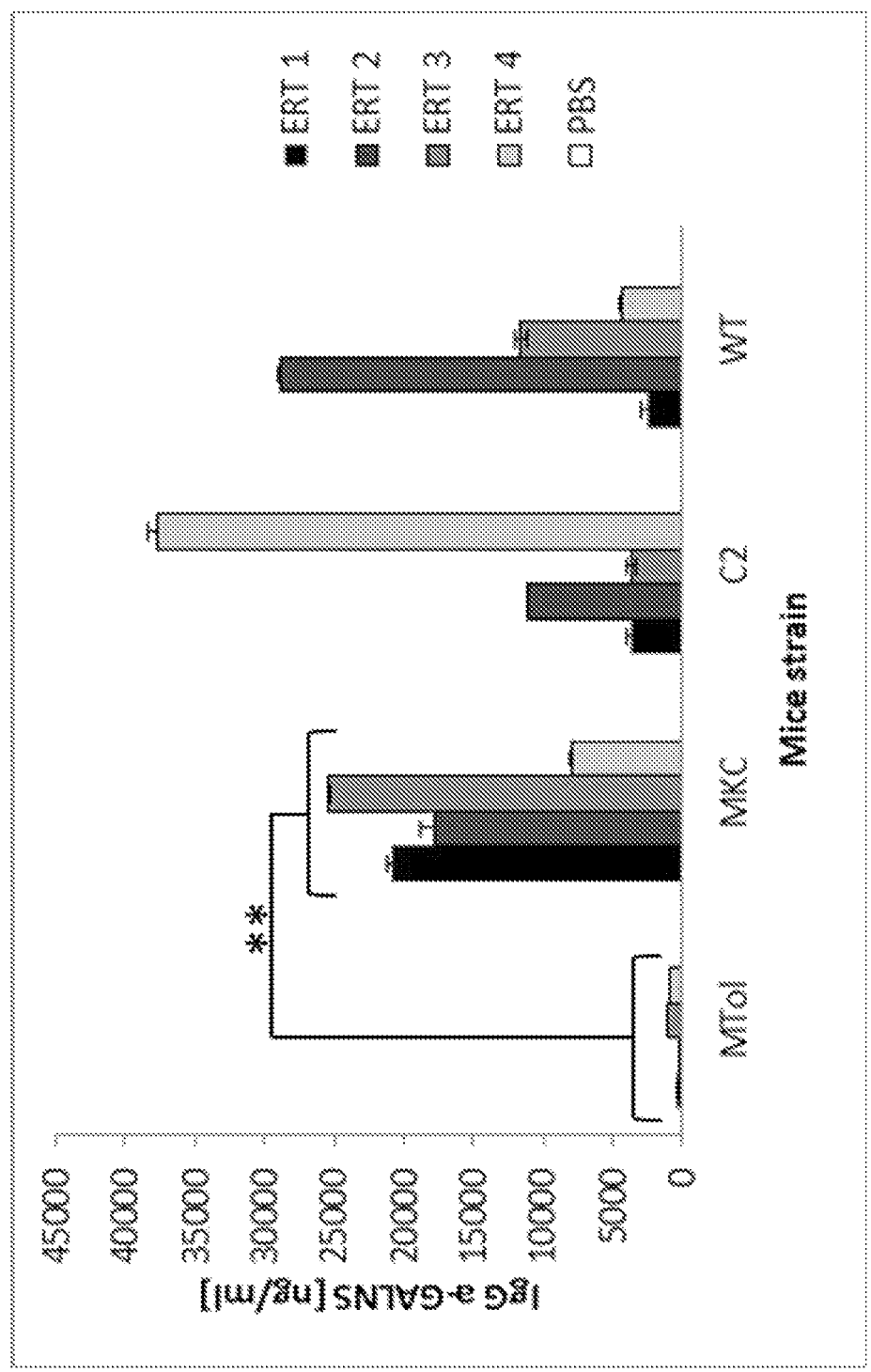

Humoral Response in Mice Treated by ERT Humoral response against GALNS used in ERT was evaluated in Morquio A mice and WT mice. After 16 i.v. infusions of GALNS or PBS, the concentration of IgG anti-GALNS in plasma was determined by ELISA. MKC mice presented a stronger and more homogeneous response than to C2 and WT mice, which had a heterogeneous humoral response against GALNS. As expected, MTol mice showed the lowest levels of response to the therapy (FIG. 11). Only MKC mice treated by ERT presented a statistically significant difference in the levels of GALNS-specific IgG plasma levels when compared with treated MTol mice (p=0.003)

Evaluation of Levels of Proliferation by In Vitro Stimulation of Splenocytes in Mice Treated by ERT

Example 9

Cellular response against GALNS or the most immunogenic peptides (C4, ES and I10) was evaluated in the Morquio A mice models (MKC, C2 and MTol) and in WT mice treated by ERT (16 i.v. infusions of GALNS) or PBS controls in terms of splenocyte proliferation and profile of cytokine secretion. As seen in the humoral response, MKC mice presented a higher and more homogeneous cellular response. Whereas, the response observed in the C2 and WT mice was more heterogeneous.

Figure 12:
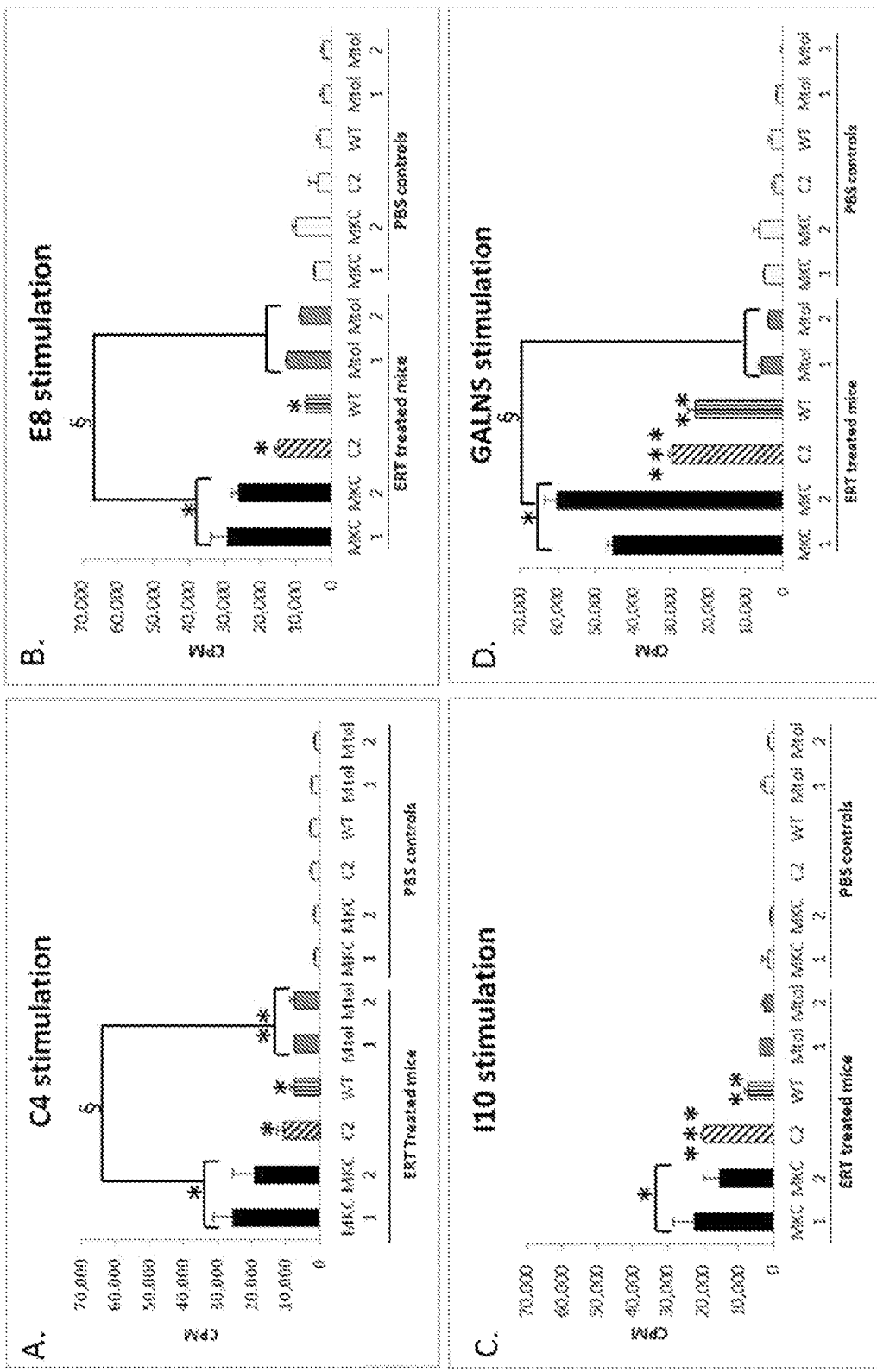

Levels of splenocytes proliferation observed after the in vitro stimulation with the three peptides (C4, ES and I10) or GALNS enzyme among the Morquio A mouse models was higher for MKC mice treated by ERT and the difference was statistically significant when compared with MKC PBS controls (FIG. 12). As seen in the humoral response, MTol mice treated by ERT presented the lower levels of proliferation among the group. The difference in splenocytes proliferation was statistically significant only after in vitro stimulation with peptide C4 when compared with MTol PBS controls (p=0.0056). The differences between the proliferation levels of the MKC and MTol mice treated by ERT were statistically significant for peptides C4 and ES and for GALNS enzyme (p=0.045, 0.02 and 0.023 respectively). WT and C2 ERT treated mice had a statistically significant difference in proliferation values when compared with the PBS controls (of each strain) after the in vitro stimulation with the three peptides and GALNS enzyme.

Cytokines Profile after Splenocytes In Vitro Stimulation in Mice Treated by ERT

Example 10

Figure 13:
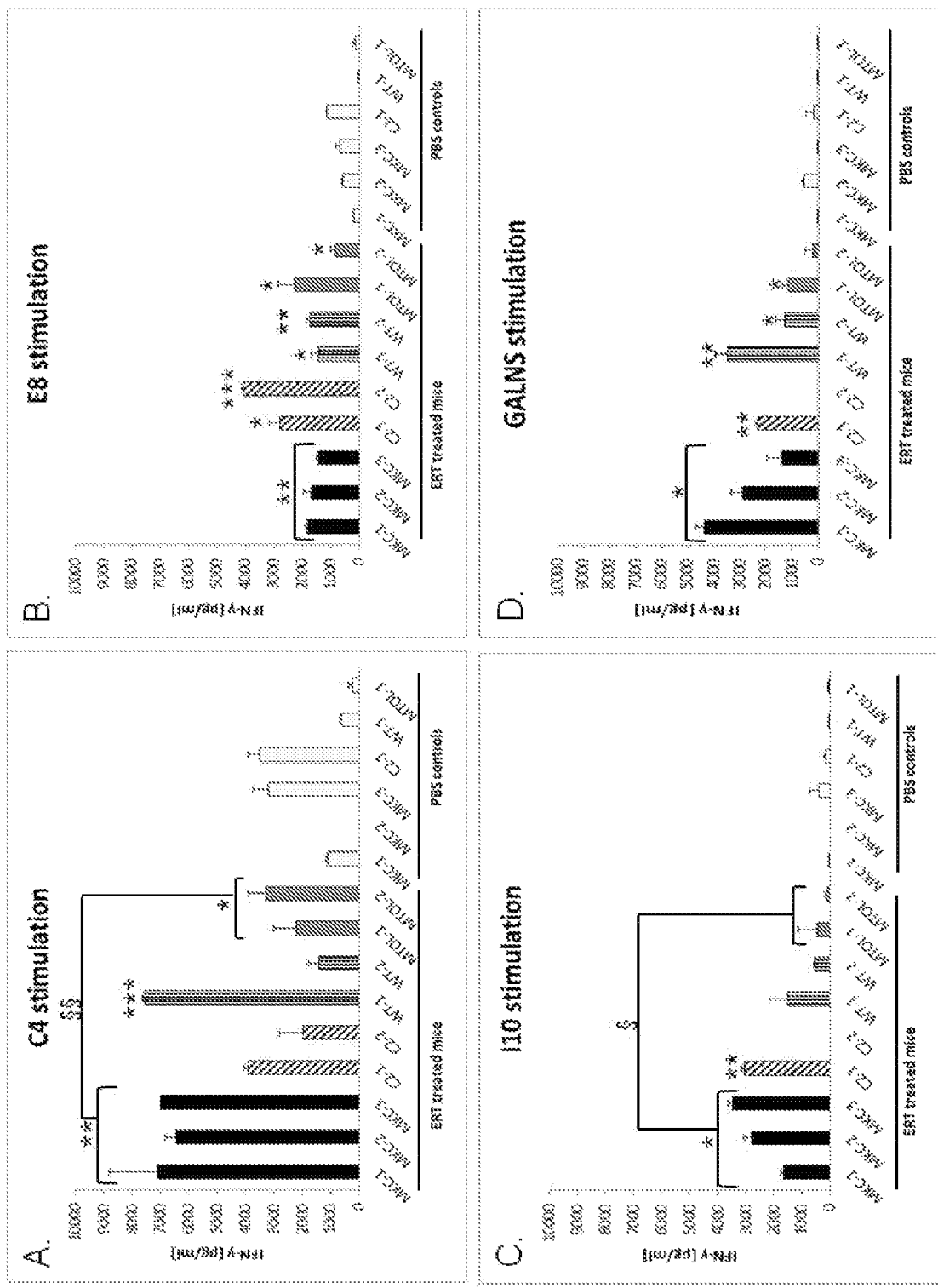

The profile of cytokines secretion after splenocytes in vitro stimulation with peptides C4, ES and I10 or the complete enzyme was evaluated. Peptide C4 induced the strongest response in the IFN-γ secretion if compared with the other stimuli. The difference in levels of IFN-γ secretion for MKC mice treated by ERT was statistically significant when compared with MTol mice treated by ERT after in vitro stimulation with peptides C4 and I10 (p=0.00$^{33}$ and 0.044 respectively). The differences for peptide ES or GALNS stimulation in these two groups (MKC and MTol) were not statistically significant. In vitro stimulation with peptide ES induced statistically significant levels of IFN-γ secretion in all mice treated by ERT when compared with the PBS controls of the same strain (FIG. 13).

Example 11

Figure 14:
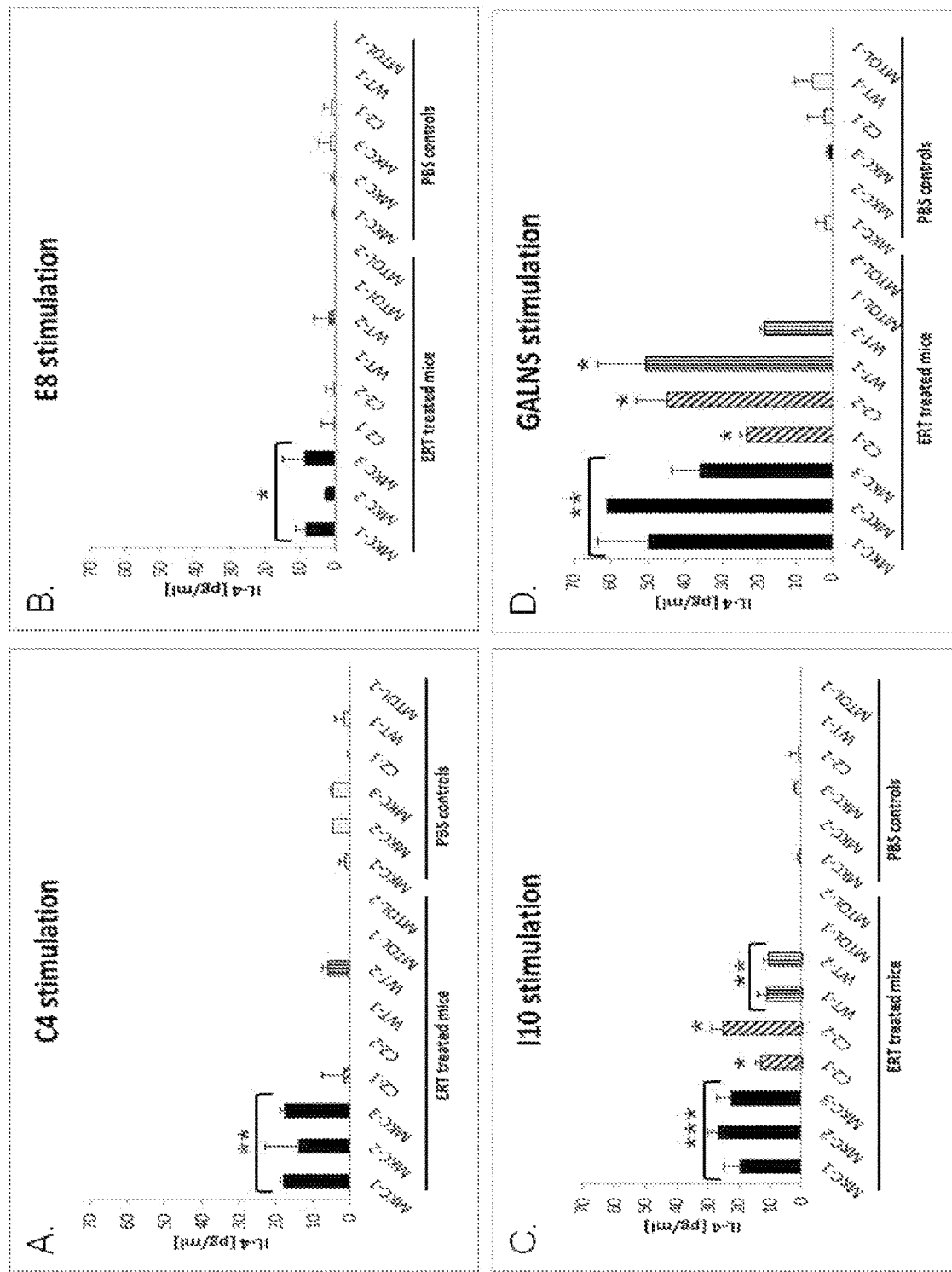

MKC mice treated by ERT presented the highest levels of IL-4 secretion among the treated mice. The differences compared with the MKC PBS controls were statistically significant after the stimulation with the three peptides (C4, ES or I10) or GALNS (p=0.0016, 0.0387, 0.0005 and 0.0026 respectively). For C2 and WT mice the differences were statistically significant only for peptide I10 (C2 mice p=0.02 and 0.012; WT mice p=0.0015) and GALNS stimulation (C2 mice p=0.021 and 0.022; WT mouse p=0.045). MTol mice did not present secretion of IL-4 in any case (FIG. 14).

Example 12

Stimulation with peptide ES did not induce IL-5 secretion in any of the mice models treated by ERT with a statistically significant difference if compared with the PBS controls. In the case of peptide C4 stimulation, it presented a lower but still statistically significant difference in the secretion of IL-5 in MKC (p=0.028) and WT mice (p=0.023 and 0.0019) treated by ERT if compared with the PBS controls. The profile of IL-5 secretion was higher and the difference was statistically significant for MKC, C2 and WT mice treated by ERT after stimulation with either peptide I10 (MKC mice p=0.0094; C2 mice p=0.0088 and 0.0093; WT mice p=0.0154 and 0.049) or GALNS (MKC mice p=0.014; C2 mice p=0.039 and 0.0099; WT mice p=0.00$^{28}$). MTol mice did not present secretion of IL-5 in any case (FIG. 15).

Example 13

IL-13 secretion was induced only after stimulation with peptide I10 and the complete protein. For I10 stimulation, MKC ERT treated mice showed statistically significant difference after the in vitro stimulation (p=0.0002). One out of two C2 and WT mice treated by ERT presented IL-13 secretion with statistically significant differences (p=0.0069 and 0.0261 respectively). Stimulation with GALNS showed induction of IL-13 secretion in MKC (p=0.0152), C2 (p=0.029) and WT mice (p=0.002 and 0.012). MTol mice did not show any secretion of IL-13 (FIG. 16).

Induction of Oral Tolerance in MKC Mice

The Inventors evaluated the induction of tolerance to GALNS used in ERT by oral administration of the complete protein or an immunodominant GALNS peptide. According to the evaluation of the immunogenic regions of GALNS, three peptides (C4, ES, and I10) demonstrated specific cellular response after splenocytes in vitro stimulation in mice treated by ERT. Peptide I10 induced a response very similar to the one observed by in vitro stimulation with GALNS. Therefore, in this first approach the Inventors selected the peptide I10 in the induction of oral tolerance. MKC mice received GALNS or peptide I10 by oral gavage at three different doses (Table 2) prior to ERT. Control groups were fed with PBS. One control group was treated by ERT (non-tolerized group) and the other one received i.v. infusions of PBS (untreated group).

Example 14

Evaluation of Oral Tolerance Effect in the Splenocytes Proliferation after GALNS In Vitro Stimulation. The effect of tolerance induction to GALNS on splenocytes proliferation from tolerized and non-tolerized mice treated by ERT was evaluated. Oral gavage administration of peptide I 10 showed a statistically significant decrease in the levels of splenocytes proliferation for two of the groups (50 µg, p=0.0033; 500 µg, p=0.0069) when compared with the values of the non-tolerized mice. The three groups of mice that received GALNS orally, presented a statistically significant decline in the cpm values of proliferation (50 µg, p=0.0105; 100 µg, p=0.0084; 500 µg, p=0.0028). On the other hand, compared with the untreated group, all the tolerized groups (but GALNS 500 µg) and the non-tolerized group exhibited statistically significant differences in the cpm values (I10 50 µg, p=0.026; I10 100 µg, p=0.0002; I10

500 μg, p=0.0144; GALNS 50 μg, p=0.048; GALNS 100 μg, p=0.0099 and ERT-PBS p=0.0018) (FIG. 17).

Effect of Tolerance Induction on the Secreted Cytokine

Cytokine secretion was evaluated in culture supernatants after in vitro stimulation of splenocytes in tolerized and non-tolerized mice treated by ERT. The results demonstrated that there was an effect in the profile of cytokines in mice orally treated.

Example 15

Evaluation of IFN-γ Secretion after Induction of Tolerance. As seen in FIG. 18, secretion in the production of IFN-γ (Th1-type cytokine) was down-regulated in mice treated orally with the peptide I10. The decrease was statistically significant when compared with the non-tolerized group for the mice that were fed with 50 μg (p=0.01$^{23}$) or 500 μg (p=0.0197) of the peptide. Interestingly, the mice that received GALNS orally did not show any modulation in the IFN-γ secretion after splenocytes in vitro stimulation with GALNS. In comparison with untreated mice, only the non-tolerized mice showed a statistically significant difference in the levels of IFN-γ secretion (p=0.0074).

Example 16

Effect of Induction of Tolerance on IL-4 Secretion. IL-4 (Th2-biased cytokine) production by splenocytes after in vitro stimulation with GALNS was evaluated. The results showed a statistically significant decrease in the secreted IL-4 by splenocytes of the tolerized groups with I10 50 μg (p=0.0053), I10 500 μg (p=0.0196), GALNS 100 μg (p=0.01$^{23}$) and GALNS 500 μg (p=0.00$^{46}$) if compared with the non-tolerized mice. The difference in the IL-4 levels of the untreated mice was statistically significant when compared only with the mice treated by GALNS 100 μg (p=0.0321) and the non-tolerized group (p=0.00$^{46}$) (FIG. 19).

Example 17

Determination of IL-5 and IL-13 after Induction of Tolerance. The induction of tolerance did not show any effect on the levels of the Th2-biased secreted cytokines (IL-5 and IL-13). All tolerized groups presented elevated values of IL-5 and IL-13 without statistically significant difference when compared with the values obtained in the non-tolerized mice (FIG. 20-21).

Example 18

Effect of Tolerance on the Il10 Induction. Surprisingly, the levels of IL-10 were not increased in some of the tolerized groups that showed inhibition in the GALNS-specific splenocytes proliferation (FIG. 13) The difference was statistically significant for the groups treated with peptide I10 50 μg (p=0.0368) and GALNS 500 μg (p=0.0301), when compared with the non-tolerized mice. The increased levels of IL-10 in the non-tolerized group could be explained as a mechanism to counteract the induced levels of Th1 and Th2-type cytokines (FIG. 18-21). The induction of this mechanism was not seen for the mice treated with GALNS orally, which presented induction of IFN-g secretion with down-regulation of IL-10 (FIG. 22).

Effect of Oral Tolerance in Humoral Response: GALNS Specific IgG and IgE Levels in Plasma in Mice Treated by ERT Example 19

GALNS Specific IgG Plasma Levels. IgG plasma levels against GALNS were determined in the samples obtained one week after the last infusion by ELISA. IgG antibodies of untreated mice did not show crossreaction to GALNS. The GALNS specific IgG values were compared to the obtained levels in the non-tolerized mice. The reduction in the IgG values was statistically significant only in the groups treated orally with I10 50 μg (p=0.0086), GALNS 100 μg (p=0.033) and GALNS 500 μg (p=0.00$^{48}$). The mice treated orally with peptide I10 100 μg and 500 μg or GALNS 50 g, showed same levels or in some cases higher levels of IgG antibodies against GALNS when compared with the values in the non-tolerized group (FIG. 23).

Example 20

GALNS Specific IgE Plasma Levels. IgE plasma levels against GALNS were determined by ELISA in the samples obtained one week after the last infusion of GALNS or PBS. In accordance with the results of GALNS specific IgG levels, the reduction when compared with the IgG values in the non-tolerized group, was statistically significant only for the groups treated orally with peptide I10 50 μg (p=0.0194) and GALNS 500 g (p=0.0057). Furthermore, a comparison between mice treated by ERT (tolerized and non-tolerized) and untreated mice was performed. The increased levels of GALNS specific IgE was statistically significant for the groups treated orally with peptide I10 100 g (p=0.0061), I10 500 g (p=0.0057) and nontolerized group (p=0.0042) (FIG. 24).

Example 21

Regulatory Markers Evaluation in Peyer Patches (PP) after Induction of Tolerance. One week after the last i.v. infusion of GALNS or PBS, PP of mice were dissected and mRNA was extracted in order to evaluate the expression of regulatory markers: cytotoxic T lymphocyte antigen 4 (CTLA-4) and TGF-β. Most of the mice presented up-regulation of these regulatory molecules when compare with the non-tolerized group. CTLA-4 was predominantly up-regulated in mice treated orally with peptide I10, while the expression of TGF-β was observed in both groups (FIGS. 25 and 26).

Comparison of ERT Efficacy Between Tolerized and Non-Tolerized MPS Iva Knock-Out Mice.

The effect of oral tolerance on the efficacy of ERT was evaluated pathologically by two different approaches. 1). Determination of GAGs accumulation in liver as a result of GALNS enzyme deficiency and 2). Evaluation of immune-complex deposits in kidney as a secondary effect of immune response to ERT.

Example 22

Evaluation of Gags Accumulation. Pathological evaluation GAGs accumulation of mice treated by ERT after induction of oral tolerance was performed in mice livers. These sections of tissues were stained with Toluidine blue and evaluated by light microscopy. The pictures of each slide were qualified from zero to five according to the level of accumulation. Where, zero means no accumulation and five, highest level of accumulation (usually found in older and untreated Morquio A mice). The level of accumulation for each mouse resulted as an additive value of each qualification. Most of the tolerized groups showed an improvement in the reduction of GAGs accumulation compared with the non-tolerized or the untreated group. The difference was statistically significant for the groups treated with peptide I10 50 µg (p=0.0036), I10 500 µg (p=0.0022), GALNS 50 µg (p=0.0114), GALNS 100 µg (p=0.0314) and GALNS 500 µg (p=0.0027) (FIG. 27).

Example 23

Determination of Immune-Complex Deposits. Antibodies against proteins used for ERT cause, in some of the cases, glomerulonephritis which results from the immune-complex deposits in kidney. The pictures of each slide were qualified from zero to five according to the level of immune-complex deposits. Where, zero means no deposits and five, highest level of immune-complex. The level of accumulation for each mouse resulted as an additive value of each qualification. The pathological evaluation showed a statistically significant decline in the immune-complex depositions inside of the glomerular. Compared with the non-tolerized group there was a statistically significant reduction in the levels of immune-complex deposit for the groups treated by peptide I10 50 µg (p=0.0002), I10 100 µg (p=0.0042), I10 500 µg (p=0.0275), GALNS 100 µg (p=0.0012) and GALNS 500 µg (p=0.0063) (FIG. 28).

There is a direct correlation between the amount of immunoglobulins against GALNS used in ERT, the levels of immune-complex deposits and the grade of GAG's accumulation. This correlation is demonstrated pathologically in FIGS. 29-36. The lower the levels of immune-complex deposits, the lower the levels of GAG's accumulation.

All publications and patents cited in this specification are hereby incorporated by reference in their entirety. The discussion of the references herein is intended merely to summarize the assertions made by the authors and no admission is made that any reference constitutes prior art. Applicants reserve the right to challenge the accuracy and pertinence of the cited references.

What is claimed is:

1. A method for treating mucopolysaccharidosis type IVA in a subject suffering from mucopolysaccharidosis type IVA, the method comprising: administering to the subject an effective amount of a polypeptide selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and combinations thereof.

2. The method of claim 1, wherein the polypeptide is SEQ ID NO:12.

3. The method of claim 1, wherein the effective amount ranges from about 50 μg per administration to about 500 μg per administration.

4. The method of claim 1, wherein the polypeptide is administered for 10 weeks.

5. The method of claim 4, wherein the polypeptide is administered about every other day for 10 weeks.

6. The method of claim 1, wherein the administering is oral administration.

7. The method of claim 1, further comprising administering to the subject N-acetyl galactosamine-6-sulfate sulfatase.

8. The method of claim 7, wherein the N-acetyl galactosamine-6-sulfate sulfatase is N-acetyl galactosamine-6-sulfate sulfatase enzyme replacement therapy.

9. The method of claim 7, wherein the administering is infusion.

10. The method of claim 7, wherein the N-acetyl galactosamine-6-sulfate sulfatase ranges from about 50 µg per administration to about 500 µg per administration.

11. The method of claim 1, wherein the subject is or has received N-acetyl galactosamine-6-sulfate sulfatase.

12. The method of claim 11, wherein the N-acetyl galactosamine-6-sulfate sulfatase is N-acetyl galactosamine-6-sulfate sulfatase enzyme replacement therapy.

13. The method of claim 11, wherein the administering is infusion.

* * * * *